US008129403B2

(12) United States Patent
Lamb et al.

(10) Patent No.: US 8,129,403 B2
(45) Date of Patent: Mar. 6, 2012

(54) CHEMICAL COMPOUNDS

(75) Inventors: Michelle Lamb, Belmont, MA (US); Tao Wang, Sudbury, MA (US); Dingwei Yu, Natick, MA (US); Peter Mohr, Boulder, CO (US); Bin Wang, Longmont, CO (US)

(73) Assignee: AstraZeneca AB, Sodertalje (SE)

( * ) Notice: Subject to any disclaimer, the term of this patent is extended or adjusted under 35 U.S.C. 154(b) by 697 days.

(21) Appl. No.: 11/816,374

(22) PCT Filed: Feb. 15, 2006

(86) PCT No.: PCT/GB2006/000513
§ 371 (c)(1),
(2), (4) Date: Jan. 10, 2008

(87) PCT Pub. No.: WO2006/087530
PCT Pub. Date: Aug. 24, 2006

(65) Prior Publication Data
US 2008/0176872 A1 Jul. 24, 2008

Related U.S. Application Data

(60) Provisional application No. 60/653,575, filed on Feb. 16, 2005, provisional application No. 60/742,138, filed on Dec. 1, 2005.

(51) Int. Cl.
*A61K 31/44* (2006.01)
*C07D 513/02* (2006.01)
*C07D 515/02* (2006.01)

(52) U.S. Cl. ......... 514/300; 514/303; 546/117; 546/118

(58) Field of Classification Search .................. 514/300, 514/303; 546/117, 118
See application file for complete search history.

(56) References Cited

U.S. PATENT DOCUMENTS

| | | | |
|---|---|---|---|
| 3,897,443 A | 7/1975 | Sharpe | |
| 4,038,240 A | 7/1977 | Hugl et al. | |
| 4,485,284 A | 11/1984 | Pakulis et al. | |
| 5,147,876 A | 9/1992 | Mizuchi et al. | |
| 5,459,318 A | 10/1995 | Cacho et al. | |
| 5,521,184 A | 5/1996 | Zimmermann | |
| 6,383,553 B1 | 5/2002 | Tondar et al. | |
| 6,399,780 B1 | 6/2002 | Hudkins et al. | |
| 6,455,525 B1 | 9/2002 | Singh et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,696,452 B2 | 2/2004 | Davies et al. | |
| 6,727,251 B2 | 4/2004 | Bebbington et al. | |
| 6,989,385 B2 | 1/2006 | Bebbington et al. | |
| 7,008,948 B2 | 3/2006 | Bebbington et al. | |
| 7,087,603 B2 | 8/2006 | Bebbington et al. | |
| 7,098,330 B2 | 8/2006 | Bebbington et al. | |
| 7,115,739 B2 | 10/2006 | Bebbington et al. | |
| 7,148,455 B2 | 12/2006 | Scalese et al. | |
| 7,183,307 B2 | 2/2007 | Hale et al. | |
| 7,279,476 B2 | 10/2007 | Tang et al. | |
| 7,390,815 B2 | 6/2008 | Davies et al. | |
| 7,427,681 B2 | 9/2008 | Bebbington et al. | |
| 7,473,691 B2 | 1/2009 | Davies et al. | |
| 7,521,453 B2 | 4/2009 | Barlaam et al. | |
| 7,528,138 B2 | 5/2009 | Knegtel et al. | |
| 7,528,142 B2 | 5/2009 | Binch et al. | |
| 7,531,536 B2 | 5/2009 | Bebbington et al. | |
| 2003/0055068 A1 | 3/2003 | Bebbington et al. | |
| 2003/0078275 A1 | 4/2003 | Bebbington et al. | |
| 2003/0079365 A1 | 5/2003 | Corak et al. | |
| 2003/0105090 A1 | 6/2003 | Bebbington et al. | |
| 2005/0038023 A1 | 2/2005 | Bebbington et al. | |
| 2005/0054638 A1 | 3/2005 | Barlaam et al. | |
| 2007/0142413 A1 | 6/2007 | Block et al. | |
| 2008/0004302 A1 | 1/2008 | Theoclitou et al. | |
| 2008/0108633 A1 | 5/2008 | Claesson | |
| 2008/0108669 A1 | 5/2008 | Claesson | |
| 2008/0176872 A1 | 7/2008 | Lamb et al. | |
| 2008/0194606 A1 | 8/2008 | Scott et al. | |
| 2008/0287437 A1 | 11/2008 | Wang et al. | |
| 2008/0287475 A1 | 11/2008 | Feng et al. | |
| 2009/0005396 A1 | 1/2009 | Claesson | |
| 2010/0152219 A1 | 6/2010 | Block et al. | |

FOREIGN PATENT DOCUMENTS

| | | |
|---|---|---|
| EP | 0401358 | 12/1990 |
| EP | 1317448 B1 | 5/2005 |
| EP | 1317444 B1 | 5/2006 |
| EP | 1317447 B1 | 5/2006 |
| EP | 1317449 B1 | 5/2006 |
| EP | 1317452 B1 | 5/2006 |
| EP | 1318997 B1 | 5/2006 |
| EP | 1345922 B1 | 5/2006 |
| EP | 1345926 B1 | 5/2006 |
| EP | 1345927 B1 | 5/2006 |
| EP | 1345929 B1 | 5/2006 |
| EP | 1353916 B1 | 9/2006 |
| EP | 1345928 B1 | 2/2007 |
| EP | 1876178 | 1/2008 |
| EP | 1686999 | 7/2009 |

(Continued)

OTHER PUBLICATIONS

Dzvinchuk et al., Chemistry of Heterocyclic Compounds (New York)(Translation of Khimiya Geterotsiklicheskikh Soedinenii) (1998), Volume Date 1997, 33(8), 992-993.*
Rueckle et al., Journal of Medicinal Chemistry (2004), 47(27), pp. 6921-6934.*
Aimone et al. "Antinociceptive Activity of Selective Tyrosine Kinase Inhibitors in the Rat". Abstracts of the Annual Meeting of the Society for Neuroscience (2000), vol. 26, No. 1-2, 1692, XP008129558.

(Continued)

*Primary Examiner* — D M Seaman
*Assistant Examiner* — Niloofar Rahmani

(57) ABSTRACT

This invention relates to novel compounds having the formula (I); and to their pharmaceutical compositions and to their methods of use. These novel compounds provide a treatment for cancer.

14 Claims, No Drawings

FOREIGN PATENT DOCUMENTS

| | | |
|---|---|---|
| WO | WO 95/09852 | 4/1995 |
| WO | WO 97/09325 | 3/1997 |
| WO | WO 97/19065 | 5/1997 |
| WO | WO 98/38171 | 9/1998 |
| WO | WO 99/41253 | 8/1999 |
| WO | 00/14552 A1 | 3/2000 |
| WO | 00/16067 A1 | 3/2000 |
| WO | WO 00/12485 | 3/2000 |
| WO | WO 00/27825 | 5/2000 |
| WO | WO 00/35455 | 6/2000 |
| WO | 00/39101 A1 | 7/2000 |
| WO | WO 00/53595 | 9/2000 |
| WO | WO 00/63182 | 10/2000 |
| WO | WO 00/73344 | 12/2000 |
| WO | WO 00/78731 | 12/2000 |
| WO | WO 01/17995 | 3/2001 |
| WO | WO 01/22938 | 4/2001 |
| WO | WO 01/47921 | 7/2001 |
| WO | WO 01/60816 | 8/2001 |
| WO | WO 01/64655 | 9/2001 |
| WO | WO 01/64656 | 9/2001 |
| WO | WO 01/85699 | 11/2001 |
| WO | 02/22601 A1 | 3/2002 |
| WO | WO 02/18346 | 3/2002 |
| WO | WO 02/20479 | 3/2002 |
| WO | WO 02/20513 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | 02/50065 A2 | 6/2002 |
| WO | 02/50066 A2 | 6/2002 |
| WO | WO 02/50071 | 6/2002 |
| WO | WO 02/059111 | 8/2002 |
| WO | WO 02/064096 | 8/2002 |
| WO | 03/026665 A1 | 4/2003 |
| WO | 03/027111 A1 | 4/2003 |
| WO | 03/048133 A1 | 6/2003 |
| WO | WO 2004/037814 | 5/2004 |
| WO | WO 2005/016893 | 2/2005 |
| WO | 2005/048133 A1 | 5/2005 |
| WO | 2005/049033 A1 | 6/2005 |
| WO | 2005/095400 A1 | 10/2005 |
| WO | 2005/103010 A2 | 11/2005 |
| WO | WO 2006/037117 | 4/2006 |
| WO | 2006/048080 A1 | 5/2006 |
| WO | WO 2006/067614 | 6/2006 |
| WO | WO 2006/074057 | 7/2006 |
| WO | 2006/082392 A1 | 8/2006 |
| WO | 2006/087530 A1 | 8/2006 |
| WO | 2006/087538 A1 | 8/2006 |
| WO | 2006/115452 A1 | 11/2006 |
| WO | 2006/123113 A2 | 11/2006 |
| WO | 2007/049041 A1 | 5/2007 |
| WO | WO 2007/071348 | 6/2007 |
| WO | WO 2008/005538 | 1/2008 |
| WO | WO 2008/135785 | 11/2008 |
| WO | WO 2010/038060 | 4/2010 |

OTHER PUBLICATIONS

Alferez et al "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Abstract 471.

Alferez et al "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Poster.

Blowers "AZD8931". IASLC Annual Targeted Therapies of the Treatment of Lung Cancer Meeting (2011), Santa Monica, CA, PowerPoint Presentation.

Breault et al. "Cyclin-Dependent Kinase 4 Inhibitors as a Treatment for Cancer. Part 2: Identification and Optimisation of Substituted 2, 4-Bis Anilino Pyrimidines". Bioorganic & Medicinal Chemistry Letters (2003), vol. 13, 2961-2966.

Cristofanilli et al. "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.

El Kerdaway et al. "2, 4-Bis (substituted)-5-nitropyrimidines of Expected Diuretic Action". Egypt J. Chem (1986), vol. 92, No. 2, 247-251.

Hefti et al. "Novel Class of Pain Drugs Based on Antagonism of NGF". Trends in Pharmacological Sciences (2006), vol. 27, No. 2, 85-91.

Hickinson et al. "AZD8931, an Equipotent, Reversible Inhibitor of Signaling by Epidermal Growht Factor Receptor, ERBB2 (HER2), and ERBB3: A Unique Agent for Simultaneous ERBB Receptor Blockage in Cancer". Clinical Cancer Research (2010) vol. 16, 1159-1169.

International Search Report for corresponding PCT application No. PCT/GB2006/000334.

Keilholz et al. "Phase I Dose-Finding Study of Monotherapy with AZD8931, an Inhibitor of erbBl, 2 and 3 Signaling, in Patients with Advanced Solid Tumors". J Clin Oncol. (2011), vol. 29, Abstract 3097.

Keilholz et al. "Phase I Dose-Finding Study of Monotherapy with AZD8931, an Inhibitor of erbBl, 2 and 3 Signaling, in Patients with Advanced Solid Tumors". ASCO (2011), Poster.

Klinowska et al. "AZD8931, an Equipotent, Reversible Inhibitor of erbBl, erbB2 and erbB3 Receptor Signaling: Characterisation of Pharmacological Profile". European Journal of Cancer Supplements (2009), vol. 7, No. 2, 127.

Leroith and Roberts. "The Insulin-Like Growth Factor System and Cancer". Cancer Letters (2003), vol. 195, 127-137.

Lopez-Martin et al. "Phase I Dose-Finding Study of AZD8931, an Inhibitor of erbB1, 2 and 3 Receptor Signaling, in Combination with Paclitaxel". J Clin. Oncol. (2011), vol. 29, Abstract 3105.

Lopez-Martin et al. "Phase I Dose-Finding Study of AZD8931, an Inhibitor of erbB1, 2 and 3 Receptor Signaling, in Combination with Paclitaxel". ASCO (2011), Poster.

Marshall et al. "Evaluation of AZD8931, an Equipotent Inhibitor of erbB 1, erbB2 and erbB3 Receptor Signaling, on Ligand Stimulated Breast Cancer Cell Lines with Differing Levels of erbB2 Expression". SABCS (2009), Abstract 5059.

Normanno et al. "Target-based therapies in breast cancer: current status and future perspectives". Endocr Relat Cancer (2009), vol. 16(3): 675-702.

Parrizas et al. "Specific Inhibition of Insulin-Like Growth Factor-1 and Insulin Receptor Tyrosine Kinase Activity and Biological Function by Tyrphostins". Endocrinology (1997), vol. 138, No. 4, 1427-1433.

Pierce et al. "Ch . . . O and Ch . . . N. Hydrogen Bonds in Ligand Design: A Novel Quinazolin-4-ylthiazol-2-ylamine Protein Kinase Inhibitor". J. Med. Chem. (2005), vol. 48, 1278-1281.

Simone "Oncology: Introduction, Cecil Textbook of Medicine, 20th Edition" (1996), vol. 1, 1004-1010.

Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.

Thress et al. "Identification and Preclinical Characterization of AZ-23, a Novel, Selective, and Orally Bioavailable Inhibitor of the Trk Kinase Pathway". Molecular Cancer Therapeutics (2009) vol. 8, No. 7, 1818-1827.

Ulrich et al. "Chapter 4: Crystallization". Kirk-Othmer Encyclopedia of Chemical Technology (Aug. 2002).

Vippagunta et al. "Crystalline Solids". Advanced Drug Delivery Reviews (2001), vol. 48, 3-26.

Wang et al. "Identification of 4-Aminopyrazolylpyrimidines as Potent Inhibitors of Trk Kinases". J. Med. Chem. (2008), vol. 51, No. 15, 4672-4684, ACS Publications, DC, US.

Wang et al. "Trik Kinase Inhibitors as New Treatments for Cancer and Pain". Expert Opin. Ther. Patents (2009), vol. 19, No. 3, 305-319.

West "Chapter 10: Solid Solutions". Solid State Chemistry and Its Applications (1988), 358 & 365.

Winston et al. "Suppression of Neuronal Tyrosine Kinase Activity in Associated with Improvement in Pain Responses and Inhibition of Nociceptive Gene Expression in Pancreatitis". Abstracts of the Annual Meeting of the Society for Neuroscience (2001), vol. 27, 2162, XP008129567.

* cited by examiner

CHEMICAL COMPOUNDS

CROSS-REFERENCE TO RELATED APPLICATIONS

This application is a U.S. National Stage under 35 U.S.C. §371 of International Application No. PCT/GB2006/000513 (filed Feb. 15, 2006) which claims priority under 35 U.S.C. §119 (e) to U.S. Provisional Application No. 60/653,575, filed on Feb. 16, 2005, and to U.S. Provisional Application No. 60/742,138, filed on Dec. 1, 2005.

FIELD OF THE INVENTION

The present invention relates to novel pyrazole derivatives, their pharmaceutical compositions and methods of use. In addition, the present invention relates to therapeutic methods for the treatment and prevention of cancers and to the use of these pyrazole derivatives in the manufacture of medicaments for use in the treatment and prevention of cancers.

BACKGROUND OF THE INVENTION

Receptor tyrosine kinases (RTK's) are a sub-family of protein kinases that play a critical role in cell signalling and are involved in a variety of cancer related processes including cell proliferation, survival, angiogenesis and metastasis. Currently up to 100 different RTK's including tropomyosin-related kinases (Trk's) have been identified.

Trk's are the high affinity receptors activated by a group of soluble growth factors called neurotrophins (NT). The Trk receptor family has three members—TrkA, TrkB and TrkC. Among the NTs there are (i) nerve growth factor (NGF) which activates TrkA, (ii) brain-derived growth factor (BDNF) and NT-4/5 which activate TrkB and (iii) NT3 which activates TrkC. Each Trk receptor contains an extra-cellular domain (ligand binding), a trans-membrane region and an intra-cellular domain (including kinase domain). Upon binding of the ligand, the kinase catalyzes auto-phosphorylation and triggers downstream signal transduction pathways.

Trk's are widely expressed in neuronal tissue during its development where Trk's are critical for the maintenance and survival of these cells. A post-embryonic role for the Trk/neurotrophin axis (or pathway), however, remains in question. There are reports showing that Trk's play important role in both development and function of the nervous system (Patapoutian, A. et al *Current Opinion in Neurobiology*, 2001, 11, 272-280).

In the past decade, a considerable number of literature documentations linking Trk signalling with cancer have published. For example, while Trk's are expressed at low levels outside the nervous system in the adult, Trk expression is increased in late stage prostate cancers. Both normal prostate tissue and androgen-dependent prostate tumours express low levels of Trk A and undetectable levels of Trk B and C. However, all isoforms of Trk receptors as well as their cognate ligands are up-regulated in late stage, androgen-independent prostate cancer. There is additional evidence that these late stage prostate cancer cells become dependent on the Trk/neurotrophin axis for their survival. Therefore, Trk inhibitors may yield a class of apoptosis-inducing agents specific for androgen-independent prostate cancer (Weeraratna, A. T. et al *The Prostate*, 2000, 45, I40-I48).

Furthermore, very recent literature also shows that over-expression, activation, amplification and/or mutation of Trk's are associated with secretory breast carcinoma (*Cancer Cell*, 2002, 2, 367-376), colorectal cancer (Bardelli et al *Science*, 2003, 300, 949-949) and ovarian cancer (Davidson, B. et al *Clinical Cancer Research*, 2003, 9, 2248-2259).

There are a few reports of selective Trk tyrosine kinase inhibitors. Cephalon described CEP-751, CEP-701 (George, D. et al *Cancer Research*, 1999, 59, 2395-2341) and other indolocarbazole analogues (WO0114380) as Trk inhibitors. It was shown that CEP-701 and/or CEP751, when combined with surgically or chemically induced androgen ablation, offered better efficacy compared with mono-therapy alone. GlaxoSmithKline disclosed certain oxindole compounds as Trk A inhibitors in WO0220479 and WO0220513. Recently, Japan Tobacco reported pyrazolyl condensed cyclic compounds as Trk inhibitors (JP2003231687A).

In addition to the above, Vertex Pharmaceuticals have described pyrazole compounds as inhibitors of GSK3, Aurora, etc. in WO0250065, WO0262789, WO03027111 and WO200437814; and AstraZeneca have reported pyrazole compounds as inhibitors against IGF-1 receptor kinase (WO0348133).

SUMMARY OF THE INVENTION

In accordance with the present invention, the applicants have hereby discovered novel pyrazole compounds, or pharmaceutically acceptable salts thereof, which possess Trk kinase inhibitory activity and are accordingly useful for their anti-proliferation and/or proapoptotic (such as anti-cancer) activity and in methods of treatment of the human or animal body. The invention also relates to processes for the manufacture of said pyrazole compounds, or pharmaceutically acceptable salts thereof, to pharmaceutical compositions containing them and to their use in the manufacture of medicaments for use in the production of an anti-proliferation and/or proapoptotic effect in warm-blooded animals such as man.

Also in accordance with the present invention the applicants provide methods of using such pyrazole compounds, or pharmaceutically acceptable salts thereof, in the treatment of cancer.

The properties of the compounds claimed in this invention are expected to be of value in the treatment of disease states associated with cell proliferation such as cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Furthermore, the compounds, or pharmaceutically acceptable salts thereof, of the invention are expected to be of value in the treatment or prophylaxis of cancers selected from congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposis sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma and leukaemia; particularly ovarian cancer, breast cancer, colorectal cancer, prostate cancer and lung cancer—NSCLC and SCLC; more particularly prostate cancer; and more particularly hormone refractory prostate cancer.

DETAILED DESCRIPTION OF THE INVENTION

Accordingly, the present invention provides a compound of formula (I):

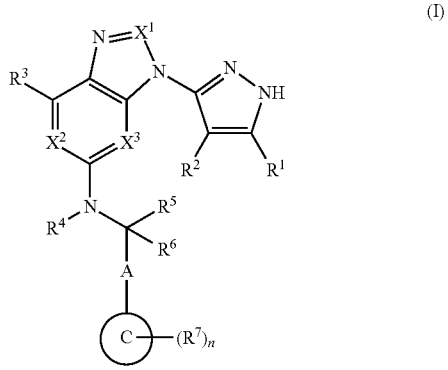

(I)

wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$-amino, $C_{1-6}$alkanoylamino, N-($C_{1-6}$alkyl)carbamoyl, N,N-($C_{1-6}$alkyl)$_2$-carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^8$; and wherein if said heterocyclyl contains an —NH— moiety that nitrogen may be optionally substituted by a group selected from $R^9$;

$X^1$, $X^2$ and $X^3$ are independently =N— or =CR$^{10}$—;

$R^3$ and $R^{10}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$-amino, $C_{1-6}$alkanoylamino, N-($C_{1-6}$alkyl)carbamoyl, N,N-($C_{1-6}$alkyl)$_2$-carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, carbocyclyl-$R^{11}$— or heterocyclyl-$R^{12}$—; wherein $R^3$ and $R^{10}$ independently of each other may be optionally substituted on carbon by one or more $R^{13}$; and wherein if said heterocyclyl contains an —NH— moiety that nitrogen may be optionally substituted by a group selected from $R^{14}$;

$R^4$ is hydrogen or optionally substituted $C_{1-6}$alkyl; wherein said optional substituents are selected from one or more $R^{15}$;

$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$-amino, $C_{1-6}$alkanoylamino, N-($C_{1-6}$alkyl)carbamoyl, N,N-($C_{1-6}$alkyl)$_2$-carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, carbocyclyl or heterocyclyl; wherein $R^5$ and $R^6$ independently of each other may be optionally substituted on carbon by one or more $R^{16}$; and wherein if said heterocyclyl contains an —NH— moiety that nitrogen may be optionally substituted by a group selected from $R^{17}$;

A is a direct bond or $C_{1-2}$alkylene; wherein said $C_{1-2}$alkylene may be optionally substituted by one or more $R^{18}$;

Ring C is carbocyclyl or heterocyclyl; wherein if said heterocyclyl contains an —NH-moiety that nitrogen may be optionally substituted by a group selected from $R^{19}$;

$R^7$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$-amino, $C_{1-6}$alkanoylamino, N-($C_{1-6}$alkyl)carbamoyl, N,N-($C_{1-6}$alkyl)$_2$-carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, carbocyclyl or heterocyclyl; wherein $R^7$ may be optionally substituted on carbon by one or more $R^{20}$; and wherein if said heterocyclyl contains an —NH— moiety that nitrogen may be optionally substituted by a group selected from $R^{21}$;

n is 0, 1, 2 or 3; wherein the values of $R^7$ may be the same or different;

$R^8$, $R^{13}$, $R^{15}$, $R^{16}$, $R^{18}$ and $R^{20}$ and are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$-amino, $C_{1-6}$alkanoylamino, N-($C_{1-6}$alkyl)carbamoyl, N,N-($C_{1-6}$alkyl)$_2$-carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, carbocyclyl-$R^{22}$— or heterocyclyl-$R^{23}$—; wherein $R^8$, $R^{13}$, $R^{15}$, $R^{16}$, $R^{18}$ and $R^{20}$ independently of each other may be optionally substituted on carbon by one or more $R^{24}$; and wherein if said heterocyclyl contains an —NH— moiety that nitrogen may be optionally substituted by a group selected from $R^{25}$;

$R^9$, $R^{14}$, $R^{17}$, $R^{19}$, $R^{21}$ and $R^{25}$ are independently selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)carbamoyl, benzyl, benzyloxycarbonyl, benzoyl and phenylsulphonyl; wherein $R^9$, $R^{14}$, $R^{17}$, $R^{19}$, $R^{21}$ and $R^{25}$ independently of each other may be optionally substituted on carbon by on or more $R^{26}$;

$R^{24}$ and $R^{26}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$-amino, $C_{1-6}$alkanoylamino, N-($C_{1-6}$alkyl)carbamoyl, N,N-($C_{1-6}$alkyl)$_2$-carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, carbocyclyl or heterocyclyl; wherein $R^{24}$ and $R^{26}$ independently of each other may be optionally substituted on carbon by one or more $R^{27}$; and wherein if said heterocyclyl contains an —NH-moiety that nitrogen may be optionally substituted by a group selected from $R^{28}$;

$R^{11}$, $R^{12}$, $R^{22}$ and $R^{23}$ are independently selected from a direct bond, —O—, —N($R^{29}$)—, —C(O)—, —N($R^{30}$)C(O)—, —C(O)N($R^{31}$)—, —S(O)$_s$—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$alkyl and s is 0-2;

$R^{27}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{28}$ is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)carbamoyl, benzyl, benzyloxycarbonyl, benzoyl and phenylsulphonyl;

or a pharmaceutically acceptable salt thereof.

Particular values of the variable groups contained in formula (I) are as follows. Such values may be used, where appropriate, with any of the definitions, claims or embodiments defined hereinbefore or hereinafter.

$R^1$ is selected from $C_{1-6}$alkyl, $C_{1-6}$alkoxy and carbocyclyl.

$R^1$ is selected from methyl, isopropoxy and cyclopropyl.

$R^2$ is hydrogen.

$R^1$ and $R^2$ are independently selected from hydrogen, $C_{1-6}$alkyl, $C_{1-6}$alkoxy and carbocyclyl.

$R^1$ and $R^2$ are independently selected from hydrogen, methyl, isopropoxy and cyclopropyl.

$X^1$ is $=CR^{10}-$ and $X^2$ and $X^3$ are independently selected from $-N=$.

$X^1$ and $X^2$ are independently selected from $=CR^{10}-$ and $X^3$ is $-N=$.

$X^1$ and $X^3$ are independently selected from $=CR^{10}-$ and $X^2$ is $-N=$.

$X^1$, $X^2$ and $X^3$ are independently selected from $=CR^{10}-$.

$X^1$, $X^2$ and $X^3$ are selected from $-N=$.

$R^3$ is selected from hydrogen, cyano, carbamoyl, $C_{1-6}$alkyl and $C_{1-6}$alkoxycarbonyl; wherein $R^3$ may be optionally substituted on carbon by one or more $R^{13}$;

$R^{13}$ is hydroxy.

$R^3$ is selected from hydrogen, cyano, carbamoyl, methyl and methoxycarbonyl; wherein $R^3$ may be optionally substituted on carbon by one or more $R^{13}$;

$R^{13}$ is hydroxy.

$R^3$ is selected from hydrogen and $C_{1-6}$alkyl wherein $R^3$ may be optionally substituted on carbon by one or more $R^{13}$; wherein:

$R^{13}$ is hydroxy.

$R^3$ is selected from hydrogen, cyano, carbamoyl, methyl, hydroxymethyl and methoxycarbonyl.

$R^3$ is selected from hydrogen, methyl and hydroxymethyl.

$R^3$ and $R^{10}$ are independently selected from hydrogen, halo, cyano, carbamoyl, $C_{1-6}$alkyl and $C_{1-6}$alkoxycarbonyl; wherein $R^3$ and $R^{10}$ independently of each other may be optionally substituted on carbon by one or more $R^{13}$;

$R^{13}$ is selected from hydroxy, amino and $C_{1-6}$alkanoylamino.

$R^3$ and $R^{10}$ are independently selected from hydrogen, fluoro, chloro, cyano, carbamoyl, methyl and ethoxycarbonyl; wherein $R^3$ and $R^{10}$ independently of each other may be optionally substituted on carbon by one or more $R^{13}$;

$R^{13}$ is selected from hydroxy, amino and acetylamino.

$R^3$ and $R^{10}$ are independently selected from hydrogen, halo, cyano, carbamoyl, $C_{1-6}$alkyl and $C_{1-6}$alkoxycarbonyl; wherein $R^3$ and $R^{10}$ independently of each other may be optionally substituted on carbon by one or more $R^3$; wherein:

$R^{13}$ is hydroxy.

$R^3$ and $R^{10}$ are independently selected from hydrogen, fluoro, chloro, cyano, carbamoyl, methyl, aminomethyl, acetylaminomethyl, hydroxymethyl and ethoxycarbonyl.

$R^3$ and $R^{10}$ are independently selected from hydrogen, fluoro, chloro, cyano, carbamoyl, methyl, hydroxymethyl and ethoxycarbonyl.

$R^{10}$ is selected from hydrogen, halo, cyano, carbamoyl and $C_{1-6}$alkyl; wherein $R^{10}$ may be optionally substituted on carbon by one or more $R^{13}$ $R^{13}$ is selected from amino and $C_{1-6}$alkanoylamino.

$R^{10}$ is selected from hydrogen, fluoro, chloro, cyano, carbamoyl and methyl; wherein $R^{10}$ may be optionally substituted on carbon by one or more $R^{13}$;

$R^{13}$ is selected from amino and acetylamino.

$R^{10}$ is selected from hydrogen, halo, cyano, carbamoyl and $C_{1-6}$alkoxycarbonyl.

$R^{10}$ is selected from hydrogen, fluoro, chloro, cyano, carbamoyl, methyl, aminomethyl and acetylaminomethyl.

$R^{10}$ is selected from hydrogen, fluoro, chloro, cyano, carbamoyl and ethoxycarbonyl.

$R^4$ is hydrogen.

$R^4$ is optionally substituted $C_{1-6}$alkyl; wherein said optional substituents are selected from one or more $R^{15}$.

$R^5$ and $R^6$ are independently selected from hydrogen or $C_{1-6}$alkyl; wherein $R^5$ and $R^6$ independently of each other may be optionally substituted on carbon by one or more $R^{16}$; wherein:

$R^{16}$ is hydroxy.

$R^5$ and $R^6$ are independently selected from hydrogen, methyl; ethyl or hydroxymethyl.

$R^5$ and $R^6$ are independently selected from hydrogen, methyl or hydroxymethyl.

$R^5$ is selected from hydrogen, methyl, ethyl or hydroxymethyl.

$R^5$ is selected from hydrogen, methyl or hydroxymethyl.

$R^6$ is selected from hydrogen or hydroxymethyl.

$R^6$ is hydrogen.

A is a direct bond.

A is $C_{1-2}$alkylene; wherein said $C_{1-2}$alkylene may be optionally substituted by one or more $R^{18}$.

A is a direct bond or $C_{1-2}$alkylene; wherein said $C_{1-2}$alkylene may be optionally substituted by one or more $R^{18}$; wherein $R^{18}$ is hydroxy.

A is a direct bond or methylene; wherein said $C_{1-2}$alkylene may be optionally substituted by one or more $R^{18}$; wherein $R^{18}$ is hydroxy.

A is a direct bond, methylene or hydroxymethylene.

Ring C is heterocyclyl; wherein if said heterocyclyl contains an —NH— moiety that nitrogen may be optionally substituted by a group selected from $R^{19}$.

Ring C is carbocyclyl.

Ring C is carbocyclyl or heterocyclyl.

Ring C is phenyl, pyridyl, pyrimidinyl, 1,3-benzodioxolyl or 1H-indolyl.

Ring C is phenyl, pyridyl, 1,3-benzodioxolyl or 1H-indolyl.

Ring C is phenyl, pyrid-2-yl, pyrimidin-2-yl, 1,3-benzodioxol-5-yl or 1H-indol-3-yl.

Ring C is phenyl, pyrid-2-yl, 1,3-benzodioxol-5-yl or 1H-indol-3-yl.

Ring C is phenyl.

Ring C is pyridyl.

Ring C is pyrid-2-yl.

Ring C is pyrimidinyl.

Ring C is pyrimidin-2-yl.

$R^7$ is selected from halo and $C_{1-6}$alkyl; wherein $R^7$ may be optionally substituted on carbon by one or more $R^{20}$; wherein $R^{20}$ is halo.

$R^7$ is selected from fluoro and methyl; wherein $R^7$ may be optionally substituted on carbon by one or more $R^{20}$; wherein $R^{20}$ is fluoro.

$R^7$ is halo.

$R^7$ is trifluoromethyl and fluoro.

$R^7$ is fluoro.

n is 0, 1 or 2; wherein the values of $R^7$ may be the same or different.

n is 0 or 1.

n is 1.

Ring C, $R^7$ and n together form 4-fluorophenyl, 5-fluoropyrid-2-yl or 5-fluoropyrimidin-2-yl.

Ring C, $R^7$ and n together form 4-fluorophenyl.

Ring C, $R^7$ and n together form 5-fluoropyrid-2-yl.

Ring C, $R^7$ and n together form 5-fluoropyrimidin-2-yl.

Therefore in a further aspect of the invention there is provided a compound of formula (I) (as depicted herein above) wherein:

$R^1$ and $R^2$ are independently selected from hydrogen, $C_{1-6}$alkyl, $C_{1-6}$alkoxy and carbocyclyl;

$X^1$, $X^2$ and $X^3$ are independently =N— or =$CR^{10}$—;

$R^3$ and $R^{10}$ are independently selected from hydrogen, halo, cyano, carbamoyl, $C_{1-6}$alkyl and $C_{1-6}$alkoxycarbonyl; wherein $R^3$ and $R^{10}$ independently of each other may be optionally substituted on carbon by one or more $R^{13}$;

$R^4$ is hydrogen;

$R^5$ and $R^6$ are independently selected from hydrogen or $C_{1-6}$alkyl; wherein $R^5$ and $R^6$ independently of each other may be optionally substituted on carbon by one or more $R^{16}$;

A is a direct bond or $C_{1-2}$alkylene; wherein said $C_{1-2}$alkylene may be optionally substituted by one or more $R^{18}$;

Ring C is carbocyclyl or heterocyclyl;

$R^7$ is selected from halo and $C_{1-6}$alkyl; wherein $R^7$ may be optionally substituted on carbon by one or more $R^{20}$;

n is 0, 1 or 2; wherein the values of $R^7$ may be the same or different;

$R^{13}$ is selected from hydroxy, amino and $C_{1-6}$alkanoylamino;

$R^{16}$ is hydroxy;

$R^{18}$ is hydroxy;

$R^{20}$ is halo;

or a pharmaceutically acceptable salt thereof.

Therefore in a further aspect of the invention there is provided a compound of formula (I) (as depicted herein above) wherein:

$R^1$ and $R^2$ are independently selected from hydrogen, $C_{1-6}$alkyl, $C_{1-6}$alkoxy and carbocyclyl;

$X^1$, $X^2$ and $X^3$ are independently =N— or =$CR^{10}$—;

$R^3$ and $R^{10}$ are independently selected from hydrogen, halo, cyano, carbamoyl, $C_{1-6}$alkyl and $C_{1-6}$alkoxycarbonyl; wherein $R^3$ and $R^{10}$ independently of each other may be optionally substituted on carbon by one or more $R^{13}$;

$R^4$ is hydrogen;

$R^5$ and $R^6$ are independently selected from hydrogen or $C_{1-6}$alkyl; wherein $R^5$ and $R^6$ independently of each other may be optionally substituted on carbon by one or more $R^{16}$;

A is a direct bond;

Ring C is carbocyclyl;

$R^7$ is halo;

n is 1;

$R^{13}$ is hydroxy; and $R^{16}$ is hydroxy;

or a pharmaceutically acceptable salt thereof.

Therefore in a further aspect of the invention there is provided a compound of formula (I) (as depicted herein above) wherein:

$R^1$ is selected from methyl, isopropoxy and cyclopropyl;

$R^2$ is hydrogen;

$X^1$, $X^2$ and $X^3$ are independently =N— or =$CR^{10}$—;

$R^3$ is selected from hydrogen, cyano, carbamoyl, methyl, hydroxymethyl and methoxycarbonyl;

$R^{10}$ is selected from hydrogen, fluoro, chloro, cyano, carbamoyl, methyl, aminomethyl and acetylaminomethyl;

$R^4$ is hydrogen;

$R^5$ is selected from hydrogen, methyl, ethyl or hydroxymethyl;

$R^6$ is selected from hydrogen or hydroxymethyl;

A is a direct bond, methylene or hydroxymethylene;

Ring C is phenyl, pyrid-2-yl, 1,3-benzodioxol-5-yl or 1H-indol-3-yl;

$R^7$ is trifluoromethyl and fluoro;

n is 0, 1 or 2; wherein the values of $R^7$ may be the same or different;

or a pharmaceutically acceptable salt thereof.

Therefore in a further aspect of the invention there is provided a compound of formula (I) (as depicted herein above) wherein:

$R^1$ is selected from methyl, isopropoxy and cyclopropyl;

$R^2$ is hydrogen;

$X^1$, $X^2$ and $X^3$ are independently =N— or =$CR^{10}$—;

$R^3$ is selected from hydrogen, methyl and hydroxymethyl;

$R^4$ is hydrogen;

$R^5$ is selected from hydrogen, methyl or hydroxymethyl;

$R^6$ is selected from hydrogen or hydroxymethyl;

A is a direct bond;

Ring C is phenyl;

$R^7$ is fluoro;

n is 1; and $R^{10}$ is selected from hydrogen, fluoro, chloro, cyano, carbamoyl and ethoxycarbonyl;

or a pharmaceutically acceptable salt thereof.

In another aspect of the invention, preferred compounds of the invention are any one of the Examples or a pharmaceutically acceptable salt thereof.

In a further aspect of the invention there is provided Examples 1, 3, 8, 13, 21, 22, 23, 24, 27 or 43 or a pharmaceutically acceptable salt thereof.

In an additional embodiment the present invention provides a compound of formula (I), or a pharmaceutically acceptable salt thereof, for use as a medicament.

In an additional embodiment the present invention provides a compound of formula (I), or a pharmaceutically acceptable salt thereof, for use in the manufacture of a medicament for use in the inhibition of Trk activity.

In an additional embodiment the present invention provides a compound of formula (I), or a pharmaceutically acceptable salt thereof, for use in the manufacture of a medicament for use in the treatment or prophylaxis of cancer.

In an additional embodiment the present invention provides a compound of the formula (I), or a pharmaceutically acceptable salt thereof, for use in the manufacture of a medicament for use in the treatment of cancer in a warm-blooded animal such as man.

In an additional embodiment the present invention provides a compound of the formula (I), or a pharmaceutically acceptable salt thereof, for use in the manufacture of a medicament for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the manufacture of a medicament for use in the production of an anti-proliferative effect.

In an additional embodiment the present invention provides a method of inhibiting Trk activity comprising administering to a host in need of such treatment a therapeutically effective amount of a compound of formula (I), or a pharmaceutically acceptable salt thereof.

In an additional embodiment the present invention provides a method for the treatment of cancer comprising administering to a host in need of such treatment a therapeutically effective amount of a compound of formula (I), or a pharmaceutically acceptable salt thereof.

In an additional embodiment the present invention provides a method for the treatment or prophylaxis of cancer comprising administering a therapeutically effective amount of a compound of formula (I) or a pharmaceutically acceptable salt thereof.

In an additional embodiment the present invention provides a method for the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man comprising administering a therapeutically effective amount of a compound of formula (I) or a pharmaceutically acceptable salt thereof.

In an additional embodiment the present invention provides a method of producing an anti-proliferative effect in a warm-blooded animal, such as man, in need of such treatment which comprises administering to said animal an effective amount of a compound of formula (I), or a pharmaceutically acceptable salt thereof.

In an additional embodiment the present invention provides a pharmaceutical composition comprising a compound of formula (I), or a pharmaceutically acceptable salt thereof, together with at least one pharmaceutically acceptable carrier, diluent or excipient.

In an additional embodiment the present invention provides a pharmaceutical composition comprising a compound of formula (I), or a pharmaceutically acceptable salt thereof, together with at least one pharmaceutically acceptable carrier, diluent or excipient for use in the inhibition of Trk activity.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In an additional embodiment the present invention provides a pharmaceutical composition comprising a compound of formula (I), or a pharmaceutically acceptable salt thereof, together with at least one pharmaceutically acceptable carrier, diluent or excipient for use in the production of an anti-proliferative effect in a warm-blooded animal such as man.

In an additional embodiment the present invention provides a compound of formula (I), or a pharmaceutically acceptable salt thereof, for use in the inhibition of Trk activity.

In an additional embodiment the present invention provides a compound of formula (I), or a pharmaceutically acceptable salt thereof, for use in the treatment or prophylaxis of cancer.

In an additional embodiment the present invention provides a compound of the formula (I), or a pharmaceutically acceptable salt thereof, for use in the treatment of cancer in a warm-blooded animal such as man.

In an additional embodiment the present invention provides a compound of the formula (I), or a pharmaceutically acceptable salt thereof, for use in the treatment or prophylaxis of cancers (solid tumours and leukaemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the production of an anti-proliferative effect.

In one embodiment where the inhibition of Trk activity is referred to particularly this refers to the inhibition of Trk A activity.

In another embodiment where the inhibition of Trk activity is referred to particularly this refers to the inhibition of Trk B activity.

Where the treatment (or prophylaxis) of cancer is referred to, particularly it refers to the treatment (or prophylaxis) of congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposis sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma, leukaemia, tumours of the central and peripheral nervous system, melanoma, fibrosarcoma including congenital fibrosarcoma and osteosarcoma. More particularly it refers to prostate cancer. In addition, more particularly it refers to SCLC, NSCLC, colorectal cancer, ovarian cancer and/or breast cancer. In a further aspect it refers to hormone refractory prostate cancer.

In a further aspect of the present invention provides a process for preparing a compound of formula (I) or a pharmaceutically acceptable salt thereof which process (wherein variable groups are, unless otherwise specified, as defined in formula (I)) comprises of:

Process a) reaction of a compound of formula (II):

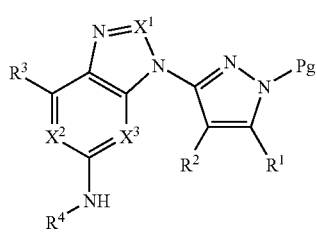

(II)

wherein Pg is a nitrogen protecting group; with a compound of formula (III):

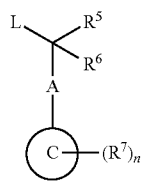

(III)

wherein L is a displaceable group;

Process b) for compounds of formula (I) wherein $R^5$ is hydroxymethyl and $R^6$ is hydrogen; reaction of a compound of formula (II) with an epoxide of formula (IV):

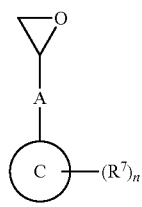

(IV)

Process c) for compounds of formula (I) wherein $X^1$ is $=CR^{10}$—; reacting a compound of formula (V):

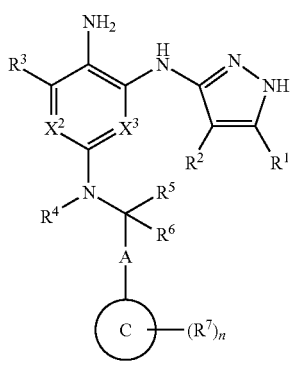

(V)

with a compound of formula (VI):

(VII)

Process d) for compounds of formula (I) wherein $X^1$ is $=N$—; reacting a compound of formula (V) with aqueous $NaNO_2$ solution;

Process e) reacting a compound of formula (VII):

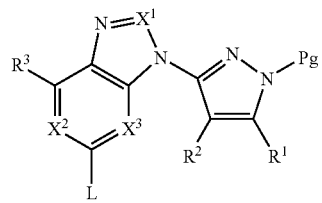

(VII)

wherein L is a displaceable group and Pg is a nitrogen protecting group; with an amine of formula (VIII):

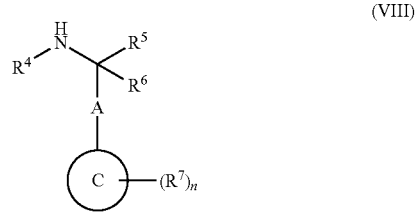

(VIII)

and thereafter if necessary:

i) converting a compound of the formula (I) into another compound of the formula (I);

ii) removing any protecting groups;

iii) forming a pharmaceutically acceptable salt.

L is a displaceable group, suitable values for L are for example, a halo or sulphonyloxy group, for example a chloro, bromo, methanesulphonyloxy or toluene-4-sulphonyloxy group.

Pg is a nitrogen protecting group. Suitable values for Pg are described herein below.

Specific reaction conditions for the above reactions are as follows.

Process a) Compounds of formula (II) and (III) may be reacted together under standard nucleophilic addition reactions for example in the presence of a suitable base such as potassium carbonate and a suitable solvent such as DMF and at a temperature in the range from 25 to 100° C.

Compounds of the formula (II) may be prepared according to Scheme 1:

Scheme 1

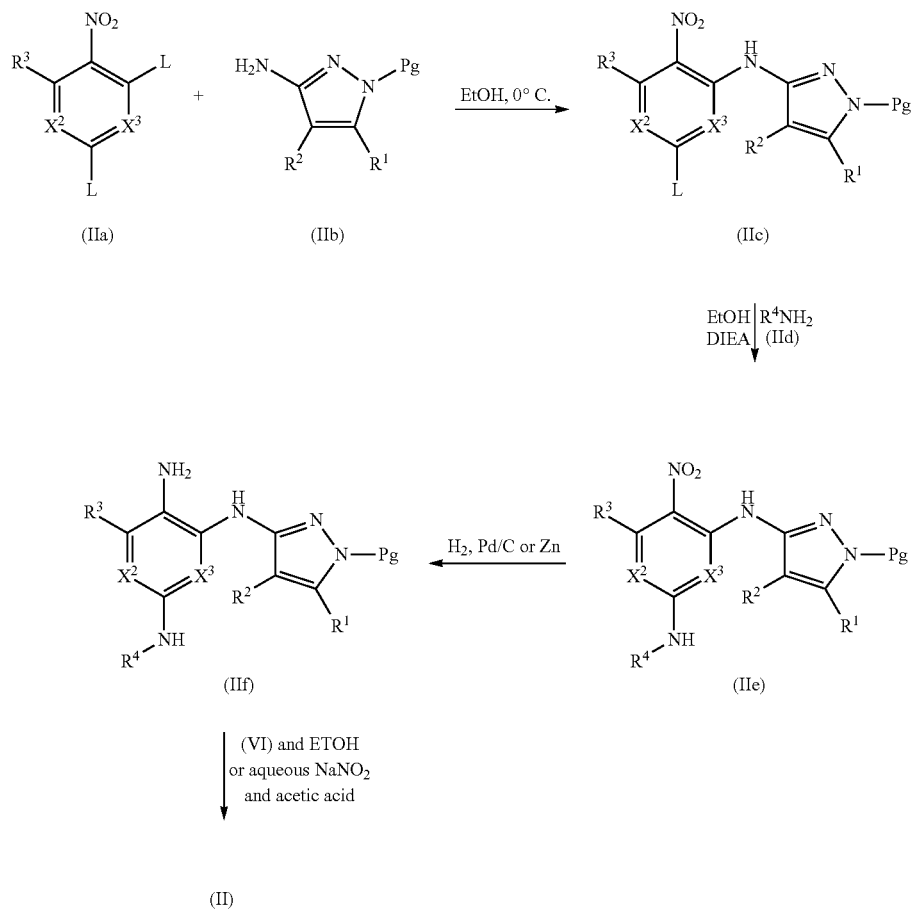

Compounds of formula (III), (IIa), (IIb) and (IId) are commercially available compounds, or they are known in the literature, or they are prepared by standard processes known in the art.

Process b) Compounds of formula (II) and (IV) may be reacted together under epoxide ring opening reaction conditions for example in the presence of a suitable catalyst such as $LiClO_4$, $NaClO_4$, $Mg(ClO_4)_2$ and a suitable solvent such as $CH_3CN$ and at a temperature in the range from 25 to 80° C.

Compounds of formula (IV) are commercially available compounds, or they are known in the literature, or they are prepared by standard processes known in the art.

Process c) Compounds of formula (V) and compounds of formula (VI) may be reacted together in a suitable solvent such as ethanol at reflux temperature.

Compounds (V) may be prepared according to Scheme 2:

Scheme 2

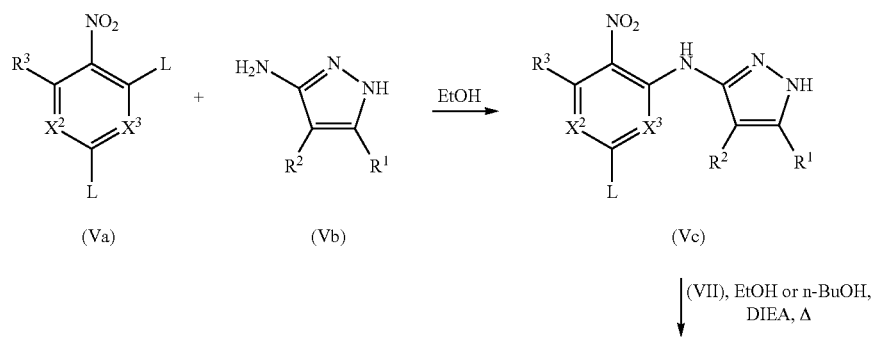

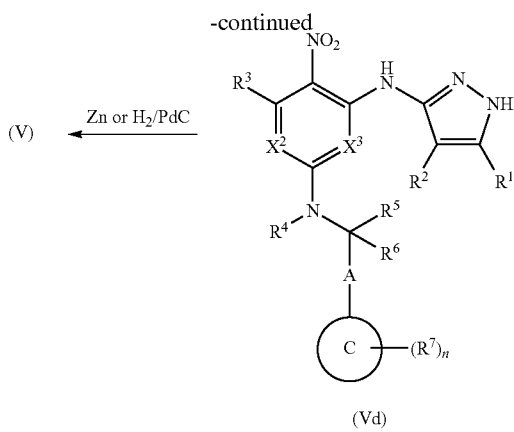

(Vd)

Compounds of formula (Va), (Vb) and (VI) are commercially available compounds, or they are known in the literature, or they are prepared by standard processes known in the art.

Process d) Compounds of formula (V) and an aqueous NaNO₂ solution may be reacted together in aqueous acetic acid.

Process e) Compounds of formula (VII) and (VIII) may be reacted together under the conditions listed in Process a).

Compounds of formula (VII) may be prepared according to Scheme 3:

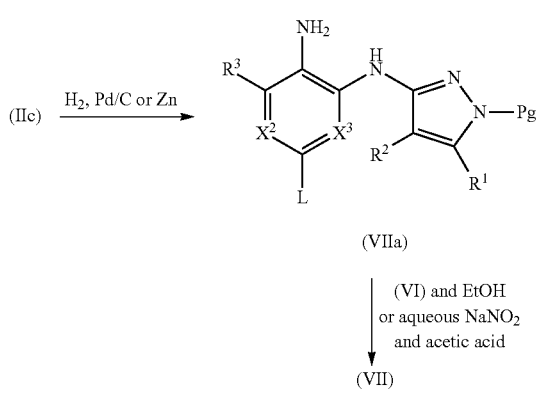

Compounds of the formula (VIII) are commercially available compounds, or they are known in the literature, or they are prepared by standard processes known in the art.

Certain intermediates disclosed herein are novel as such they are provided as a further feature of the invention.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Definitions

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. However, references to individual alkyl groups such as 'propyl' are specific for the straight-chained version only and references to individual branched chain alkyl groups such as 'isopropyl' are specific for the branched-chain version only. A similar convention applies to other radicals. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$-group can optionally be replaced by a —C(O)—, and a ring sulphur atom may be optionally oxidised to form the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Further examples and suitable values of the term "heterocyclyl" are morpholino, piperazinyl and pyrrolidinyl. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$-group can optionally be replaced by a —C(O)— and a ring sulphur atom may be optionally oxidised to form the S-oxides.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

The term "$C_{m-n}$" or "$C_{m-n}$ group" used alone or as a prefix, refers to any group having m to n carbon atoms.

The term "optionally substituted" refers to either groups, structures, or molecules that are substituted and those that are not substituted.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkoxyimino" include $C_{1-4}$alkoxyimino, $C_{1-3}$alkoxyimino, methoxyimino, ethoxyimino and propoxyimino. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$allkylthio" include methylthio and ethylthio. Examples of "$C_{1-6}$alkylsulphonylamino" include methylsulphonylamino and ethylsulphsulphonylamino. Examples of "$C_{1-6}$alkanoyl" include $C_{1-4}$alkanoyl, propionyl and acetyl. Examples of "N-($C_{1-6}$alkyl)amino" include methylamino and ethylamino. Examples of "N,N-($C_{1-6}$alkyl)$_2$-amino" include di-N-methylamino, di-(N-ethyl) amino and N-ethyl-N-methylamino. Examples of "$C_{2-6}$alkenyl" are vinyl, allyl and 1-propenyl. Examples of "$C_{2-6}$alkynyl" are ethynyl, 1-propynyl and 2-propynyl. Examples of "N-($C_{1-6}$alkyl)sulphamoyl" are N-(methyl)sulphamoyl and N-(ethyl)sulphamoyl. Examples of "N-($C_{1-6}$alkyl)$_2$sulphamoyl" are N,N-(dimethyl)sulphamoyl and N-(methyl)-N-(ethyl)sulphamoyl. Examples of "N-($C_{1-6}$alkyl)carbamoyl" are N-($C_{1-4}$alkyl)carbamoyl, methylaminocarbonyl and ethylaminocarbonyl. Examples of "N,N-($C_{1-6}$alkyl)$_2$-carbamoyl" are N,N-($C_{1-4}$alkyl)$_2$-carbamoyl, dimethylaminocarbonyl and methylethylaminocarbonyl.

"RT" or "rt" means room temperature.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It should be noted that the compounds claimed in this invention are capable of existing in different resonance structures and thus the compounds claimed herein include all possible resonance structures, for example optical isomers, diastereoisomers and geometric isomers and all tautomeric forms of the compounds of the formula (I).

It is also to be understood that certain compounds of the formula (I) can exist in solvated as well as unsolvated forms such as, for example, hydrated forms. It is to be understood that the invention encompasses all such solvated forms.

Formulations

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of cancer is an amount sufficient to symptomatically relieve in a warm-blooded animal, particularly a human the symptoms of cancer, to slow the progression of cancer, or to reduce in patients with symptoms of cancer the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substance, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as
N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and
6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies; and (x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

Synthesis

The compounds, or pharmaceutically acceptable salts thereof, of the present invention can be prepared in a number of ways well known to one skilled in the art of organic synthesis. The compounds, or pharmaceutically acceptable salts thereof, of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds, or pharmaceutically acceptable salts thereof, of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate; evaporation of organic solvent was carried out using a rotary evaporator under reduced pressure (4.5-30 mmHg) with a bath temperature of up to 60° C.;

23

(iii) chromatography means flash chromatography on silica gel; thin layer chromatography (TLC) was carried out on silica gel plates;
(iv) in general, the course of reactions was followed by TLC or liquid chromatography/mass spectroscopy (LC/MS) and reaction times are given for illustration only;
(v) final products have satisfactory proton nuclear magnetic resonance (NMR) spectra and/or mass spectra data;
(vi) yields are given for illustration only and are not necessarily those which can be obtained by diligent process development; preparations were repeated if more material was required;
(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;
(viii) chemical symbols have their usual meanings;
(ix) solvent ratio was given in volume:volume (v/v) terms.
(x) the following abbreviations have been used:
EtOAc ethyl acetate;
EtOH ethanol;
THF tetrahydrofuran;
DIEA diisopropylethylamine
MeOH methanol; and
DCM dichloromethane.

24

Example 1

(2R)-2-[9-(5-Cyclopropyl-1H-pyrazol-3-yl)-6-methyl-9H-purin-2-ylamino]-2-(4-fluorophenyl)ethanol A mixture of (R)-2-[5-amino-4-(5-cyclopropyl-1H-pyrazol-3-ylamino)-6-methylpyrimidin-2-ylamino]-2-(4-fluorophenyl)ethanol (Method 40; 0.3 g, 0.8 mmol) and formamidine acetate (0.2 g, 1.6 mmol) in EtOH (8 ml) was heated to reflux for 12 hours. The reaction was then concentrated, dissolved in DCM (50 ml), and washed with saturated NaHCO$_3$ solution (50 ml). The organic layer was then dried, filtered, and concentrated. The resulting solid was purified by column chromatography (DCM:MeOH=20:1) to give the title compound (0.11 g, 35%). NMR (400 MHz, CD$_3$OD) 8.32 (s, 1H), 7.46-7.43 (m, 2H), 7.06-7.02 (m, 2H), 6.24 (s, 1H), 5.10-5.02 (m, 1H), 3.87-3.75 (m, 2H), 2.61 (s, 3H), 1.99-1.96 (m, 1H), 1.10-1.08 (m, 2H), 0.80-0.75 (m, 2H). MS: Calcd.: 393; Found: [M+H]$^+$ 394.

Examples 2-8

Following a similar procedure to Example 1, the following compounds were synthesized from a suitable amino-pyrimidine by treatment with formamidine acetate (or acetamidine hydrochloride for Example 6).

| Ex | Compound | NMR | SM |
|---|---|---|---|
| 2 | 9-(5-Cyclopropyl-1H-pyrazol-3-yl)-N-[(1S)-1-(4-fluorophenyl)ethyl]-9H-purin-2-amine | 0.77 (m, 2H), 1.02 (m, 2H), 1.42 (m, 3H), 1.98 (m, 1H), 5.04 (br s, 1H), 6.30 (m, 1H), 7.09 (m, 2H), 7.43 (m, 2H), 7.85 (br s, 1H), 8.38 (s, 1H), 8.68 (s, 1H), 12.73 (s, 1H) | Method 41 |
| 3 | (2R)-2-{[9-(5-Cyclopropyl-1H-pyrazol-3-yl)-9H-purin-2-yl]amino}-2-(4-fluorophenyl)ethanol | 0.77 (m, 2H), 1.04 (m, 2H), 1.99 (m, 1H), 3.63 (m, 2H), 4.91 (m, 1H), 6.20 (m, 1H), 7.09 (m, 2H), 7.43 (m, 2H), 7.60 (br s, 1H), 8.38 (s, 1H), 8.68 (s, 1H), 12.73 (s, 1H) | Method 42 |
| 4 | 9-(5-Cyclopropyl-1H-pyrazol-3-yl)-N-(4-fluorobenzyl)-9H-purin-2-amine | 0.71 (m, 2H), 0.99 (m, 2H), 1.96 (m, 1H), 4.50 (m, 2H), 6.34 (m, 1H), 7.09 (m, 2H), 7.39 (m, 2H), 7.88 (br s, 1H), 8.39 (s, 1H), 8.70 (s, 1H), 12.74 (s, 1H) | Method 43 |
| 5 | 9-(5-Cyclopropyl-1H-pyrazol-3-yl)-N-[(1R)-1-(4-fluorophenyl)ethyl]-9H-purin-2-amine | 0.75 (m, 2H), 1.02 (m, 2H), 1.42 (m, 3H), 1.98 (m, 1H), 5.04 (br s, 1H), 6.28 (m, 1H), 7.09 (m, 2H), 7.44 (m, 2H), 7.85 (br s, 1H), 8.37 (s, 1H), 8.67 (s, 1H), 12.73 (s, 1H) | Method 44 |
| 6 | 9-(5-Cyclopropyl-1H-pyrazol-3-yl)-N-[(1S)-1-(4-fluorophenyl)ethyl]-8-methyl-9H-purin-2-amine | (CDCl$_3$): 0.71 (m, 2H), 0.95 (m, 2H), 1.45 (m, 3H), 1.86 (m, 1H), 2.60 (s, 3H), 5.07 (m, 1H), 5.80 (br s, 1H), 6.05 (s, 1H), 6.90 (m, 2H), 7.30 (m, 2H), 8.59 (s, 1H), 11.74 (br s, 1H) | Method 41 |
| 7 | (2R)-2-(4-Fluorophenyl)-2-(9-(5-methyl-1H-pyrazol-3-yl)-9H-purin-2-ylamino)ethanol | (400 MHz) 12.68 (s, 1H), 8.70 (s, 1H), 8.40 (s, 1H), 7.61 (b, 1H), 7.46 (m, 2H), 7.12 (m, 2H), 6.38 (b, 1H), 4.93 (m, 2H), 3.65 (m, 2H), 2.34 (s, 3H). MS: Calcd.: 353; Found: [M + H]$^+$ 354. | Method 45 |
| 8 | N-((S)-1-(4-Fluorophenyl)ethyl)-9-(5-isopropoxy-1H-pyrazol-3-yl)-9H-purin-2-amine | (400 MHz) 12.57 (s, 1H), 8.70 (s, 1H), 8.39 (s, 1H), 7.92 (b, 1H), 7.44 (m, 2H), 7.09 (m, 2H), 6.05 (b, 1H), 5.10 (b, 1H), 4.53 (m, 1H), 1.46 (d, J=6.8 Hz, 3H), 1.40 and 1.35 (d, J=6.0 Hz, 6H). MS: Calcd.: 381; Found: [M + H]$^+$ 382. | Method 46 |

Example 9

(2R)-2-[3-(5-Cyclopropyl-1H-pyrazol-3-yl)-7-methyl-3H-[1,2,3]triazolo[4,5-d]pyrimidin-5-ylamino]-2-(4-fluorophenylyl)ethanol To a solution of (R)-2-[5-amino-4-(5-cyclopropyl-1H-pyrazol-3-ylamino)-6-methylpyrimidin-2-ylamino]-2-(4-fluorophenyl)ethanol (Method 40; 0.18 g, 0.47 mmol) in aqueous acetic acid (5%, 3 ml) was added dropwise the aqueous solution of $NaNO_2$ (0.032 g, 0.47 mmol, 1 ml $H_2O$) at 25° C. The reaction was allowed to stir for an additional 5 minutes, treated with water (10 ml), and extracted with DCM (3×25 ml). The organic layer was washed with saturated $NaHCO_3$ solution (50 ml), dried, filtered, and concentrated. The resulting solid was purified by column chromatography (DCM:MeOH=30:1) to give the title compound (0.15 g, 81%). NMR (400 MHz, $CD_3OD$) 7.46-7.42 (m, 2H), 7.06-7.01 (m, 2H), 6.21 (s, 1H), 5.14-5.06 (m, 1H), 3.86-3.79 (m, 2H), 2.74 (s, 3H), 2.03-2.01 (m, 1H), 1.11-1.08 (m, 2H), 0.83-0.79 (m, 2H). MS: Calcd.: 394; Found: [M+H]$^+$ 395.

Example 10

3-(5-Cyclopropyl-1H-pyrazol-3-yl)-N-[(S)-1-(4-fluorophenyl)ethyl]-3H-[1,2,3]triazolo[4,5-d]pyrimidin-5-amine To a solution of (S)-$N^4$-(5-cyclopropyl-1H-pyrazol-3-yl)-$N^2$-[1-(4-fluorophenyl)ethyl]pyrimidine-2,4,5-triamine (Method 8; 0.04 g, 0.1 mmol) in aqueous acetic acid (5%, 3 ml) was slowly added an aqueous $NaNO_2$ solution (0.008 g, 0.1 mmol, 1 ml $H_2O$). The reaction was allowed to stir for an additional 5 minutes, treated with water (10 ml), and extracted with DCM (3×25 ml). The combined organic layer was washed with saturated $NaHCO_3$ solution (50 ml), dried, filtered, and concentrated. The resulting solid was purified by column chromatography (DCM:MeOH=15:1) to give the title compound (0.015 g, 40%). NMR (400 MHz, $CD_3OD$) 9.05 (s, 1H), 7.44-7.41 (m, 2H), 7.03-6.99 (m, 2H), 6.23 (s, 1H), 5.16-5.07 (m, 1H), 2.03-2.00 (m, 1H), 1.55 (d, J=6.8 Hz, 3H), 1.11-1.09 (m, 2H), 0.85-0.80 (m, 2H). MS: Calcd.: 364; Found: [M+H]$^+$ 365.

Example 11

Ethyl 9-(5-cyclopropyl-1H-pyrazol-3-yl)-2-[(S)-1-(4-fluorophenyl)ethylamino]-9H-purine-6-carboxylate A mixture of (S)-ethyl 5-amino-6-(5-cyclopropyl-1H-pyrazol-3-ylamino)-2-[1-(4-fluorophenyl)ethylamino]pyrimidine-4-carboxylate (Method 47; 0.6 g, 1.4 mmol) and formamidine acetate (0.32 g, 3.1 mmol) in EtOH (20 ml) was heated to reflux for 12 hours. The reaction was then concentrated, and the resulting residue was dissolved in EtOAc (50 ml) and washed with saturated $NaHCO_3$ solution (50 ml). The organic layer was dried, filtered, and concentrated. The resulting solid was purified by column chromatography (DCM: MeOH=20:1) to give the title compound (0.058 g, 8%). NMR (400 MHz, $CD_3OD$) 8.48 (s, 1H), 7.45-7.41 (m, 2H), 7.03-6.99 (m, 2H), 6.25 (s, 1H), 5.12-5.03 (m, 1H), 4.50 (q, J=7.2 Hz, 2H), 2.00-1.96 (m, 1H), 1.54 (d, J=7.0 Hz, 3H), 1.44 (t, J=7.2 Hz, 3H), 1.10-1.08 (m, 2H), 0.81-0.74 (m, 2H). MS: Calcd.: 435; Found: [M+H]$^+$ 436.

Example 12

[9-(5-Cyclopropyl-1H-pyrazol-3-yl)-2-[(S)-1-(4-fluorophenyl)ethylamino]-9H-purin-6-yl]methanol A solution of ethyl 9-(5-cyclopropyl-1H-pyrazol-3-yl)-2-[(S)-1-(4-fluorophenyl)ethylamino]-9H-purine-6-carboxylate (Example 11; 0.03 g, 0.069 mmol) in THF (3 ml) was cooled to 0° C. To which was slowly added lithium aluminium hydride (1.0 M in THF, 0.076 ml, 1.1 eq.). The reaction mixture was stirred at 0° C. for 30 minutes, at which point sodium sulfate decahydrate was added until bubbling stopped. The reaction was then filtered through a plug of celite, washed with THF (3×30 ml), and concentrated. The resulting residue was purified by column chromatography (DCM:MeOH=15:1) to give the title compound (0.09 g, 33%). NMR (400 MHz, $CDCl_3$) 8.27 (s, 1H), 7.39-7.36 (m, 2H), 7.03-6.98 (m, 2H), 6.32 (s, 1H), 5.65-5.64 (m, 1H), 5.10-5.07 (m, 1H), 5.03 (s, 2H), 3.87-3.85 (m, 1H), 1.93-1.88 (m, 1H), 1.57 (d, J=6.8 Hz, 3H), 1.08-1.06 (m, 2H), 0.81-0.77 (m, 2H). MS: Calcd.: 393; Found: [M+H]$^+$ 394.

Example 13

3-(5-Cyclopropyl-1H-pyrazol-3-yl)-N-[(S)-1-(4-fluorophenyl)ethyl]-3H-imidazo[4,5-b]pyridin-5-amine A mixture of (S)-$N^2$-(5-cyclopropyl-1H-pyrazol-3-yl)-$N^6$-[1-(4-fluorophenyl)ethyl]pyridine-2,3,6-triamine (Method 48; 0.240 g, 0.68 mmol) and formamidine acetate (0.113 g, 1.09 mmol) in EtOH (5 ml) was heated at reflux for 2 hours. After cooling to 25° C., the reaction mixture was treated with saturated $NaHCO_3$ solution (10 ml) and EtOAc (30 ml). The organic layer was separated, washed with brine (10 ml), and dried over $Na_2SO_4$. The solvent was removed under reduced pressure and the residue was purified by column chromatography (hexane:EtOAc=1:3) to give the title compound as an off-white solid (0.144 g, 58%). NMR (400 MHz) 12.57 (s, 1H), 8.25 (s, 1H), 7.72 (d, J=8.4 Hz, 1H), 7.41 (m, 2H), 7.32 (d, J=6.4 Hz, 1H), 7.10 (m 2H), 6.56 (d, J=8.8 Hz, 1H), 6.26 (s, 1H), 4.99 (m, 1H), 1.97 (m, 1H), 1.45 (d, J=6.8 Hz, 3H), 1.04 (m, 2H), 0.78-0.69 (m, 2H). MS: Calcd.: 362; Found: [M+H]$^+$ 363.

Examples 14-26

Following a similar procedure to Example 13, the following compounds were synthesized from a suitable amino-pyridine followed by treatment with formamidine acetate.

| Ex. | Compound | NMR/MS | SM |
| --- | --- | --- | --- |
| 14 | N-(4-Fluorobenzyl)-3-(5-cyclopropyl-1H-pyrazol-3-yl)-3H-imidazo[4,5-b]pyridin-5-amine | NMR (400 MHz) 12.59 (s, 1H), 8.27 (s, 1H), 7.74 (d, J=8.4 Hz, 1H), 7.40 (m, 2H), 7.13 (m, 2H), 6.54 (d, J=8.8 Hz, 1H), 6.36 (s, 1H), 4.50 (d, J=5.6 Hz, 2H), 1.95 (m, 1H), 1.00 (m, 2H), 0.68 (m, 2H). MS: Calcd.: 348; Found: [M + H]$^+$ 349. | Method 49 |

-continued

| Ex. | Compound | NMR/MS | SM |
|---|---|---|---|
| 15 | (2R)-2-[3-(5-Cyclopropyl-1H-pyrazol-3-yl)-3H-imidazo[4,5-b]pyridin-5-ylamino]-2-(4-fluorophenyl)ethanol | (400 MHz) 12.58 (s, 1H), 8.26 (s, 1H), 7.72 (d, J=8.8 Hz, 1H), 7.43 (m, 2H), 7.24 (d, J=6.4 Hz, 1H), 7.09 (m, 2H), 6.62 (d, J=8.8 Hz, 1H), 6.28 (s, 1H), 4.91 (m, 1H), 3.64 (t, J=6.0 Hz, 1H), 3.30 (m, 2H), 2.00 (m, 1H), 1.06 (m, 2H), 0.70-0.80 (m, 2H). MS: Calcd.: 378; Found: [M + H]⁺ 379 | Method 50 |
| 16 | 2-[3-(5-Cyclopropyl-1H-pyrazol-3-yl)-3H-imidazo[4,5-b]pyridin-5-ylamino]-2-(4-fluorophenyl)propane-1,3-diol | (400 MHz) 12.49 (s, 1H), 8.20 (s, 1H), 7.71 (d, J=8.8 Hz, 1H), 7.45 (m, 2H), 7.07 (m, 2H), 6.75 (s, 1H), 6.71 (d, J=8.8 Hz, 1H), 5.55 (s, 1H), 4.86 (t, J=5.2 Hz, 2H), 3.96 (m, 4H), 1.86 (m, 1H), 1.00 (m, 2H), 0.60 (m, 2H). MS: Calcd.: 408; Found: [M + H]⁺ 409 | Method 51 |
| 17 | 6-Chloro-3-(5-cyclopropyl-1H-pyrazol-3-yl)-N-[(S)-1-(4-fluorophenyl)ethyl]-3H-imidazo[4,5-b]pyridin-5-amine | (400 MHz) 12.65 (s, 1H), 8.36 (s, 1H), 8.05 (s, 1H), 7.46 (m, 2H), 7.10 (m, 2H), 5.80 (d, J=6.8 Hz, 1H), 6.21 (s, 1H), 5.17 (m, 1H), 1.99 (m, 1H), 1.56 (d, J=7.20 Hz, 3H), 1.06 (m, 2H), 0.70-0.80 (m, 2H). MS: Calcd.: 396; Found: [M + H]⁺ 397. | Method 52 |
| 18 | N-(4-Fluorobenzyl)-6-chloro-3-(5-cyclopropyl-1H-pyrazol-3-yl)-3H-imidazo[4,5-b]pyridin-5-amine | (400 MHz) 12.66 (s, 1H), 8.37 (s, 1H), 8.06 (s, 1H), 7.40 (m, 3H), 7.11 (m, 2H), 6.20 (s, 1H), 4.60 (d, J=6.0 Hz, 1H), 1.94 (m, 1H), 1.01 (m, 2H), 0.65 (m, 2H). MS: Calcd.: 382; Found: [M + H]⁺ 383. | Method 53 |
| 19 | (2R)-2-[6-Chloro-3-(5-cyclopropyl-1H-pyrazol-3-yl)-3H-imidazo[4,5-b]pyridin-5-ylamino]-2-(4-fluorophenyl)ethanol | (400 MHz) 12.64 (s, 1H), 8.38 (s, 1H), 8.09 (s, 1H), 7.44 (m, 2H), 7.12 (m, 2H), 6.65 (d, J=6.0 Hz, 1H), 6.13 (s, 1H), 5.14 (t, J=5.6 Hz, 1H), 5.04 (m, 1H), 3.69-3.80 (m, 2H), 1.98 (m, 1H), 1.06 (m, 2H), 0.70-0.80 (m, 2H). MS: Calcd.: 412; Found: [M + H]⁺ 413. | Method 54 |
| 20 | (2R)-2-[6-Chloro-3-(5-methyl-1H-pyrazol-3-yl)-3H-imidazo[4,5-b]pyridin-5-ylamino]-2-(4-fluorophenyl)ethanol | (400 MHz) 12.57 (s, 1H), 8.39 (s, 1H), 8.10 (s, 1H), 7.46 (m, 2H), 7.13 (m, 2H), 6.63 (d, J=5.2 Hz, 1H), 6.15 (s, 1H), 5.16 (t, J=5.6 Hz, 1H), 4.99 (m, 1H), 3.67-3.79 (m, 2H), 2.31 (s, 3H). MS: Calcd.: 386; Found: [M + H]⁺ 387. | Method 55 |
| 21 | 3-(5-Isopropoxy-1H-pyrazol-3-yl)-N-((S)-1-(pyridin-2-yl)ethyl)-3H-imidazo[4,5-b]pyridin-5-amine | (400 MHz) 12.38 (s, 1H), 8.49 (d, J=4.0 Hz, 1H), 8.27 (s, 1H), 7.75 (d, J=8.8 Hz, 1H), 7.67 (m, 1H), 7.44 (d, J=6.4 Hz, 1H), 7.36 (d, J=7.6 Hz, 1H), 7.20 (m, 1H), 6.63 (d, J=8.8 Hz, 1H), 6.02 (s, 1H), 5.06 (m, 1H), 4.49 (m, 1H), 1.49 (d, J=6.8 Hz, 3H), 1.40 (d, J=6.0 Hz, 3H), 1.35 (d, J=5.6 Hz, 3H). MS: Calcd.: 363; Found: [M + H]⁺ 364. | Method 56 |
| 22 | N-((S)-1-(4-Fluorophenyl)ethyl)-3-(5-isopropoxy-1H-pyrazol-3-yl)-3H-imidazo[4,5-b]pyridin-5-amine | (400 MHz) 12.42 (s, 1H), 8.26 (s, 1H), 7.73 (d, J=8.8 Hz, 1H), 7.42 (m, 2H), 7.36 (d, J=6.8 Hz, 1H), 7.09 (m 2H), 6.58 (d, J=8.8 Hz, 1H), 5.99 (s, 1H), 5.04 (m, 1H), 4.46 (m, 1H), 1.46 (d, J=6.8 Hz, 3H), 1.40 (d, J=6.0 Hz, 3H), 1.33 (d, J=6.0 Hz, 3H). MS: Calcd.: 380; Found: [M + H]⁺ 381. | Method 57 |
| 23 | (2R)-2-(4-Fluorophenyl)-2-(3-(5-isopropoxy-1H-pyrazol-3-yl)-3H-imidazo[4,5-b]pyridin-5-ylamino)ethanol | (400 MHz) 12.43 (b, 1H), 8.26 (s, 1H), 7.74 (d, J=8.8 Hz, 1H), 7.42 (m, 2H), 7.30 (d, J=6.8 Hz, 1H), 7.10 (m, 2H), 6.64 (d, J=8.8 Hz, 1H), 6.01 (s, 1H), 5.00 (t, J=6.4 Hz, 1H), 4.95 (m, 1H), 3.67 (m, 2H), 1.41 (d, J=6.0 Hz, 3H), 1.35 (d, J=6.0 Hz, 3H). MS: Calcd.: 396; Found: [M + H]⁺ 397. | Method 58 |
| 24 | 6-Chloro-N-((S)-1-(4-fluorophenyl)ethyl)-3-(5-isopropoxy-1H-pyrazol-3-yl)-3H-imidazo[4,5-b]pyridin-5-amine | (400 MHz) 12.52 (s, 1H), 8.39 (s, 1H), 8.08 (s, 1H), 7.46 (m, 2H), 7.09 (m, 2H), 6.83 (d, J=7.2 Hz, 1H), 5.95 (d, 1H), 5.23 (m, 1H), 4.49 (m, 1H), 1.57 (d, J=6.8 Hz, 3H), 1.41 and 1.34 (d, J=6.0 Hz, 6H). MS: Calcd.: 414; Found: [M + H]⁺ 415. | Method 59 |
| 25 | 3-(5-Cyclopropyl-1H-pyrazol-3-yl)-N-((S)-1-(pyridin-2-yl)ethyl)-3H-imidazo[4,5-b]pyridin-5-amine | (400 MHz) 12.56 (s, 1H), 8.54 (d, J=4.8 Hz, 1H), 8.26 (s, 1H), 7.74 (d, J=8.8 Hz, 1H), 7.67 (m, 1H), 7.43 (d, J=6.0 Hz, 1H), 7.36 (d, J=8.0 Hz, 1H), 7.20 (m, 1H), 6.62 (d, J=8.8 Hz, 1H), 6.22 (s, 1H), 5.01 (m, 1H), 1.97 (m, 1H), 1.49 (d, J=6.8 Hz, 3H), 1.03 (m, 2H), 0.81-0.70 (m, 2H). MS: Calcd.: 345; Found: [M + H]⁺ 346. | Method 60 |

-continued

| Ex. | Compound | NMR/MS | SM |
|---|---|---|---|
| 26 | (2R)-2-(4-Fluorophenyl)-2-(3-(5-methyl-1H-pyrazol-3-yl)-3H-imidazo[4,5-b]pyridin-5-ylamino)ethanol | (400 MHz) 12.53 (b, 1H), 8.27 (s, 1H), 7.73 (d, J=8.8 Hz, 1H), 7.44 (m, 2H), 7.24 (d, J=6.8 Hz, 1H), 7.13 (m, 2H), 6.62 (d, J=8.8 Hz, 1H), 6.34 (s, 1H), 4.96 (t, J=5.6 Hz, 1H), 4.91 (m, 1H), 3.65 (m, 2H), 2.32 (s, 3H). MS: Calcd.: 352; Found: [M + H]+ 353. | Method 61 |

Example 27

3-(5-Cyclopropyl-1H-pyrazol-3-yl)-N-[(S)-1-(4-fluorophenyl)ethyl]-3H-benzo[d]imidazol-5-amine A mixture of (S)-N$^3$-(5-cyclopropyl-1H-pyrazol-3-yl)-N$^1$-[1-(4-fluorophenyl)ethyl]benzene-1,3,4-triamine (Method 62; 0.395 g, 1.12 mmol) and formamidine acetate (0.234 g, 2.25 mmol) in EtOH (5 ml) was heated at reflux for 2 hrs. After cooling to 25° C., the reaction mixture was treated with saturated sodium bicarbonate solution (10 ml) and EtOAc (30 ml). The organic layer was separated, washed with brine (10 ml), and dried over Na$_2$SO$_4$. The solvent was removed under reduced pressure and the residue was purified by column chromatography (EtOAc) to give the title compound as an off-white solid (0.205 g, 50%). NMR (400 MHz) 12.65 (s, 1H), 8.17 (s, 1H), 7.43 (m, 2H), 7.33 (d, J=8.8 Hz, 1H), 7.10 (m, 2H), 6.90 (s, 1H), 6.62 (d, J=8.8 Hz, 1H), 6.25 (d, J=6.4 Hz, 1H), 6.08 (s, 1H), 4.51 (m, 1H), 1.96 (m, 1H), 1.43 (d, J=6.8 Hz, 3H), 1.02 (m, 2H), 0.76 (m, 2H). MS: Calcd.: 361; Found: [M+H]+ 362.

Examples 28-32

Following a similar procedure to Example 27, the following compounds were synthesized from a suitable aminobenzene by treatment with formamidine acetate.

| Ex. | Compound | NMR/MS | SM |
|---|---|---|---|
| 28 | (2R)-2-[3-(5-Cyclopropyl-1H-pyrazol-3-yl)-3H-benzo[d]imidazol-5-ylamino]-2-(4-fluorophenyl)ethanol | (400 MHz) 12.65 (s, 1H), 8.18 (s, 1H), 7.44 (m, 2H), 7.34 (d, J=8.8 Hz, 1H), 7.11 (m, 2H), 6.92 (s, 1H), 6.65 (d, J=8.8 Hz, 1H), 6.08 (s, 1H), 6.07 (d, J=5.6 Hz, 1H), 4.95 (t, J=5.6 Hz, 1H), 4.40 (m, 1H), 3.61 (t, J=5.6 Hz, 2H), 1.95 (m, 1H), 1.01 (m, 2H), 0.76 (m, 2H). MS: Calcd.: 377; Found: [M + H]+ 378. | Method 63 |
| 29 | N-(4-Fluorobenzyl)-3-(5-cyclopropyl-1H-pyrazol-3-yl)-3H-benzo[d]imidazol-5-amine | (400 MHz) 12.66 (s, 1H), 8.21 (s, 1H), 7.42 (m, 2H), 7.38 (d, J=8.8 Hz, 1H), 7.12 (m, 2H), 7.04 (s, 1H), 6.66 (d, J=8.8 Hz, 1H), 6.32 (t, J=6.0 Hz, 1H), 6.20 (s, 1H), 4.28 (d, J=4.8 Hz, 2H), 1.96 (m, 1H), 0.99 (m, 2H), 0.75 (m, 2H). MS: Calcd.: 347; Found: [M + H]+ 348. | Method 64 |
| 30 | N-[(S)-1-(4-Fluorophenyl)ethyl]-3-(5-isopropoxy-1H-pyrazol-3-yl)-3H-benzo[d]imidazol-5-amine | (400 MHz) 12.45 (s, 1H), 8.18 (s, 1H), 7.42 (m, 2H), 7.34 (d, J=8.4 Hz, 1H), 7.09 (m, 2H), 6.93 (s, 1H), 6.63 (d, J=8.4 Hz, 1H), 6.27 (d, J=6.4 Hz, 1H), 5.88 (s, 1H), 4.50 (m, 2H), 1.43 (d, J=6.8 Hz, 3H), 1.36 (m, 6H). MS: Calcd.: 379; Found: [M + H]+ 380. | Method 65 |
| 31 | 3-(5-Cyclopropyl-1H-pyrazol-3-yl)-N-((S)-1-(pyridin-2-yl)ethyl)-3H-benzo[d]imidazol-5-amine | (400 MHz) 12.68 (s, 1H), 8.52 (d, J=4.4 Hz, 1H), 8.18 (s, 1H), 7.69 (m, 1H), 7.40 (d, J=7.6 Hz, 1H), 7.35 (d, J=8.8 Hz, 1H), 7.21 (m, 1H), 6.91 (s, 1H), 6.64 (d, J=7.6 Hz, 1H), 6.34 (d, J=6.8 Hz, 1H), 6.10 (d, J=1.6 Hz, 1H), 4.53 (m, 1H), 1.96 (m, 1H), 1.47 (d, J=6.8 Hz, 3H), 1.03 (m, 2H), 0.76 (m, 2H). MS: Calcd.: 344; Found: [M + H]+ 345. | Method 67 |
| 32 | (2R)-2-(4-Fluorophenyl)-2-(3-(5-methyl-1H-pyrazol-3-yl)-3H-benzo[d]imidazol-5-ylamino)ethanol | (400 MHz) 12.61 (s, 1H), 8.22 (s, 1H), 7.44 (m, 2H), 7.35 (d, J=8.8 Hz, 1H), 7.12 (m, 2H), 6.98 (s, 1H), 6.64 (d, J=8.4 Hz, 1H), 6.19 (s, 1H), 6.11 (d, J=6.0 Hz, 1H), 4.96 (t, J=5.6 Hz, 1H), 4.40 (m, 1H), 3.61 (t, J=5.6 Hz, 2H), 2.30 (s, 3H). MS: Calcd.: 351; Found: [M + H]+ 352. | Method 68 |

Example 33

1-(5-Cyclopropyl-1H-pyrazol-3-yl)-6-[(S)-1-(4-fluorophenyl)ethylamino]-1H-benzo[d]imidazol-5-carbonitrile A mixture of (s)-5-amino-4-(5-cyclopropyl-1H-pyrazol-3-ylamino)-2-[1-(4-fluorophenyl)ethylamino]benzonitrile (Method 69; 3.85 g, 10.2 mmol) and formamidine acetate (2.13 g, 20.5 mmol) in EtOH (50 ml) was heated at reflux for 2 hrs. After cooling, the reaction mixture was treated with saturated sodium bicarbonate solution (10 ml) and EtOAc (30 ml). The organic layer was separated, washed with brine (10 ml), and dried over $Na_2SO_4$. The solvent was removed under reduced pressure and the residue was purified by column chromatography (EtOAc:MeOH=30:1) to give the title compound as an off-white solid (3.23 g, 82%). NMR (400 MHz) 12.79 (s, 1H), 8.44 (s, 1H), 7.95 (s, 1H), 7.53 (m, 2H), 7.14 (m, 2H), 7.01 (s, 1H), 6.10 (s, 1H), 6.09 (d, J=7.6 Hz, 1H), 4.63 (m, 1H), 1.97 (m, 1H), 1.55 (d, J=6.8 Hz, 3H), 1.03 (m, 2H), 0.76 (m, 2H). MS: Calcd.: 386; Found: [M+H]$^+$ 387.

Example 34

1-(5-Cyclopropyl-1H-pyrazol-3-yl)-6-[(S)-1-(4-fluorophenyl)ethylamino]-1H-benzo[d]imidazol-5-carboxamide 1-(5-Cyclopropyl-1H-pyrazol-3-yl)-6-[(S)-1-(4-fluorophenyl)ethylamino]-1H-benzo[d]imidazol-5-carbonitrile (Example 33; 0.30 g, 0.77 mmol) was dissolved in MeOH (10 ml), followed by addition of 25% aqueous KOH solution (0.87 ml, 3.88 mol) and 15 drops of 30% $H_2O_2$ solution. The reaction was heated at 75° C. for 48 hours. After cooling, the reaction was diluted with $H_2O$ (5 ml). The resulted solid was collected by filtration and dried under vacuum to give the title compound (0.137 g, 44%) as a white solid. NMR (400 MHz) 12.70 (s, 1H), 8.66 (d, J=4.8 Hz, 1H), 8.30 (s, 1H), 8.06 (s, 1H), 8.03 (br, 1H), 7.42 (m, 2H), 7.24 (br, 1H), 7.13 (m, 1H), 6.80 (s, 1H), 6.00 (s, 1H), 4.57 (m, 1H), 1.95 (m, 1H), 1.47 (d, J=6.0 Hz, 3H), 1.02 (m, 2H), 0.74 (m, 2H). MS: Calcd.: 404; Found: [M+H]$^+$ 405.

Example 35

Following a similar procedure to Example 33, the following compounds were synthesized from a suitable aminobenzene by treatment with formamidine acetate.

| Ex. | Compound | NMR/MS | SM |
| --- | --- | --- | --- |
| 35 | 1-(5-Cyclopropyl-1H-pyrazol-3-yl)-6-[(R)-1-(4-fluorophenyl)-2-hydroxyethylamino]-1H-benzo[d]imidazole-5-carbonitrile | (400 MHz) 12.77 (s, 1H), 8.45 (s, 1H), 7.99 (s, 1H), 7.49 (m, 2H), 7.15 (m, 2H), 6.95 (s, 1H), 6.06 (s, 1H), 5.95 (d, J=4.8 Hz, 1H), 5.32 (t, J=4.8 Hz, 1H), 3.79 (m, 1H), 3.76 (m, 1H), 3.65 (m, 1H), 1.97 (m, 1H), 1.03 (m, 2H), 0.74 (m, 2H). MS: Calcd.: 402; Found: [M + H]$^+$ 403. | Method 70 |

Example 36

3-(5-Cyclopropyl-1H-pyrazol-3-yl)-4-fluoro-N-[(S)-1-(4-fluorophenyl)ethyl]-3H-benzo[d]imidazol-5-amine A mixture of (S)-N$^3$-(5-cyclopropyl-1H-pyrazol-3-yl)-2-fluoro-N$_1$-[1-(4-fluorophenyl)ethyl]benzene-1,3,4-triamine (Method 71; 0.370 g, 1.00 mmol) and formamidine acetate (0.209 g, 2.00 mmol) in EtOH (10 ml) was heated at reflux for 1 hour. After cooling, the reaction mixture was treated with saturated sodium bicarbonate solution (5 ml) and EtOAc (15 ml). The organic layer was separated, washed with brine (3 ml), and dried over $Na_2SO_4$. The solvent was removed under reduced pressure and the residue was purified by column chromatography (hexane:EtOAc=1:1) to give the title compound as an off-white solid (0.125 g, 33%). NMR (400 MHz) 12.79 (s, 1H), 8.08 (s, 1H), 7.45 (m, 2H), 7.20 (d, J=8.4 Hz, 1H), 7.09 (t, J=8.8 Hz, 2H), 6.60 (t, J=8.2 Hz, 1H), 6.19 (s, 1H), 5.68 (d, J=7.2 Hz, 1H), 4.65 (m, 1H), 1.98 (m, 1H), 1.47 (d, J=6.8 Hz, 3H), 1.01 (m, 2H), 0.77 (m, 2H). MS: Calcd.: 379; Found: [M+H]$^+$ 380.

Example 37

Following a similar procedure to Example 36, the following compound was synthesized from a suitable aminobenzene by treatment with formamidine acetate.

| Ex. | Compound | NMR/MS | SM |
| --- | --- | --- | --- |
| 37 | (2R)-2-[3-(5-Cyclopropyl-1H- | (400 MHz) 12.78 (s, 1H), 8.09 (s, 1H), 7.44 (m, 2H), 7.20 (d, J=8.8 Hz, 1H), 7.12 (t, J=9.0 Hz, 2H), | Method 72 |

| Ex. | Compound | NMR/MS | SM |
|---|---|---|---|
|  | pyrazol-3-yl)-4-fluoro-3H-benzo[d]imidazol-5-ylamino]-2-(4-fluorophenyl)ethanol | 6.51 (t, J=8.2 Hz, 1H), 6.21 (s, 1H), 5.50 (d, J=4.4 Hz, 1H), 5.07 (t, J=5.8 Hz, 1H), 4.51 (q, J=6.0 Hz, 1H), 3.58-3.70 (m, 2H), 1.98 (m, 1H), 1.00 (m, 2H), 0.77 (m, 2H). MS: Calcd.: 395; Found: [M + H]+ 396. |  |

Example 38

3-(5-Cyclopropyl-1H-pyrazol-3-yl)-6-fluoro-N-[(S)-1-(4-fluorophenyl)ethyl]-3H-benzo[d]imidazol-5-amine A mixture of (S)-N$^3$-(5-cyclopropyl-1H-pyrazol-3-yl)-6-fluoro-N$^1$-[1-(4-fluorophenyl)ethyl]benzene-1,3,4-triamine (Method 73; 0.302 g, 0.816 mmol) and formamidine acetate (0.170 g, 1.63 mmol) in EtOH (10 ml) was heated at reflux for 1 hr. After cooling, the reaction mixture was treated with saturated sodium bicarbonate solution (5 ml) and EtOAc (15 ml). The organic layer was separated, washed with brine (3 ml), and dried over Na$_2$SO$_4$. The solvent was removed under reduced pressure and the residue was purified by column chromatography (hexane:EtOAc=1:1) to give the title compound as an off-white solid (0.170 g, 55%). NMR (400 MHz) 12.69 (s, 1H), 8.27 (s, 1H), 7.47 (m, 2H), 7.39 (d, J=12.0 Hz, 1H), 7.12 (t, J=9.0 Hz, 2H), 6.96 (d, J=8.0 Hz, 1H), 6.07 (s, 1H), 5.90 (d, J=4.8 Hz, 1H), 4.56 (m, 1H), 1.96 (m, 1H), 1.51 (d, J=6.8 Hz, 3H), 1.02 (m, 2H), 0.76 (m, 2H). MS: Calcd.: 379; Found: [M+H]+ 380.

Example 39

Following a similar procedure to Example 38, the following compounds were synthesized from a suitable aminobenzene by treatment with formamidine acetate.

| Ex. | Compound | NMR/MS | SM |
|---|---|---|---|
| 39 | (2R)-2-[3-(5-Cyclopropyl-1H-pyrazol-3-yl)-6-fluoro-3H-benzo[d]imidazol-5-ylamino]-2-(4-fluorophenyl)ethanol | (400 MHz) 12.69 (s, 1H), 8.29 (s, 1H), 7.47 (m, 3H), 7.14 (t, J=8.8 Hz, 2H), 6.93 (d, J=8.0 Hz, 1H), 6.03 (s, 1H), 5.70 (br, 1H), 5.18 (t, J=5.8 Hz, 1H), 4.45 (m, 1H), 3.62-3.73 (m, 2H), 1.95 (m, 1H), 1.02 (m, 2H), 0.74 (m, 2H). MS: Calcd.: 395; Found: [M + H]+ 396. | Method 74 |

Example 40

1-(5-Cyclopropyl-1H-pyrazol-3-yl)-N-((S)-1-(4-fluorophenyl)ethyl)-1H-imidazo[4,5-c]pyridin-6-amine A mixture of (S)-N$^4$-(5-cyclopropyl-1H-pyrazol-3-yl)-N$^2$-(1-(4-fluorophenyl)ethyl)pyridine-2,4,5-triamine (Method 88, 0.15 g, 0.43 mmol) and formamidine acetate (0.089 g, 0.85 mmol) in EtOH (5 ml) was heated at reflux for 2 hours. After cooling to 25° C., the reaction mixture was treated with saturated NaHCO$_3$ solution (10 ml) and EtOAc (30 ml). The organic layer was separated, washed with brine (10 ml), and dried over sodium sulfate. The solvent was removed under reduced pressure and the residue was purified by column chromatography (EtOAc-MeOH=40:1) to give the title compound as an off-white solid (0.092 g, 60%). $^1$H NMR (400 MHz) 12.75 (s, 1H), 8.39 (s, 1H), 8.33 (s, 1H), 7.42 (m, 2H), 7.08 (m, 2H), 6.90 (s, 1H), 6.89 (d, J=2.8 Hz, 1H), 6.26 (d, J=1.6 Hz, 1H), 5.00 (m, 1H), 1.96 (m, 1H), 1.42 (d, J=6.8 Hz, 3H), 1.02 (m, 2H), 0.76 (m, 2H). MS: Calcd.: 362; Found: [M+H]+ 363.

Example 41

(2R)-2-(1-(5-Cyclopropyl-1H-pyrazol-3-yl)-1H-imidazo[4,5-c]pyridin-6-ylamino)-2-(4-fluorophenyl)ethanol A mixture of (R)-2-(5-amino-4-(5-cyclopropyl-1H-pyrazol-3-ylamino)pyridin-2-ylamino)-2-(4-fluorophenyl)ethanol (Method 93, 0.14 g, 0.38 mmol) and formamidine acetate (0.079 g, 0.76 mmol) in EtOH (5 ml) was heated at reflux for 2 hours. After cooling to 25° C., the reaction mixture was treated with saturated NaHCO$_3$ solution (10 ml) and EtOAc (30 ml). The organic layer was separated, washed with brine (10 ml), and dried over sodium sulfate. The solvent was removed under reduced pressure and the residue was purified by column chromatography (EtOAc-MeOH=20:1) to give the title compound as an off-white solid (0.22 g, 32%). $^1$H NMR (400 MHz) 12.76 (s, 1H), 8.40 (s, 1H), 8.34 (s, 1H), 7.43 (m, 2H), 7.10 (m, 2H), 6.92 (s, 1H), 6.72 (d, J=7.2 Hz, 1H), 6.25 (s, 1H), 4.92 (m, 2H), 3.62 (m, 2H), 1.97 (m, 1H), 1.02 (m, 2H), 0.77 (m, 2H). MS: Calcd.: 378; Found: [M+H]+ 379.

Example 42

6-(Aminomethyl)-3-(5-cyclopropyl-1H-pyrazol-3-yl)-N-((S)-1-(4-fluorophenyl)ethyl)-3H-benzo[d]imidazol-5-amine To 1-(5-cyclopropyl-1H-pyrazol-3-yl)-6-((S)-1-(4-fluorophenyl)ethylamino)-1H-benzo[d]imidazol-5-carbonitrile (Example 33, 1.25 g, 3.2 mmol) and 10% palladium on carbon (0.69 g, 0.65 mmol) in MeOH (40 ml) was added 15 drops of conc. HCl. The reaction was charged 45 psi hydrogen and shook for 30 hours. The solvent was removed. The residue was dissolved in EtOAc (200 ml), washed with saturated sodium bicarbonate (50 ml) and dried over sodium sulfate. After removal of solvent, the residue was purified by reverse-phase column chromatography (5-50% $CH_3CN$ in $H_2O$) to give the title compound as an off-white solid (0.81 g, 61%). $^1H$ NMR (400 MHz) 12.65 (s, 1H), 8.15 (s, 1H), 7.46 (m, 2H), 7.36 (s, 1H), 7.11 (m, 2H), 6.91 (d, J=5.6 Hz, 1H), 6.74 (s, 1H), 5.94 (s, 1H), 4.54 (m, 1H), 3.92 (s, 2H), 2.07-1.91 (m, 3H), 1.48 (d, J=6.4 Hz, 3H), 1.01 (m, 2H), 0.72 (m, 2H). MS: Calcd.: 390; Found: $[M+H]^+$ 391.

Example 43

N-((1-(5-Cyclopropyl-1H-pyrazol-3-yl)-6-((S)-1-(4-fluorophenyl)ethylamino)-1H-benzo[d]imidazol-5-yl)methyl)acetamide A round bottom flask was charged with 6-(aminomethyl)-3-(5-cyclopropyl-1H-pyrazol-3-yl)-N-((S)-1-(4-fluorophenyl)ethyl)-3H-benzo[d]imidazol-5-amine (Example 42; 0.10 g, 0.256 mmol) and acetic acid loaded TFP resin (1.0 mmol/g loading, 0.256 g, 0.256 mmol) in mixture of THF-DCM (1:1, 3 ml) at 0° C. The resulting solution was stirred vigorously at 0° C. for 1 hour and filtered through a Jones tube. The resulting resin was washed with a THF-DCM solution (1:1, 3×5 ml). After removal of solvent, the residue was purified by column chromatography (EtOAc-MeOH=20:1) to give the title compound as an off-white solid (0.083 g, 75%). $^1H$ NMR (400 MHz) 12.67 (s, 1H), 8.50 (m, 1H), 8.18 (s, 1H), 7.39 (m, 3H), 7.11 (m, 2H), 6.73 (s, 1H), 6.09 (d, J=6.0 Hz, 1H), 5.96 (s, 1H), 4.53 (m, 1H), 4.42 (m, 1H), 4.31 (m, 1H), 1.93 (m, 1H), 1.93 (s, 3 h), 1.47 (d, J=6.4 Hz, 3H), 1.02 (m, 2H), 0.76 (m, 2H). MS: Calcd.: 432; Found: $[M+H]^+$ 433.

Example 44

1-(5-Cyclopropyl-1H-pyrazol-3-yl)-6-((S)-1-(4-fluorophenyl)ethylamino)-1H-benzo[d]imidazole-4-carbonitrile The mixture of (S)-2-amino-3-(5-cyclopropyl-1H-pyrazol-3-ylamino)-5-(1-(4-fluorophenyl)ethylamino)benzonitrile (Method 96, 3.95 g, 10 mmol) and formamidine acetate (2.2 g, 21 mmol) in EtOH (50 ml) was heated at reflux for 36 hours. After cooling, the reaction mixture was treated with saturated sodium bicarbonate solution (30 ml) and EtOAc (80 ml). The organic layer was separated, washed with brine (30 ml), and dried over sodium sulfate. The solvent was removed under reduced pressure and the residue was purified by column chromatography (EtOAc) to give the title compound as an off-white solid (1.05 g, 26%). $^1H$ NMR (400 MHz) 12.80 (s, 1H), 8.45 (s, 1H), 7.43 (m, 2H), 7.31 (d, J=2.0 Hz, 1H), 7.12 (m, 2H), 7.00 (d, J=2.0 Hz, 1H), 6.75 (d, J=6.8 Hz, 1H), 6.22 (d, J=2.0 Hz, 1H), 4.58 (m, 1H), 1.97 (m, 1H), 1.44 (d, J=6.4 Hz, 3H), 1.03 (m, 2H), 0.75 (m, 2H). MS: Calcd.: 386; Found: $[M+H]^+$ 387.

Example 45

1-(5-Cyclopropyl-1H-pyrazol-3-yl)-6-((S)-1-(4-fluorophenyl)ethylamino)-1H-benzo[d]imidazol-4-carboxamide The mixture of (S)-2-amino-3-(5-cyclopropyl-1H-pyrazol-3-ylamino)-5-(1-(4-fluorophenyl)ethylamino)benzamide (Method 100, 3.95 g, 10 mmol) and formamidine acetate (2.2 g, 21 mmol) in EtOH (50 ml) was heated at reflux for 36 hours. After cooling, the reaction mixture was treated with saturated sodium bicarbonate solution (30 ml) and EtOAc (80 ml). The organic layer was separated, washed with brine (30 ml), and dried over sodium sulfate. The solvent was removed under reduced pressure and the residue was purified by column chromatography (EtOAc-MeOH=30:1) to give the title compound as an off-white solid (0.45 g, 11%). $^1H$ NMR (400 MHz) 12.79 (s, 1H), 9.00 (d, J=2.8 Hz, 1H), 8.42 (s, 1H), 7.67 (d, J=2.8 Hz, 1H), 7.43 (m, 2H), 7.38 (d, J=2.0 Hz, 1H), 7.09 (m, 3H), 6.59 (d, J=6.4 Hz, 1H), 6.16 (d, J=1.6 Hz, 1H), 4.54 (m, 1H), 1.97 (m, 1H), 1.43 (d, J=6.4 Hz, 3H), 1.02 (m, 2H), 0.76 (m, 2H). MS: Calcd.: 404; Found: $[M+H]^+$ 405.

Example 46

3-(5-Cyclopropyl-1H-pyrazol-3-yl)-4,6-difluoro-N-((S)-1-(4-fluorophenyl)ethyl)-3H-benzo[d]imidazol-5-amine (S)-$N^3$-(5-Cyclopropyl-1H-pyrazol-3-yl)-2,6-difluoro-$N^1$-(1-(4-fluorophenyl)ethyl)benzene-1,3,4-triamine (Method 101, 0.278 g, 0.718 mmol) and formamidine acetate (0.149 g, 1.44 mmol) in EtOH (10 ml) was heated at reflux for 1 hour. Saturated sodium bicarbonate solution (5 ml) and EtOAc (15 ml) were added. The organic layer was separated, washed with brine (3 ml) and dried over sodium sulfate. The solvent was removed under reduced pressure and the residue was purified by chromatography (Hex-EtOAc=1:1) to give the title compound as off white solid (0.120 g, 42%). $^1H$ NMR (400 MHz) 12.83 (s, 1H), 8.20 (s, 1H), 7.36 (m, 2H), 7.31 (d, J=11.2 Hz, 1H), 7.06 (t, J=8.8 Hz, 2H), 6.15 (s, 1H), 5.15 (d, J=10.4 Hz, 1H), 4.67 (m, 1H), 1.98 (m, 1H), 1.46 (d, J=6.8 Hz, 3H), 1.00 (m, 2H), 0.76 (m, 2H). MS: Calcd.: 397; Found: $[M+H]^+$ 398.

Example 47

(2R)-2-(3-(5-Cyclopropyl-1H-pyrazol-3-yl)-4,6-difluoro-3H-benzo[d]imidazol-5-ylamino)-2-(4-fluorophenyl)ethanol (R)-2-(4-Amino-3-(5-cyclopropyl-1H-pyrazol-3-ylamino)-2,6-difluorophenylamino)-2-(4-fluorophenyl)ethanol (Method 104, 0.230 g, 0.57 mmol) and formamidine acetate (0.119 g, 1.14 mmol) in EtOH (10 ml) was heated at reflux for 1 hour. Saturated sodium bicarbonate solution (5 ml) and EtOAc (15 ml) were added. The organic layer was separated, washed with brine (3 ml) and dried over sodium sulfate. The solvent was removed under reduced pressure and the residue was purified by chromatography (Hex-EtOAc=1:1) to give the title compound as off white solid (0.070 g, 30%). $^1H$ NMR (400 MHz) 12.83 (s, 1H), 8.20 (s, 1H), 7.34 (m, 3H), 7.07 (t, J=8.8 Hz, 2H), 6.14 (s, 1H), 5.14 (d, J=9.6 Hz, 1H), 4.97 (t, J=5.6 Hz, 1H), 4.62 (m, 1H), 3.64-3.74 (m, 2H), 1.97 (m, 1H), 1.00 (m, 2H), 0.76 (m, 2H). MS: Calcd.: 413; Found: $[M+H]^+$ 414.

Example 48

N-(1,3-Benzodioxol-5-ylmethyl)-3-(5-cyclopropyl-1H-pyrazol-3-yl)-3H-imidazo[4,5-b]pyridin-5-amine A mixture of 6-chloro-N-(5-cyclopropyl-1H-pyrazol-3-yl)-3-nitropyridin-2-amine (Method 77, 70 mg, 0.25 mmol), piperonylamine (54 mg, 0.36 mmol), saturated NaHCO$_3$ (0.5 ml), and anhydrous 1,4-dioxane (0.5 ml) was heated at 100° C. for 3 hours. The reaction was allowed to cool to room temperature, and the solvents were evaporated in a Genevac. The resulting residue was treated with zinc dust (195 mg, 2.98 mmol), formic acid (140 µL, 3.71 mmol), and 1,4-dioxane (0.5 ml), and the resulting mixture was reheated to 100° C. After 4 hours of heating, the reaction was allowed to cool and the volatile components were evaporated using a Genevac. The concentrated reaction mixture was treated with MeOH (1 ml), DCM (1 ml), and Na$_2$CO$_3$ (125 mg). This mixture was allowed to stir at room temperature for 45 minutes, at which point the entire mixture was loaded on top of a short column of silica gel (~3 cm long×1.5 cm diameter). The column was flushed with MeOH (~15 ml), and the eluent was concentrated in a Genevac. The title compound was obtained from the residue by crystallization from CHCl$_3$/MeOH (7.2 mg). $^1$H NMR (400 MHz) 0.65-0.76 (m, 2H), 0.99 (m, 2H), 1.96 (m, 1H), 4.41 (m, 2H), 5.94 (s, 2H), 6.45 (s, 1H), 6.52 (m, 1H), 6.75 (m, 1H), 6.83 (m, 1H), 6.92 (m, 1H), 7.35 (m, 1H), 7.71 (m, 2H), 8.27 (s, 1H), 12.60 (s, 1H). MS: Calcd.: 374; Found: [M+H]$^+$ 375.

Examples 49-54

Following a similar procedure to Example 48, the following compounds were synthesized from a suitable pyridine.

Preparation of Starting Materials:

Method 1

(R)-2-[4-(5-Cyclopropyl-1H-pyrazol-3-ylamino)-6-methyl-5-nitropyrimidin-2-ylamino]-2-(4-fluorophenyl)ethanol A solution of 2-chloro-N-(5-cyclopropyl-1H-pyrazol-3-yl)-6-methyl-5-nitropyrimidin-4-amine (Method 75; 1.0 g, 3.4 mmol), DIEA (0.57 g, 4.4 mmol), and (R)-2-amino-2-(4-fluorophenyl)ethanol (0.58 g, 3.7 mmol) in n-BuOH (15 ml) was heated to 60° C. for 2 hours. The reaction was then cooled to 25° C., concentrated, and treated with hexane. The resulting solid was collected by filtration to give the title compound (1.3 g, 93%). MS: Calcd.: 413; Found: [M+H]$^+$ 414.

Methods 2-7

Following a similar procedure to Method 1, the following compounds were synthesized from 2-chloro-N-(5-cyclopropyl-1H-pyrazol-3-yl)-5-nitropyrimidin-4-amine (Method 76) or 2-chloro-N-(5-isopropoxy-1H-pyrazol-3-yl)-5-nitropyrimidin-4-amine (Method 87) and the appropriate amine.

| Ex | Compound | NMR/MS | SM |
|---|---|---|---|
| 49 | 3-(5-Cyclopropyl-1H-pyrazol-3-yl)-N-[3-(trifluoromethyl)benzyl]-3H-imidazo[4,5-b]pyridin-5-amine | $^1$H NMR (400 MHz) 0.61-0.71 (m, 2H) 0.96 (m, 2H) 1.91 (m, 1H) 4.61 (m, 2H) 6.32 (s, 1H) 6.57 (m, 1H) 7.49-7.60 (m, 2H) 7.67 (m, 1H) 7.71 (m, 1H) 7.76 (m, 1H) 8.28 (s, 1H) 12.59 (s, 1H). MS: Calcd.: 398; Found: [M + H]$^+$ 399. | Method 77 |
| 50 | 3-(5-Cyclopropyl-1H-pyrazol-3-yl)-N-(3,4-difluorobenzyl)-3H-imidazo[4,5-b]pyridin-5-amine | $^1$H NMR (400 MHz) 0.65 (m, 2H) 0.94-1.04 (m, 2H) 1.92 (m, 1H) 4.48 (m, 2H) 6.29 (s, 1H) 6.55 (m, 1H) 7.19 (m, 1H) 7.33-7.40 (m, 1H) 7.46 (m, 1H) 7.75 (m, 1H) 8.27 (s, 1H) 12.60 (s, 1H). MS: Calcd.: 366; Found: [M + H]$^+$ 367. | Method 77 |
| 51 | 3-(5-Cyclopropyl-1H-pyrazol-3-yl)-N-((1S)-1-phenylpropyl)-3H-imidazo[4,5-b]pyridin-5-amine | $^1$H NMR (400 MHz) 0.75 (m, 2H) 0.92 (m, 3H) 1.06 (m, 2H) 1.72 (m, 1H) 1.84 (m, 1H) 1.92-2.03 (m, 1H) 4.74 (m, 1H) 6.34 (s, 1H) 6.58 (m, 1H) 7.18 (m, 2H) 7.24-7.33 (m, 3H) 7.34-7.41 (m, 12H) 7.69 (m, 1H) 8.24 (s, 1H), 12.60 (s, 1H). MS: Calcd.: 358; Found: [M + H]$^+$ 359. | Method 77 |
| 52 | 3-(5-Cyclopropyl-1H-pyrazol-3-yl)-N-[2-(1H-indol-3-yl)ethyl]-3H-imidazo[4,5-b]pyridin-5-amine | $^1$H NMR (400 MHz) 0.61-0.69 (m, 2H) 0.84-0.94 (m, 2H) 1.90 (m, 1H) 3.00 (m, 2H) 3.60 (s, 2H) 6.48 (m, 1H) 6.64 (s, 1H) 6.94 (m, 1H) 7.05 (m, 1H) 7.18 (s, 1H) 7.33 (m, 1H) 7.53 (m, 1H) 7.71 (m, 1H) 8.22 s, 1H) 10.82 (s, 1H) 12.60 (s, 1H). MS: Calcd.: 383; Found: [M + H]$^+$ 384. | Method 77 |
| 53 | 3-(5-Cyclopropyl-1H-pyrazol-3-yl)-N-(2-pyridin-2-ylethyl)-3H-imidazo[4,5-b]pyridin-5-amine | $^1$H NMR (400 MHz) 0.73 (m, 2H) 0.92-1.02 (m, 2H) 1.97 (m, 1H) 3.02-3.11 (m, 2H) 3.62-3.72 (m, 2H) 6.47 (m, 1H) 6.70 (s, 1H) 6.94-7.03 (m, 1H) 7.22 (m, 1H) 7.29 (m, 1H) 7.67-7.77 (m, 2H) 8.31 (s, 1H) 8.53 (m, 1H) 12.64 (s, 1H). MS: Calcd.: 345; Found: [M + H]$^+$ 346. | Method 77 |
| 54 | 2-{[3-(5-Cyclopropyl-1H-pyrazol-3-yl)-3H-imidazo[4,5-b]pyridin-5-yl]amino}-1-phenylpropan-1-ol | $^1$H NMR (400 MHz) 0.77 (m, 2H) 0.94 (d, J=6.8 Hz, 34H) 1.03 (m, 2H) 1.98-2.09 (m, 1H) 4.20 (m, 1H) 4.89-4.99 (m, 1H) 5.30 (m, 1H) 6.57 (m, 1H) 6.62 (s, 1H) 6.77 (m, 1H) 7.21 (m, 2H) 7.33 (m, 2H) 7.38-7.47 (m, 1H) 7.72 (m, 1H) 8.25 (s, 1H) 12.69 (s, 1H). MS: Calcd.: 374; Found: [M + H]$^+$ 375. | Method 77 |

| Meth | Product | NMR/MS | Amine |
|---|---|---|---|
| 2 | $N^4$-(5-Cyclopropyl-1H-pyrazol-3-yl)-$N^2$-[(1S)-1-(4-fluorophenyl) ethyl]-5-nitro pyrimidine-2,4-diamine | 0.62 (m, 2H), 0.95 (m, 2H), 1.49 (m, 3H), 1.90 (m, 1H), 5.12 (m, 1H), 6.13 (s, 1H), 7.15 (m, 2H), 7.37 (m, 2H), 8.97 (s, 1H), 10.40 (s, 1H). MS: Calcd.: 383; Found: [M + H]$^+$ 384.17 | [(1S)-1-(4-fluorophenyl) ethyl]amine |
| 3 | (2R)-2-({4-[(5-Cyclopropyl-1H-pyrazol-3-yl)amino]-5-nitropyrimidin-2-yl}amino)-2-(4-fluorophenyl)ethanol | 0.68 (m, 2H), 0.98 (m, 2H), 1.93 (m, 3H), 3.67 (m, 2H), 5.02 (m, 1H), 6.20 (s, 1H), 7.19 (m, 2H), 7.37 (m, 2H), 8.97 (s, 1H), 10.40 (s, 1H), 12.36 (br s, 1H). MS: Calcd.: 399; Found: [M + H]$^+$ 400.20 | (2R)-2-amino-2-(4-fluoro phenyl)ethanol |
| 4 | $N^4$-(5-Cyclopropyl-1H-pyrazol-3-yl)-$N^2$-(4-fluorobenzyl)-5-nitropyrimidine-2,4-diamine | 0.68 (m, 2H), 0.80 (m, 2H), 1.75 (m, 3H), 4.51 (m, 2H), 6.05 (s, 1H), 7.09 (m, 2H), 7.30 (m, 2H), 8.97 (s, 1H), 10.40 (s, 1H), MS: Calcd.: 369; Found: [M + H]$^+$ 370.16 | (4-fluoro benzyl)amine |
| 5 | $N^4$-(5-Cyclopropyl-1H-pyrazol-3-yl)-$N^2$-[(1R)-1-(4-fluorophenyl) ethyl]-5-nitro pyrimidine-2,4-diamine | 0.63 (m, 2H), 0.95 (m, 2H), 1.49 (m, 3H), 1.90 (m, 1H), 5.11 (m, 1H), 6.14 (s, 1H), 7.15 (m, 2H), 7.37 (m, 2H), 8.97 (s, 1H), 10.40 (s, 1H). MS: Calcd.: 383; Found: [M + H]$^+$ 384.23 | [(1R)-1-(4-fluorophenyl) ethyl]amine |
| 6 | (R)-2-(4-Fluorophenyl)-2-(4-(5-methyl-1H-pyrazol-3-ylamino)-5-nitropyrimidin-2-ylamino)ethanol | MS: Calcd.: 373; Found: [M + H]$^+$ 374 | (R)-2-amino-2-(4-fluorophenyl)ethanol |
| 7 | (S)-$N^2$-(1-(4-Fluorophenyl)ethyl)-$N^4$-(5-isopropoxy-1H-pyrazol-3-yl)-5-nitropyrimidin-2,4-diamine | (400 MHz) 12.23, 11.99 and 11.69 (s, 1H), 10.52, 10.48 and 10.37 (s, 1H), 9.15 and 9.97 (d, J=7.2 Hz, 1H), 8.99 (s, 1H), 7.45-7.31 (m, 2H), 7.20-7.08 (m, 2H), 5.99, 5.85 and 5.77 (s, 1H), 5.28, 5.18 and 5.08 (m, 1H), 4.70, 4.63 and 4.32 (m, 1H), 1.50 (d, J=6.8 Hz, 3H), 1.34-1.23 (m, 6H). MS: Calcd.: 401; Found: [M + H]$^+$ 402. | (S)-1-(4-fluoro-phenyl)-ethylamine |

Method 8

(S)-$N^4$-(5-Cyclopropyl-1H-pyrazol-3-yl)-$N^2$-[1-(4-fluorophenyl)ethyl]pyrimidine-2,4,5-triamine To a suspension of (S)-$N^4$-(5-cyclopropyl-1H-pyrazol-3-yl)-$N^2$-[1-(4-fluorophenyl)ethyl]-5-nitropyrimidine-2,4-diamine (Method 9; 0.8 g, 2.0 mmol) and zinc dust (0.7 g, 10.0 mmol) in MeOH:THF (1:1, 50 ml) was slowly added saturated NH$_4$Cl solution (10 ml) at 25° C. After 3 hours, the reaction mixture was treated with saturated aqueous NH$_4$OAc solution (40 ml) and allowed to stir for 30 minutes. The reaction was then filtered through a plug of celite with EtOAc (100 ml), and the resulting aqueous layer was extracted with EtOAc (2×100 ml), dried, filtered, and concentrated to give the title compound (0.04 g, 5%). MS: Calcd.: 353; Found: [M+H]$^+$ 354.

Method 9

(S)-$N^4$-(5-Cyclopropyl-1H-pyrazol-3-yl)-$N^2$-[1-(4-fluorophenyl)ethyl]-5-nitropyrimidine-2,4-diamine A mixture of 2-chloro-N-(5-cyclopropyl-1H-pyrazol-3-yl)-5-nitropyrimidin-4-amine (Method 76; 1.0 g, 3.6 mmol), (S)-1-(4-fluorophenyl)ethanamine (0.5 g, 3.6 mmol), and DIEA (0.6 g, 4.6 mmol) in n-BuOH (15 ml) was stirred at 25° C. for 1 hour and then concentrated. The resulting oil was purified by column chromatography (DCM:MeOH=50:1) to give the title compound (0.8 g, 60%). MS: Calcd.: 383; Found: [M+H]$^+$ 384.

Method 10

(S)-Ethyl 6-(5-cyclopropyl-1H-pyrazol-3-ylamino)-2-[1-(4-fluorophenyl)ethylamino]-5-nitropyrimidine-4-carboxylate A solution of ethyl 2-chloro-6-(5-cyclopropyl-1H-pyrazol-3-ylamino)-5-nitropyrimidine-4-carboxylate (Method 11; 1.0 g, 2.8 mmol) and (S)-1-(4-fluorophenyl)ethanamine (0.43 g, 3.1 mmol) in EtOH (20 ml) was stirred at 25° C. for 1 hour. The reaction was concentrated, treated with water (50 ml), extracted with DCM (3×50 ml), dried, filtered, and concentrated. The residue was then purified by column chromatography (DCM:MeOH=50:1) to give the title compound (0.7 g, 53%). MS: Calcd.: 455; Found: [M+H]$^+$ 456.

Method 11

Ethyl 2-Chloro-6-(5-cyclopropyl-1H-pyrazol-3-ylamino)-5-nitropyrimidine-4-carboxylate To a THF (20 ml) solution of ethyl 2,6-dichloro-5-nitropyrimidine-4-carboxylate (1.0 g, 3.80 mmol) was slowly added the 5-cyclopropyl-1H-pyrazol-3-amine (0.48 g, 3.85 mmol) in THF (5 ml) at 0° C. The reaction was stirred at 0° C. for 10 minutes, treated with water (50 ml), and then extracted with DCM (3×50 ml), dried, filtered, and concentrated to give the title compound (1.2 g). MS: Calcd.: 352; Found: [M+H]$^+$ 353.

Method 12

(S)-N²-(5-Cyclopropyl-1H-pyrazol-3-yl)-N⁶-[1-(4-fluorophenyl)ethyl]-3-nitropyridine-2,6-diamine A mixture of 6-chloro-N-(5-cyclopropyl-1H-pyrazol-3-yl)-3-nitropyridin-2-amine (Method 77; 0.30 g, 1.07 mmol), (S)-1-(4-fluoro-phenyl)ethylamine (0.23 g, 1.61 mmol), and DIEA (0.23 ml, 1.34 mmol) in n-BuOH (5 ml) was heated in a sealed tube at 165° C. for 18 hours. The solvent was removed under reduced pressure and the residue was purified by column chromatography (hexane:EtOAc=1:1) to give the title compound as a yellow solid (0.41 g, 99%). NMR (400 MHz) 12.22 (s, 1H), 10.98 (s, 1H), 8.70 (d, J=7.2 Hz, 1H), 8.10 (d, J=9.2 Hz, 1H), 7.39 (m, 2H), 7.18 (m, 2H), 6.22 (d, J=9.2 Hz, 1H), 6.17 (s, 1H), 5.27 (m, 1H), 1.89 (m, 1H), 1.52 (d, J=6.4 Hz, 3H), 0.95 (m, 2H), 0.64 (m 2H). MS: Calcd.: 382; Found: [M+H]⁺ 383.

Methods 13-15

Following a similar procedure to Method 12, the following compounds were synthesized from 6-chloro-N-(5-cyclopropyl-1H-pyrazol-3-yl)-3-nitropyridin-2-amine (Method 77) and the appropriate amine.

| Meth | Product | NMR/MS | Amine |
|---|---|---|---|
| 13 | N⁶-(4-Fluorobenzyl)-N²-(5-cyclopropyl-1H-pyrazol-3-yl)-3-nitropyridine-2,6-diamine | (400 MHz) 12.24 (s, 1H), 10.98 (s, 1H), 8.29 (br, 1H), 8.11 (d, J=9.2 Hz, 1H), 7.36 (m, 2H), 7.18 (m, 2H), 6.20 (d, J=9.6 Hz, 1H), 6.19 (s, 1H), 4.66 (d, J=5.2 Hz, 2H), 1.79 (m, 1H), 0.86 (m, 2H), 0.45 (m, 2H). MS: Calcd.: 368; Found: [M + H]⁺ 369 | (4-fluorobenzyl)amine |
| 14 | (R)-2-[6-(5-Cyclopropyl-1H-pyrazol-3-ylamino)-5-nitropyridin-2-ylamino]-2-(4-fluorophenyl)ethanol | (400 MHz) 12.21 (s, 1H), 10.97 (s, 1H), 8.74 (d, J=7.6 Hz, 1H), 8.09 (d, J=9.6 Hz, 1H), 7.38 (m, 2H), 7.18 (m, 2H), 6.31 (d, J=9.2 Hz, 1H), 6.20 (s, 1H), 5.21 (d, J=5.6 Hz, 1H), 5.09 (t, J=5.2 Hz, 1H), 3.64-3.75 (m, 2H), 1.91 (m, 1H), 0.98 (m, 2H), 0.66 (m, 2H). MS: Calcd.: 398; Found: [M + H]⁺ 399. | (R)-2-amino-2-(4-fluorophenyl)ethanol |
| 15 | 2-[6-(5-Cyclopropyl-1H-pyrazol-3-ylamino)-5-nitropyridin-2-ylamino]-2-(4-fluorophenyl)propane-1,3-diol | (400 MHz) 12.02 (s, 1H), 10.95 (s, 1H), 8.07 (d, J=9.2 Hz, 1H), 7.93 (s, 1H), 7.35 (m, 2H), 7.14 (m, 2H), 6.48 (d, J=9.2 Hz, 1H), 5.04 (s, 1H), 4.81 (s, 2H), 4.04 (m, 2H), 3.90 (m, 2H), 1.68 (m, 1H), 0.90 (m, 2H), 0.51 (m, 2H). MS: Calcd.: 428; Found: [M + H]⁺ 429. | 2-amino-2-(4-fluorophenyl)propane-1,3-diol |

Method 16

(S)-3-Chloro-N⁶-(5-cyclopropyl-1H-pyrazol-3-yl)-N²-[1-(4-fluorophenyl)ethyl]-5-nitropyridin-2,6-diamine A mixture of 5,6-chloro-N-(5-cyclopropyl-1H-pyrazol-3-yl)-3-nitropyridine-2-amine (Method 79; 0.26 g, 0.83 mmol), (S)-1-(4-fluoro-phenyl)ethylamine (0.17 g, 1.25 mmol), and DIEA (0.22 ml, 1.25 mmol) in n-BuOH (5 ml) was heated in a sealed tube at 165° C. for 3 hours. The solvent was removed under reduced pressure and the residue was purified by column chromatography (hexane:EtOAc=1:1) to give (S)-3-chloro-N⁶-(5-cyclopropyl-1H-pyrazol-3-yl)-N²-(1-(4-fluorophenyl)ethyl]-5-nitropyridin-2,6-diamine as a yellow solid (0.34 g, 99%). NMR (400 MHz) 12.29 (s, 1H), 10.68 (s, 1H), 8.27 (s, 1H), 8.24 (d, J=8.0 Hz, 1H), 7.39 (m, 2H), 7.16 (m, 2H), 6.11 (s, 1H), 5.42 (m, 1H), 1.89 (m, 1H), 1.60 (d, J=7.2 Hz, 3H), 0.95 (m, 2H), 0.61 (m, 2H). MS: Calcd.: 416; Found: [M+H]⁺ 417.

Methods 17-25

Following a similar procedure to Method 16, the following compounds were synthesized from the appropriate starting material and amine.

| Meth | Product | NMR/MS | SM | Amine 2 |
|---|---|---|---|---|
| 17 | N²-(4-Fluorobenzyl)-3-chloro-N⁶-(5-cyclopropyl-1H-pyrazol-3-yl)-5-nitropyridin-2,6-diamine | (400 MHz) 12.29 (s, 1H), 10.73 (s, 1H), 8.70 (t, J=6.0 Hz, 1H), 8.12 (b, 1H), 7.30 (m, 2H), 7.16 (m, 2H), 6.02 (s, 1H), 4.71 (d, J=6.0 Hz, 2H), 1.77 (m, 1H), 0.86 (m, 2H), 0.41 (m, 2H). MS: Calcd.: 402; Found: [M + H]⁺ 403. | Method 79 | (4-fluorophenyl)methanamine |

| Meth | Product | NMR/MS | SM | Amine 2 |
|---|---|---|---|---|
| 18 | (R)-2-[3-Chloro-6-(5-cyclopropyl-1H-pyrazol-3-ylamino)-5-nitropyridin-2-ylamino]-2-(4-fluorophenyl)ethanol | (400 MHz) 12.27 (s, 1H), 10.70 (s, 1H), 8.29 (d, J=1.6 Hz, 1H), 8.03 (d, J=7.6 Hz, 1H), 7.39 (m, 2H), 7.14 (m, 2H), 6.15 (s, 1H), 5.31 (m, 1H), 5.13 (t, J=4.8 Hz, 1H), 3.32-3.86 (m, 2H), 1.92 (m, 1H), 0.98 (m, 2H), 0.68 (m, 2H). MS: Calcd.: 432; Found: [M + H]$^+$ 433. | Method 80 | 5-cyclopropyl-1H-pyrazol-3-amine |
| 19 | (2R)-2-({3-Chloro-6-[(5-methyl-1H-pyrazol-3-yl)amino]-5-nitropyridin-2-yl}amino)-2-(4-fluorophenyl)ethanol | (400 MHz) 12.23 (s, 1H), 10.69 (s, 1H), 8.30 (s, 1H), 8.00 (d, J=7.6 Hz, 1H), 7.41 (m 2H), 7.17 (m, 2H), 6.12-5.26 (m, 1H), 5.13 (t, J=5.2 Hz, 1H), 3.73-3.86 (m, 2H), 2.25 (s, 3H). MS: Calcd.: 406; Found: [M + H]$^+$ 407 | Method 80 | 5-methyl-1H-pyrazol-3-amine |
| 20 | (S)-N$^2$-(5-Isopropoxy-1H-pyrazol-3-yl)-3-nitro-N$^6$-(1-(pyridin-2-yl)ethyl)pyridine-2,6-diamine | (400 MHz) 12.10, 12.05 and 11.84 (s, 1H), 10.96, 10.94 and 10.74 (s, 1H), 9.09, 8.88 and 8.83 (d, J=7.6 Hz, 1H), 8.56 and 8.53 (m, 1H), 8.15 and 8.11 (d, J=9.6 Hz, 1H), 7.77 (m, 1H), 7.33 (m, 1H), 7.28 (m, 1H), 6.28 and 6.07 (d, J=9.6 Hz, 1H), 5.99 and 5.83 (s, 1H), 5.78 and 5.77 (s, 1H), 5.35, 5.26 and 4.92 (m, 1H), 4.69, 4.68 and 4.50 (m, 1H), 1.55 (d, J=6.8 Hz, 3H), 1.36 and 1.28 (m, 6H). MS: Calcd.: 383; Found: [M + H]$^+$ 384. | Method 95 | (S)-1-(pyridin-2-yl)ethylamine |
| 21 | (S)-N$^6$-(1-(4-Fluorophenyl)ethyl)-N$^2$-(5-isopropoxy-1H-pyrazol-3-yl)-3-nitropyridine-2,6-diamine | (400 MHz) 12.09, 12.05 and 11.64 (s, 1H), 10.94, 10.87 and 10.72 (s, 1H), 8.98, 8.76 and 8.70 (d, J=7.6 Hz, 1H), 8.16 and 8.11 (d, J=9.6 Hz, 1H), 7.45, 7.39 and 7.34 (m, 2H), 7.15 (m, 2H), 6.24 and 6.04 (d, J=9.6 Hz, 1H), 6.03, 5.88 and 5.76 (s, 1H), 5.32, 5.21 and 4.89 (m, 1H), 4.71, 4.59 and 4.27 (m, 1H), 1.52 (m, 3H), 1.26 (m, 6H). MS: Calcd.: 400; Found: [M + H]$^+$ 401. | Method 95 | (S)-1-(4-fluoro-phenyl)-ethylamine |
| 22 | (R)-2-(4-Fluorophenyl)-2-(6-(5-isopropoxy-1H-pyrazol-3-ylamino)-5-nitropyridin-2-ylamino)ethanol | (400 MHz) 12.12, 12.10 and 11.61 (s, 1H), 10.94, 10.87 and 10.74 (s, 1H), 9.05, 8.82 and 8.73 (d, J=7.2 Hz, 1H), 8.15 and 8.11 (d, J=9.2 Hz, 1H), 7.45, 7.38 and 7.32 (m, 2H), 7.15 (m, 2H), 6.32 and 6.07 (d, J=9.2 Hz, 1H), 5.90, 5.83 and 5.79 (s, 1H), 5.32, 5.21 and 4.89 (m, 1H), 5.23 (m, 1H), 5.12 (m, 1H), 4.78, 4.64 and 4.37 (m, 1H), 4.69 (m, 2H), 1.30 (m, 6H). MS: Calcd.: 416; Found: [M + H]$^+$ 417. | Method 95 | (R)-2-amino-2-(4-fluorophenyl)ethanol |
| 23 | (S)-3-Chloro-N$^2$-(1-(4-fluorophenyl)ethyl)-N$^6$-(5-isopropoxy-1H-pyrazol-3-yl)-5-nitropyridin-2,6-diamine | (400 MHz) 12.16 and 11.72 (s, 1H), 10.64 and 10.58 (s, 1H), 8.30 (m, 2H), 7.33 and 7.31 (m, 2H), 7.16 and 7.08 (m, 2H), 5.81 and 5.71 (s, 1H), 5.48 and 5.33 (m, 1H), 4.60 and 4.21 (m, 1H), 1.61 and 1.57 (d, J=6.8 Hz, 3H), 1.26 (m, 6H). MS: Calcd.: 434; Found: [M + H]$^+$ 435. | Method 81 | (S)-1-(4-fluoro-phenyl)-ethylamine |
| 24 | (S)-N$^2$-(5-Cyclopropyl-1H-pyrazol-3-yl)-3-nitro-N$^6$-(1-(pyridin-2-yl)ethyl)pyridine-2,6-diamine | (400 MHz) 12.24 (s, 1H), 11.01 (s, 1H), 8.30 (d, J=7.2 Hz, 1H), 8.56 (m, 1H), 8.10 (d, J=9.6 Hz, 1H), 7.76 (m, 1H), 7.32 (d, J=8.0 Hz, 1H), 7.28 (m, 1H), 6.28 (d, J=9.2 Hz, 1H), 6.15 (s, 1H), 5.28 (m, 1H), 1.85 (m, 1H), 1.54 (d, J=6.8 Hz, 3H), 0.97 (m, 2H), 0.84 (m, 2H). MS: Calcd.: 365; Found: [M + H]$^+$ 366. | Method 77 | (S)-1-(pyridin-2-yl)-ethylamine |
| 25 | (R)-2-(4-Fluorophenyl)-2-(6-(5-methyl-1H-pyrazol-3-ylamino)-5-nitropyridin-2-ylamino)ethanol | (400 MHz) 12.18 (s, 1H), 10.96 (s, 1H), 9.05, 8.79 (d, J=7.2 Hz, 1H), 8.09 (d, J=9.2 Hz, 1H), 7.39 (m, 2H), 7.18 (m, 2H), 6.33 (d, J=9.6 Hz, 1H), 6.19 (s, 1H), 5.17 (m, 1H), 5.11 (t, J=5.6 Hz, 1H), 3.68 (m, 2H), 2.24 (s, 3H). MS: Calcd.: 372; Found: [M + H]$^+$ 373. | Method 78 | (R)-2-amino-2-(4-fluorophenyl)ethanol |

Method 26

(S)-N³-(5-Cyclopropyl-1H-pyrazol-3-yl)-N¹-[1-(4-fluorophenyl)ethyl]-4-nitrobenzene-1,3-diamine A mixture of 5-cyclopropyl-N-(5-fluoro-2-nitrophenyl)-1H-pyrazol-3-amine (Method 82; 0.27 g, 1.03 mmol), (S)-1-(4-fluoro-phenyl)-ethylamine (0.72 g, 5.15 mmol), and DIEA (0.27 ml, 1.54 mmol) in n-BuOH (5 ml) was heated in a sealed tube at 230° C. for 23 hours. The solvent was removed under reduced pressure and the residue was purified by column chromatography (hexane:EtOAc=1:2) to give the title compound as a yellow solid (0.38 g, 97%). NMR (400 MHz) 12.25 (s, 1H), 10.14 (s, 1H), 7.87 (d, J=9.6 Hz, 1H), 7.76 (d, J=6.4 Hz, 1H), 7.36 (m, 2H), 7.15 (m, 2H), 6.68 (s, 1H), 6.22 (d, J=8.4 Hz, 1H), 5.60 (br, 1H), 4.57 (m, 1H), 1.87 (m, 1H), 1.44 (d, J=6.8 Hz, 3H), 0.98 (m, 2H), 0.70 (m 2H). MS: Calcd.: 381; Found: [M+H]⁺ 382.

Methods 27-31

Following a similar procedure to Method 26, the following compounds were synthesized from the appropriate starting materials.

Method 32

(S)-4-(5-Cyclopropyl-1H-pyrazol-3-ylamino)-2-[1-(4-fluorophenyl)ethylamino]-5-nitrobenzonitrile A mixture of 4-(5-cyclopropyl-1H-pyrazol-3-ylamino)-2-fluoro-5-nitrobenzonitrile (Method 33; 3.0 g, 10.4 mmol), (S)-1-(4-fluoro-phenyl)ethylamine (1.60 g, 11.5 mmol), and DIEA (2.3 ml, 13.1 mmol) in n-BuOH (20 ml) was heated in a sealed tube at 230° C. for 2 hours. The solvent was removed under reduced pressure and the residue was purified by column chromatography (hexane:EtOAc=1:2) to give the title compound as a yellow solid (4.1 g, 97%). NMR (400 MHz) 12.41 (s, 1H), 9.95 (s, 1H), 8.39 (s, 1H), 7.44 (m, 2H), 7.38 (d, J=6.4 Hz, 1H), 7.13 (m, 2H), 6.95 (s, 1H), 5.68 (s, 1H), 4.56 (m, 1H), 1.91 (m, 1H), 1.55 (d, J=6.8 Hz, 3H), 0.96 (m, 2H), 0.72 (m 2H). MS: Calcd.: 406; Found: [M+H]⁺ 407.

Method 33

4-(5-Cyclopropyl-1H-pyrazol-3-ylamino)-2-fluoro-5-nitrobenzonitrile

To a solution of 2,4-difluoro-5-nitrobenzonitrile (Method 34, 5.0 g, 27 mmol) and DIEA (5.4 ml, 31 mmol) in THF (20

| Meth | Product | NMR/MS | SM | Amine |
|------|---------|--------|-----|-------|
| 27 | (R)-2-[3-(5-Cyclopropyl-1H-pyrazol-3-ylamino)-4-nitrophenylamino]-2-(4-fluorophenyl)ethanol | (400 MHz) 12.25 (s, 1H), 10.14 (s, 1H), 7.87 (d, J=9.6 Hz, 1H), 7.72 (d, J=6.8 Hz, 1H), 7.35 (m, 2H), 7.15 (m, 2H), 6.74 (br, 1H), 6.27 (br, 1H), 5.62 (br, 1H), 5.03 (t, J=5.6 Hz, 1H), 4.46 (m, 1H), 3.62 (t, J=5.6 Hz, 2H), 1.89 (m, 1H), 0.97 (m, 2H), 0.71 (m 2H). MS: Calcd.: 397; Found: [M + H]⁺ 398. | Method 82 | (R)-2-amino-2-(4-fluorophenyl)ethanol |
| 28 | N¹-(4-Fluorobenzyl)-N³-(5-cyclopropyl-1H-pyrazol-3-yl)-4-nitrobenzene-1,3-diamine | (400 MHz) 12.26 (s, 1H), 10.22 (s, 1H), 7.91 (d, J=9.2 Hz, 1H), 7.86 (t, J=5.6 Hz, 1H), 7.36 (m, 2H), 7.17 (m, 2H), 6.90 (s, 1H), 6.24 (d, J=9.6 Hz, 1H), 5.70 (s, 1H), 4.44 (d, J=5.6 Hz, 2H), 1.87 (m, 1H), 0.94 (m, 2H), 0.69 (m 2H). MS: Calcd.: 367; Found: [M + H]⁺ 368. | Method 82 | (4-fluorophenyl)methanamine |
| 29 | (S)-N¹-[1-(4-Fluorophenyl)ethyl]-N³-(5-isopropoxy-1H-pyrazol-3-yl)-4-nitrobenzene-1,3-diamine | MS: Calcd.: 399; Found: [M + H]⁺ 400. | Method 83 | (S)-1-(4-fluoro-phenyl)-ethylamine |
| 30 | (S)-N³-(5-Cyclopropyl-1H-pyrazol-3-yl)-4-nitro-N¹-(1-(pyridin-2-yl)ethyl)benzene-1,3-diamine | (400 MHz) 12.28 (s, 1H), 10.18 (b, 1H), 8.54 (s, 1H), 7.89 (d, J=9.2 Hz, 1H), 7.84 (d, J=6.0 Hz, 1H), 7.77 (m, 2H), 7.34 (d, J=8.0 Hz, 1H), 7.28 (m, 1H), 6.65 (m, 1H), 6.24 (m, 1H), 5.60 (m, 1H), 4.60 (m, 1H), 1.89 (m, 1H), 1.49 (d, J=6.4 Hz, 3H), 0.97 (m, 2H), 0.73 (m 2H). MS: Calcd.: 363; Found: [M + H]⁺ 365. | Method 82 | (S)-1-(pyridin-2-yl)-ethylamine |
| 31 | (R)-2-(4-Fluorophenyl)-2-(3-(5-methyl-1H-pyrazol-3-ylamino)-4-nitrophenylamino)ethanol | (400 MHz) 12.22 (s, 1H), 10.15 (s, 1H), 7.87 (d, J=9.6 Hz, 1H), 7.75 (d, J=6.0 Hz, 1H), 7.36 (m, 2H), 7.17 (m, 2H), 6.67 (b, 1H), 6.28 (m, 1H), 5.53 (m, 1H), 5.06 (t, J=5.6 Hz, 1H), 4.45 (m, 1H), 3.62 (t, J=5.6 Hz, 2H), 2.23 (s, 3H). MS: Calcd.: 371; Found: [M + H]⁺ 372. | Method 84 | (R)-2-amino-2-(4-fluorophenyl)ethanol | ml) was added dropwise a solution of 5-cyclopropyl-1H-pyrazol-3-amine (3.2 g, 26 mmol) in THF (5 ml) at 0° C. After addition, the reaction mixture was stirred at 25° C. for 1 hour. The solvent was removed under reduced pressure and the resulted residue was purified by column chromatography (hexane:EtOAc=3:1) to give the title compound as a yellow solid (5.5 g, 74%). NMR (400 MHz) 12.54 (s, 1H), 10.13 (s, 1H), 8.78 (d, J=7.2 Hz, 1H), 8.10 (d, J=13.6 Hz, 1H), 6.02 (s, 1H), 1.91 (m, 1H), 0.97 (m, 2H), 0.72 (m, 2H). MS: Calcd.: 287; Found: [M+H]$^+$ 288.

Method 34

2,4-Difluoro-5-nitrobenzonitrile

Potassium nitrate (16.4 g, 147.4 mmol) was added to concentrated $H_2SO_4$ (85 ml, 1582 mmol) at 0° C., followed by slow addition of 2,4-difluorobenzonitrile (11.0 g, 79.1 mmol). The suspension was stirred at this temperature for an additional 4 hrs and quenched ice/water (800 ml). The resulting solid was collected by filtration and dried to give the title compound (13.8 g, 95%) as a white solid. NMR (400 MHz, $CDCl_3$) 8.48 (m, 1H), 7.24 (m, 1H).

Method 35

Following a similar procedure to Method 32, the following compounds were synthesized from 4-(5-cyclopropyl-1H-pyrazol-3-ylamino)-2-fluoro-5-nitrobenzonitrile (Method 33) and the appropriate amine.

| Meth | Product | NMR/MS | Amine 2 |
|---|---|---|---|
| 35 | (R)-4-(5-Cyclopropyl-1H-pyrazol-3-ylamino)-2-[1-(4-fluorophenyl)-2-hydroxyethylamino]-5-nitrobenzonitrile | (400 MHz) 12.40 (s, 1H), 9.95 (s, 1H), 8.42 (s, 1H), 7.41 (m, 1H), 7.12 (m, 4H), 6.93 (s, 1H), 5.64 (s, 1H), 5.24 (t, J=5.2 Hz, 1H), 4.47 (m, 1H), 3.75 (m, 1H), 3.69 (m, 1H), 1.91 (m, 1H), 0.99 (m, 2H), 0.71 (m, 2H). MS: Calcd.: 422; Found: [M + H]$^+$ 423. | (R)-2-amino-2-(4-fluorophenyl)ethanol |

Method 36

(S)-N$^3$-(5-Cyclopropyl-1H-pyrazol-3-yl)-2-fluoro-N$^1$-[1-(4-fluorophenyl)ethyl]-4-nitrobenzene-1,3-diamine A mixture of 5-cyclopropyl-N-(2,3-difluoro-6-nitrophenyl)-1H-pyrazol-3-amine (Method 85; 0.400 g, 1.43 mmol), (S)-1-(4-fluoro-phenyl)ethylamine (0.209 g, 1.50 mmol, and DIEA (0.373 ml, 2.14 mmol) in n-BuOH (3 ml) was heated in a sealed tube at 160° C. for 8 hours. The solvent was removed under reduced pressure and the residue was purified by column chromatography (hexane:EtOAc=4:1) to give the title compound as an orange solid (0.40 g, 70%). NMR (400 MHz) 11.95 (s, 1H), 8.74 (s, 1H), 7.72 (d, J=9.2 Hz, 1H), 7.43 (t, J=7.0 Hz, 2H), 7.25 (d, J=6.4 Hz, 1H), 7.15 (t, J=8.8 Hz, 2H), 6.26 (t, J=8.6 Hz, 1H), 5.63 (s, 1H), 4.78 (m, 1H), 1.84 (m, 1H), 1.48 (d, J=6.8 Hz, 3H), 0.91 (m, 2H), 0.66 (m, 2H). MS: Calcd.: 399; Found: [M+H]$^+$ 400.

Method 37

Following a similar procedure to Method 36, the following compound was synthesized from 5-cyclopropyl-N-(2,3-difluoro-6-nitrophenyl)-1H-pyrazol-3-amine (Method 85) and the appropriate amine.

| Meth | Product | NMR/MS | Amine 2 |
|---|---|---|---|
| 37 | (R)-2-[3-(5-Cyclopropyl-1H-pyrazol-3-ylamino)-2-fluoro-4-nitrophenylamino]-2-(4-fluoro phenyl)ethanol | (400 MHz) 11.95 (s, 1H), 8.74 (s, 1H), 7.72 (d, J=9.6 Hz, 1H), 7.42 (m, 2H), 7.15 (t, J=8.8 Hz, 2H), 7.02 (d, J=4.4 Hz, 1H), 6.23 (t, J=8.6 Hz, 1H), 5.63 (s, 1H), 5.04 (t, J=5.8 Hz, 1H), 4.65 (m, 1H), 3.61-3.74 (m, 2H), 1.84 (m, 1H), 0.91 (m, 2H), 0.66 (m, 2H). MS: Calcd.: 415; Found: [M + H]$^+$ 416. | (R)-2-amino-2-(4-fluorophenyl)ethanol |

Method 38

(S)-N$^1$-(5-Cyclopropyl-1H-pyrazol-3-yl)-4-fluoro-N$^3$-[1-(4-fluorophenyl)ethyl]-6-nitrobenzene-1,3-diamine A mixture of 5-cyclopropyl-N-(4,5-difluoro-2-nitrophenyl)-1H-pyrazol-3-amine (Method 86; 0.300 g, 1.07 mmol), (S)-1-(4-fluoro-phenyl)ethylamine (0.164 g, 1.18 mmol), and DIEA (0.280 ml, 1.61 mmol) in n-BuOH (2 ml) was heated in a sealed tube at 160° C. for 16 hrs. The solvent was removed under reduced pressure and the residue was purified by column chromatography (hexane:EtOAc=3:1) to give the title compound as an orange solid (0.360 g, 84%). NMR (400 MHz) 12.29 (s, 1H), 10.14 (s, 1H), 7.75 (d, J=12.8 Hz, 1H), 7.63 (d, J=6.4 Hz, 1H), 7.41 (m, 2H), 7.14 (t, J=8.8 Hz, 2H), 7.00 (d, J=8.0 Hz, 1H), 5.63 (s, 1H), 4.55 (m, 1H), 1.90 (m, 1H), 1.52 (d, J=6.8 Hz, 3H), 0.98 (m, 2H), 0.71 (m, 2H). MS: Calcd.: 399; Found: [M+H]$^+$ 400.

Method 39

Following a similar procedure to Method 38, the following compounds were synthesized from 5-cyclopropyl-N-(4,5-difluoro-2-nitrophenyl)-1H-pyrazol-3-amine (Method 86) and the appropriate amine.

| Meth | Product | NMR/MS | Amine |
|---|---|---|---|
| 39 | (R)-2-[5-(5-Cyclopropyl-1H-pyrazol-3-ylamino)-2-fluoro-4-nitrophenylamino]-2-(4-fluorophenyl)ethanol | (400 MHz) 12.29 (s, 1H), 10.13 (s, 1H), 7.77 (d, J=12.8 Hz, 1H), 7.41 (m, J=6.4 Hz, 3H), 7.15 (t, J=8.8 Hz, 2H), 7.04 (d, J=8.0 Hz, 1H), 5.60 (s, 1H), 5.08 (t, J=5.8 Hz, 1H), 4.45 (m, 1H), 3.62-3.80 (m, 2H), 1.90 (m, 1H), 0.98 (m, 2H), 0.71 (m, 2H). MS: Calcd.: 415; Found: [M + H]$^+$ 416. | (R)-2-amino-2-(4-fluorophenyl)ethanol |

Method 40

(R)-2-[5-Amino-4-(5-cyclopropyl-1H-pyrazol-3-ylamino)-6-methylpyrimidin-2-ylamino]-2-(4-fluorophenyl)ethanol To a suspension of (R)-2-[4-(5-cyclopropyl-1H-pyrazol-3-ylamino)-6-methyl-5-nitropyrimidin-2-ylamino]-2-(4-fluorophenyl)ethanol (Method 1, 1.0 g, 2.4 mmol) and zinc dust (0.79 g, 12.0 mmol) in the mixture of MeOH:THF (1:1, 70 ml) was slowly added saturated NH$_4$Cl solution (10 ml). After 3 hours, the reaction was treated with saturated aqueous NH$_4$OAc solution (40 ml), and the resulting mixture was stirred for 30 minutes. The reaction was then filtered through a plug of celite with EtOAc (100 ml). The resulting aqueous layer was extracted with EtOAc (2×100 ml), dried, filtered, and concentrated to give (0.8 g, 90%). MS: Calcd.: 383; Found: [M+H]$^+$ 384.

Methods 41-46

Following a similar procedure to Method 40, the following compounds were synthesized from a suitable nitro-pyrimidine.

| Meth | Compound | NMR/MS | SM |
|---|---|---|---|
| 41 | N$^4$-(5-Cyclopropyl-1H-pyrazol-3-yl)-N$^2$-[(1S)-1-(4-fluorophenyl)ethyl]pyrimidine-2,4,5-triamine | 0.70 (m, 2H), 0.96 (m 2H), 1.48 (d, J=6 Hz, 3H), 1.90 (m 1H), 5.05 (t, J=6 Hz, 1H), 6.20 (s, 1H), 7.16 (m, 2H), 7.45 (m, 2H), 8.83 (br s, 1H), 10.35 (br s, 1H). MS: Calcd.: 353; Found: [M + H]$^+$ 354.21 | Method 2 |
| 42 | (2R)-2-({5-Amino-4-[(5-cyclopropyl-1H-pyrazol-3-yl)amino]pyrimidin-2-yl}amino)-2-(4-fluorophenyl)ethanol | 0.65 (m, 2H), 0.90 (m 2H), 1.80 (m, 1H), 3.56 (m, 2H), 4.80 (m, 1H), 6.50 (s, 1H), 7.10 (m, 2H), 7.36 (m, 2H), 8.25 (br s, 1H). MS: Calcd.: 369; Found: [M + H]$^+$ 370.22 | Method 3 |
| 43 | N$^4$-(5-Cyclopropyl-1H-pyrazol-3-yl)-N$^2$-(4-fluorobenzyl)pyrimidine-2,4,5-triamine | MS: Calcd.: 339; Found: [M + H]$^+$ 340.19 | Method 4 |
| 44 | N$^4$-(5-Cyclopropyl-1H-pyrazol-3-yl)-N$^2$-[(1R)-1-(4-fluorophenyl)ethyl]pyrimidine-2,4,5-triamine | MS: Calcd.: 353; Found: [M + H]$^+$ 354.21 | Method 5 |
| 45 | (R)-2-(5-Amino-4-(5-methyl-1H-pyrazol-3-ylamino)pyrimidin-2-ylamino)-2-(4-fluorophenyl)ethanol | MS: Calcd.: 343; Found: [M + H]$^+$ 344 | Method 6 |
| 46 | (S)-N$^2$-(1-(4-Fluorophenyl)ethyl)-N$^4$-(5-isopropoxy-1H-pyrazol-3-yl)pyrimidin-2,4,5-triamine | MS: Calcd.: 371; Found: [M + H]$^+$ 372 | Method 7 |

Method 47

(S)-Ethyl 5-amino-6-(5-cyclopropyl-1H-pyrazol-3-ylamino)-2-[1-(4-fluorophenyl)ethylamino]pyrimidine-4-carboxylate To a suspension of (S)-ethyl 6-(5-cyclopropyl-1H-pyrazol-3-ylamino)-2-[1-(4-fluorophenyl)ethylamino]-5-nitropyrimidine-4-carboxylate (Method 10; 0.7 g, 1.5 mmol) and zinc dust (0.5 g, 7.7 mmol) in EtOH:THF (1:1, 20 ml) was slowly added saturated aqueous $NH_4Cl$ solution (3 ml). After 1 hour, the reaction mixture was cooled to 0° C., to which was added saturated $NH_4OAc$ solution (10 ml). The resulting mixture was allowed to stir for 10 minutes at 0° C. and then filtered through a plug of celite with EtOAc (100 ml). The resulting aqueous layer was extracted with EtOAc (2×100 ml), dried, filtered, and concentrated to give the title compound (0.60 g, 92%) which was used without further purification.

Method 48

(S)-$N^2$-(5-Cyclopropyl-1H-pyrazol-3-yl)-$N^6$-[1-(4-fluorophenyl)ethyl]pyridine-2,3,6-triamine To a suspension of (S)-$N^2$-(5-cyclopropyl-1H-pyrazol-3-yl)-$N^6$-[1-(4-fluorophenyl)ethyl]-3-nitropyridine-2,6-diamine (Method 12; 0.26 g, 0.68 mmol) and zinc dust (0.223 g, 3.41 mmol) in MeOH:THF (1:1, 12 ml) was slowly added saturated ammonium chloride solution (1.5 ml). The reaction mixture was stirred at 25° C. for 1 hour, to which was then added saturated ammonium acetate solution (5 ml). The resulting mixture was stirred for another 30 minutes. Zn dust was removed by filtration and washed with EtOAc (20 ml). The organic layer was separated, washed with brine (10 ml), dried over $Na_2SO_4$, and concentrated. The title compound was used directly for the next step without further purification.

Methods 49-61

Following a similar procedure to Method 48, the following compounds were synthesized from a suitable nitro-pyridine.

| Meth | Compound | NMR/MS | SM |
|---|---|---|---|
| 49 | $N^2$-(5-Cyclopropyl-1H-pyrazol-3-yl)-$N^6$-(4-fluorobenzyl)pyridine-2,3,6-triamine | MS: Calcd.: 338; Found: $[M + H]^+$ 339 | Method 13 |
| 50 | (2R)-2-({5-Amino-6-[(5-cyclopropyl-1H-pyrazol-3-yl)amino]pyridin-2-yl}amino)-2-(4-fluorophenyl)ethanol | MS: Calcd.: 368; Found: $[M + H]^+$ 369 | Method 14 |
| 51 | 2-({5-Amino-6-[(5-cyclopropyl-1H-pyrazol-3-yl)amino]pyridin-2-yl}amino)-2-(4-fluorophenyl)propane-1,3-diol | MS: Calcd.: 398; Found: $[M + H]^+$ 399 | Method 15 |
| 52 | 5-Chloro-$N^2$-(5-cyclopropyl-1H-pyrazol-3-yl)-$N^6$-[(1S)-1-(4-fluorophenyl)ethyl]pyridine-2,3,6-triamine | MS: Calcd.: 386; Found: $[M + H]^+$ 387 | Method 16 |
| 53 | 5-Chloro-$N^2$-(5-cyclopropyl-1H-pyrazol-3-yl)-$N^6$-(4-fluorobenzyl)pyridine-2,3,6-triamine | MS: Calcd.: 372; Found: $[M + H]^+$ 373 | Method 17 |
| 54 | (2R)-2-({5-Amino-3-chloro-6-[(5-cyclopropyl-1H-pyrazol-3-yl)amino]pyridin-2-yl}amino)-2-(4-fluorophenyl)ethanol | MS: Calcd.: 402; Found: $[M + H]^+$ 403 | Method 18 |
| 55 | (2R)-2-({5-Amino-3-chloro-6-[(5-methyl-1H-pyrazol-3-yl)amino]pyridin-2-yl}amino)-2-(4-fluorophenyl)ethanol | MS: Calcd.: 376; Found: $[M + H]^+$ 377 | Method 19 |
| 56 | (S)-$N^2$-(5-Isopropoxy-1H-pyrazol-3-yl)-$N^6$-(1-(pyridin-2-yl)ethyl)pyridine-2,3,6-triamine | MS: Calcd.: 353; Found: $[M + H]^+$ 354 | Method 20 |
| 57 | (S)-$N^6$-(1-(4-Fluorophenyl)ethyl)-$N^2$-(5-isopropoxy-1H-pyrazol-3-yl)-pyridine-2,3,6-triamine | MS: Calcd.: 370; Found: $[M + H]^+$ 371 | Method 21 |
| 58 | (R)-2-(5-Amino-6-(5-isopropoxy-1H-pyrazol-3-ylamino)pyridin-2-ylamino)-2-(4-fluorophenyl)ethanol | MS: Calcd.: 386; Found: $[M + H]^+$ 387. | Method 22 |
| 59 | (S)-5-Chloro-$N^6$-(1-(4-fluorophenyl)ethyl)-$N^2$-(5-isopropoxy-1H-pyrazol-3-yl)pyridine-2,3,6-triamine | MS: Calcd.: 404; Found: $[M + H]^+$ 405. | Method 23 |
| 60 | (S)-$N^2$-(5-Cyclopropyl-1H-pyrazol-3-yl)-$N^6$-(1-(pyridin-2-yl)ethyl)pyridine-2,3,6-triamine | MS: Calcd.: 335; Found: $[M + H]^+$ 336. | Method 24 |
| 61 | (R)-2-(5-Amino-6-(5-methyl-1H-pyrazol-3-ylamino)pyridin-2-ylamino)-2-(4-fluorophenyl)ethanol | MS: Calcd.: 342; Found: $[M + H]^+$ 343. | Method 25 |

Method 62

(S)-N³-(5-Cyclopropyl-1H-pyrazol-3-yl)-N¹-[1-(4-fluorophenyl)ethyl]benzene-1,3,4-triamine To a suspension of (S)-N³-(5-cyclopropyl-1H-pyrazol-3-yl)-N¹-[1-(4-fluorophenyl)ethyl]-4-nitrobenzene-1,3-diamine (Method 26; 0.37 g, 0.97 mmol) and Zinc dust (0.317 g, 4.85 mmol) in MeOH:THF (1:1, 24 ml) was slowly added saturated ammonium chloride (3.0 ml). The reaction mixture was stirred at 25° C. for 1 hr, to which was then added saturated ammonium acetate solution (5 ml). The resulting mixture was stirred for another 30 min. Zn dust was removed by filtration and washed with EtOAc (20 ml). The organic layer was separated, washed with brine (10 ml), dried over Na₂SO₄, and concentrated. The crude product was used directly for the next step without further purification. MS: Calcd: 351; Found: [M+H]⁺ 352.

Methods 63-68

Following a similar procedure to Method 62, the following compounds were synthesized from a suitable nitrobenzene by reduction.

| Meth | Compound | NMR/MS | SM |
|---|---|---|---|
| 63 | (2R)-2-({4-Amino-3-[(5-cyclopropyl-1H-pyrazol-3-yl)amino]phenyl}amino)-2-(4-fluorophenyl)ethanol | MS: Calcd: 367; Found: [M + H]⁺ 368 | Method 27 |
| 64 | N²-(5-Cyclopropyl-1H-pyrazol-3-yl)-N⁴-(4-fluorobenzyl)benzene-1,2,4-triamine | MS: Calcd: 337; Found: [M + H]⁺ 338 | Method 28 |
| 65 | N⁴-[(1S)-1-(4-Fluorophenyl)ethyl]-N²-(5-isopropoxy-1H-pyrazol-3-yl)benzene-1,2,4-triamine | MS: Calcd: 369; Found: [M + H]⁺ 370 | Method 29 |
| 67 | (S)-N³-(5-Cyclopropyl-1H-pyrazol-3-yl)-N¹-(1-(pyridin-2-yl)ethyl)benzene-1,3,4-triamine | MS: Calcd: 334; Found: [M + H]⁺ 335. | Method 30 |
| 68 | (R)-2-(4-Amino-3-(5-methyl-1H-pyrazol-3-ylamino)phenylamino)-2-(4-fluorophenyl)ethanol | MS: Calcd: 341; Found: [M + H]⁺ 342. | Method 31 |

Method 69

(S)-5-Amino-4-(5-cyclopropyl-1H-pyrazol-3-ylamino)-2-[1-(4-fluorophenyl)ethylamino]benzonitrile To a suspension of (S)-4-(5-cyclopropyl-1H-pyrazol-3-ylamino)-2-[1-(4-fluorophenyl)ethylamino]-5-nitrobenzonitrile (Method 32; 4.10 g, 10.1 mmol) and zinc dust (3.30 g, 50.4 mmol) in MeOH:THF (1:1, 100 ml) was slowly added saturated ammonium chloride (40 ml). The reaction mixture was stirred at 25° C. for 1 hr, to which was added saturated ammonium acetate solution (50 ml). The resulting mixture was stirred for another 30 min. The Zn dust was removed by filtration and washed with EtOAc (200 ml). The organic layer was separated, washed with brine (100 ml), dried over Na₂SO₄, and concentrated. The title compound was used directly for the next step without further purification. MS: Calcd: 376; Found: [M+H]⁺ 377.

Method 70

Following a similar procedure to Method 69, the following compounds were synthesized from a suitable nitrobenzene.

| Meth | Compound | NMR/MS | SM |
|---|---|---|---|
| 70 | 5-Amino-4-[(5-cyclopropyl-1H-pyrazol-3-yl)amino]-2-{[(1R)-1-(4-fluorophenyl)-2-hydroxyethyl]amino}benzonitrile | MS: Calcd: 392; Found: [M + H]⁺ 393 | Method 35 |

Method 71

(S)-N³-(5-Cyclopropyl-1H-pyrazol-3-yl)-2-fluoro-N¹-[1-(4-fluorophenyl)ethyl]benzene-1,3,4-triamine To a suspension of (S)-N³-(5-cyclopropyl-1H-pyrazol-3-yl)-2-fluoro-N¹-[1-(4-fluorophenyl)ethyl]-4-nitrobenzene-1,3-diamine (Method 36; 0.40 g, 1.00 mmol) and zinc dust (0.327 g, 5.00 mmol) in MeOH:THF (1:1, 10 ml) was slowly added saturated ammonium chloride (4 ml). The mixture was stirred at 25° C. for 2 hours, to which was then added saturated ammonium acetate solution (5 ml). The resulting mixture was stirred for another 30 minutes. The Zn dust was removed by filtration and washed with EtOAc (15 ml). The organic layer was separated, washed with brine, dried over Na₂SO₄, and concentrated. The title compound was used directly for the next step without further purification.

Method 72

Following a similar procedure to Method 71, the following compound was synthesized from a suitable nitrobenzene. The compound was used directly for the next step without further purification.

| Meth | Compound | SM |
|---|---|---|
| 72 | (2R)-2-({4-Amino-3-[(5-cyclopropyl-1H-pyrazol-3-yl)amino]-2-fluorophenyl}amino)-2-(4-fluorophenyl)ethanol | Method 37 |

Method 73

(S)-N³-(5-Cyclopropyl-1H-pyrazol-3-yl)-6-fluoro-N¹-[1-(4-fluorophenyl)ethyl]benzene-1,3,4-triamine To a suspension of (S)-N¹-(5-cyclopropyl-1H-pyrazol-3-yl)-4-fluoro-N³-[1-(4-fluorophenyl)ethyl]-6-nitrobenzene- 1,3-diamine (Method 38; 0.33 g, 0.826 mmol) and Zinc dust (0.270 g, 4.13 mmol) in MeOH:THF (1:1, 10 ml) was slowly added saturated ammonium chloride (4 ml). The mixture was stirred at 25° C. for 2 hrs, to which was added saturated ammonium acetate solution (5 ml). The resulting mixture was stirred for another 30 min. The Zn dust was removed by filtration and washed with EtOAc (15 ml). The organic layer was separated and dried over $Na_2SO_4$. After removal of solvent, the title compound was used directly for the next step without further purification.

Method 74

Following a similar procedure to Method 73, the following compounds were synthesized from a suitable nitrobenzene. The compound was used directly for the next step without further purification.

| Meth | Compound | SM |
|---|---|---|
| 74 | (2R)-2-({4-Amino-5-[(5-cyclopropyl-1H-pyrazol-3-yl)amino]-2-fluorophenyl}amino)-2-(4-fluorophenyl)ethanol | Method 39 |

Method 75

2-Chloro-N-(5-cyclopropyl-1H-pyrazol-3-yl)-6-methyl-5-nitropyrimidin-4-amine

A solution of 5-cyclopropyl-1H-pyrazol-3-amine (1.8 g, 14.0 mmol) in n-BuOH (25 ml) was slowly added to the n-BuOH (60 ml) solution of 2,4-dichloro-6-methyl-5-nitropyrimidine (3.0 g, 14.0 mmol) and DIEA (2.4 g, 19.0 mmol). After 5 minutes, the reaction was diluted with hexane (100 ml). The resulting precipitate was collected by filtration to yield the title compound (4.1 g, 96%). MS: Calcd.: 294; Found: $[M+H]^+$ 295.

Method 76

2-Chloro-N-(5-cyclopropyl-1H-pyrazol-3-yl)-5-nitropyrimidin-4-amine

To a solution of 2,4-dichloro-5-nitropyrimidine (3.0 g, 15 mmol) and DIEA (2.4 g, 18.5 mmol) in n-BuOH (30 ml) was slowly added 5-cyclopropyl-1H-pyrazol-3-amine (2.0 g, 16.2 mmol) at 25° C. The resulting solution was stirred at 25° C. for 5 minutes and concentrated to dryness to give the title compound (3.1 g). NMR ($CDCl_3$) 0.80 (m, 2H), 1.05 (m, 2H), 6.60 (s, 1H), 9.20 (s, 1H), 9.70 (br s, 1H), 10.40 (br s, 1H).

Method 77

6-Chloro-N-(5-cyclopropyl-1H-pyrazol-3-yl)-3-nitropyridin-2-amine

To a solution of 2,6-dichloro-3-nitropyridine (0.67 g, 3.2 mmol) and DIEA (0.46 ml, 2.65 mmol) in EtOH (20 ml) was added a 5-cyclopropyl-1H-pyrazol-3-amine (0.26 g, 2.12 mmol) solution in EtOH (5 ml) dropwise at 0° C. After addition, the reaction mixture was stirred at 25° C. for 24 hours. The solvent was removed under reduced pressure and the resulted residue was purified by column chromatography (hexane:EtOAc=5:1) to give the title compound as a yellow solid (0.58 g, 98%). NMR (400 MHz) 12.36 (s, 1H), 10.20 (s, 1H), 8.54 (d, J=8.4 Hz, 1H), 7.01 (d, J=8.4 Hz, 1H), 6.39 (d, J=1.6 Hz, 1H), 1.94 (m, 1H), 0.96 (m, 2H), 0.71 (m, 2H). MS: Calcd.: 279; Found: $[M+H]^+$ 280.

Method 78

Following a similar procedure to Method 77, the following compound was synthesized from a nitropyridine by reacting it with the appropriate amine.

| Meth | Product | NMR/MS | Amine |
|---|---|---|---|
| 78 | 6-Chloro-N-(5-methyl-1H-pyrazol-3-yl)-3-nitropyridin-2-amine | (400 MHz) 12.36 (s, 1H), 10.24 (s, 1H), 8.55 (d, J=8.8 Hz, 1H), 7.02 (d, J=8.8 Hz, 1H), 6.48 (s, 1H), 2.27 (s, 3H). MS: Calcd.: 253; Found: $[M + H]^+$ 254. | 5-methyl-1H-pyrazol-3-amine |

Method 79

5,6-Chloro-N-(5-cyclopropyl-1H-pyrazol-3-yl)-3-nitropyridine-2-amine

To a solution of 2,3,6-trichloro-5-nitropyridine (1.62 g, 7.10 mmol) and DIEA (1.24 ml, 7.1 mmol) in THF (25 ml) was added dropwise a solution of 5-cyclopropyl-1H-pyrazol-3-amine (0.70 g, 5.68 mmol) in THF (5 ml) at 0° C. After addition, the reaction mixture was stirred at 25° C. for 24 hours. The solvent was removed under reduced pressure and the resulted residue was purified by column chromatography (hexane:EtOAc=1.5:1) to give the title compound as a yellow solid (0.83 g, 47%). NMR (400 MHz) 12.39 (s, 1H), 10.12 (s, 1H), 8.77 (d, J=1.2 Hz, 1H), 6.35 (s, 1H), 1.95 (m, 1H), 0.96 (m, 2H), 0.71 (m, 2H). MS: Calcd.: 313; Found: $[M+H]^+$ 314.

Methods 80-81

Following a similar procedure to Method 79, the following compounds were synthesized from a 2,3,6-trichloro-5-nitropyridine by reacting it with the appropriate amine.

| Meth | Product | NMR/MS | Amine |
|---|---|---|---|
| 80 | (R)-2-(3,6-Dichloro-5-nitropyridin-2-ylamino)-2-(4-fluorophenyl) ethanol | (400 MHz) 8.46 (s, 1H), 8.22 (d, J=8.0 Hz, 1H), 7.45 (m, 2H), 7.16 (m, 2H), 5.22 (m, 1H), 5.05 (t, J=6.0 Hz, 1H), 3.87 (m, 1H), 3.72 (m, 1H) | (R)-2-amino-2-(4-fluoro phenyl)ethanol |
| 81 | 5,6-Chloro-N-(5-isopropoxy-1H-pyrazol-3-yl)-3-nitropyridine-2-amine | (400 MHz) 12.26 and 11.64 (s, 1H), 10.42 and 10.04 (s, 1H), 8.81 and 8.77 (s, 1H), 6.02 and 5.94 (s, 1H), 4.70 and 4.48 (m, 1H), 1.32 and 1.27 (d, J=6.0 Hz, 6H). MS: Calcd.: 331; Found: [M + H]+ 332. | 5-isopropoxy-1H-pyrazol-3-amine |

Method 82

5-Cyclopropyl-N-(5-fluoro-2-nitrophenyl)-1H-pyrazol-3-amine

To a solution of 2,4-difluoro-1-nitrobenzene (1.76 g, 11.1 mmol) and DIEA (1.93 ml, 11.1 mmol) in THF (20 ml) was added dropwise a solution of 5-cyclopropyl-1H-pyrazol-3-amine (0.91 g, 7.39 mmol) in THF (5 ml) at 25° C. After addition, the reaction mixture was stirred at 80° C. for 48 hours. The solvent was removed under reduced pressure and the resulted residue was purified by column chromatography (hexane:DCM:EtOAc=2:1:1) to give the title compound as a yellow solid (0.62 g, 32%). NMR (400 MHz) 12.37 (s, 1H), 9.83 (s, 1H), 8.25 (m, 1H), 7.98 (d, J=11.2 Hz, 1H), 6.75 (m, 1H), 5.95 (s, 1H), 1.90 (m, 1H), 0.96 (m, 2H), 0.72 (m, 2H).

Methods 83-84

Following a similar procedure to Method 82 the following compounds were synthesized from 2,4-difluoro-1-nitrobenzene and the appropriate amine.

| Meth | Product | NMR/MS | Amine |
|---|---|---|---|
| 83 | N-(5-Fluoro-2-nitrophenyl)-5-isopropoxyl-1H-pyrazol-3-amine | MS: Calcd.: 280; Found: [M + H]+ 281 | 5-isopropoxyl-1H-pyrazol-3-amine |
| 84 | 5-Methyl-N-(5-fluoro-2-nitrophenyl)-1H-pyrazol-3-amine | (400 MHz) 12.34 (s, 1H), 9.85 (s, 1H), 8.25 (m, 1H), 7.99 (dd, J=12.8 and 2.8 Hz, 1H), 6.75 (m, 1H), 6.03 (d, J=2.0 Hz, 1H), 2.24 (s, 3H). MS: Calcd.: 236; Found: [M + H]+ 237. | 5-methyl-1H-pyrazol-3-amine |

Method 85

5-Cyclopropyl-N-(2,3-difluoro-6-nitrophenyl)-1H-pyrazol-3-amine

To a solution of 1,2,3-trifluoro-4-nitrobenzene (3.2 g, 18 mmol) and DIEA (4.2 ml, 24 mmol) in dry THF (20 ml) was added dropwise a solution of 5-cyclopropyl-1H-pyrazol-3-amine (2.0 g, 16 mmol) in THF (5 ml) at 0° C. After addition, the reaction mixture was stirred at 25° C. for 21 hours. The solvent was removed under reduced pressure and the resulted residue was purified by column chromatography (hexane:EtOAc=5:2). Recrystallization from EtOAc (10 ml) and hexanes (~100 ml) gave the title compound as red crystals (1.5 g, 33%). NMR (400 MHz) 11.90 (s, 1H), 8.78 (s, 1H), 7.86 (t, J=7.6 Hz, 1H), 7.08 (q, J=8.7 Hz, 1H), 5.60 (s, 1H), 1.83 (m, 1H), 0.89 (m, 2H), 0.65 (m, 2H). MS: Calcd.: 280; Found: [M+H]+ 281.

Method 86

5-Cyclopropyl-N-(4,5-difluoro-2-nitrophenyl)-1H-pyrazol-3-amine

To a solution of 1,2,4-trifluoro-5-nitrobenzene (3.0 g, 18 mmol) and DIEA (4.2 ml, 24 mmol) in dry THF (20 ml) was added dropwise a solution of 5-cyclopropyl-1H-pyrazol-3-amine (2.0 g, 16 mmol) in THF (5 ml) at 0° C. After addition, the reaction mixture was stirred at 25° C. for 20 hrs. It was then heated to 40° C. for 40 hrs. The solvent was removed under reduced pressure and the resulted residue was purified by column chromatography (hexane:EtOAc=5:2). Recrystallization from EtOAc (10 ml) and hexanes (~100 ml) gave the title compound as red crystals (0.8 g, 18%). NMR (400 MHz) 12.36 (s, 1H), 9.79 (s, 1H), 8.27 (m, 2H), 5.93 (s, 1H), 1.90 (m, 1H), 0.93 (m, 2H), 0.72 (m, 2H). MS: Calcd.: 280; Found: [M+H]+ 281.

Method 87

2-Chloro-N-(5-isopropoxy-1H-pyrazol-3-yl)-5-nitropyrimidin-4-amine

To a solution of 2,4-dichloro-5-nitropyrimidine (0.41 g, 2.1 mmol) and DIEA (0.31 ml, 1.8 mmol) in THF (10 ml) was added 5-isopropoxy-1H-pyrazol-3-amine (0.20 g, 1.4 mmol) at 0° C. The reaction mixture was stirred at 0° C. for 1 hour. The solvent was removed under reduced pressure and the resulted residue was purified by column chromatography (DCM:EtOAc=2.5:1) to give the title compound as a yellow solid (0.19 g, 45%). MS: Calcd.: 298; Found: [M+H]$^+$ 299.

Method 88

(S)-N$^4$-(5-Cyclopropyl-1H-pyrazol-3-yl)-N$^2$-(1-(4-fluorophenyl)ethyl)pyridine-2,4,5-triamine To a suspension of (S)-N$^4$-(5-cyclopropyl-1H-pyrazol-3-yl)-N$^2$-(1-(4-fluorophenyl)ethyl)-5-nitropyridine-2,4-diamine (Method 89, 0.15 g, 0.40 mmol) and zinc dust (0.13 g, 2.0 mmol) in MeOH-THF (1:1, 16 ml) was slowly added saturated ammonium chloride solution (2 ml). The reaction mixture was stirred at 25° C. for 1 hour, to which was added saturated ammonium acetate solution (5 ml). The resulting mixture was stirred for another 30 min. Zn dust was removed by filtration and washed with EtOAc (20 ml). The organic layer was separated, washed with brine (10 ml), dried over Na$_2$SO$_4$, and concentrated. The crude product was used directly for the next step without further purification. MS: Calcd.: 352; Found: [M+H]$^+$ 353.

Method 89

(S)-N$^4$-(5-Cyclopropyl-1H-pyrazol-3-yl)-N$^2$-(1-(4-fluorophenyl)ethyl)-5-nitropyridine-2,4-diamine A mixture of 2-chloro-N-(5-cyclopropyl-1H-pyrazol-3-yl)-5-nitropyridin-4-amine (Method 90, 0.15 g, 0.54 mmol), (S)-1-(4-fluoro-phenyl)-ethylamine (0.093 g, 0.67 mmol), and DIEA (0.12 ml, 0.67 mmol) in n-BuOH (5 ml) was heated in a sealed tube at 180° C. for 32 hours. The solvent was removed under reduced pressure and the residue was purified by column chromatography (hexane-EtOAc=1:1) to give the title compound as a yellow solid (0.168 g, 82%). $^1$H NMR (400 MHz) 12.37 (s, 1H), 9.59 (b, 1H), 8.83 (s, 1H), 8.20 (b, 1H), 7.37 (m, 2H), 7.13 (m, 2H), 6.69 (b, 1H), 5.88 (b, 1H), 5.29 (m, 1H), 1.91 (m, 1H), 1.43 (d, J=6.4 Hz, 3H), 0.97 (m, 2H), 0.71 (m 2H). MS: Calcd.: 382; Found: [M+H]$^+$ 383.

Method 90

2-Chloro-N-(5-cyclopropyl-1H-pyrazol-3-yl)-5-nitropyridin-4-amine

To a solution of 2,4-dichloro-5-nitropyridine (Method 91, 0.42 g, 2.18 mmol) and DIEA (0.46 ml, 2.61 mmol) in THF (10 ml) was added a 5-cyclopropyl-1H-pyrazol-3-amine (0.31 g, 2.50 mmol) solution in THF (5 ml) drop wise at 0° C. After addition, the reaction mixture was stirred at 25° C. for 17 hours. The solvent was removed under reduced pressure and the resulted residue was purified by column chromatography (hexane:EtOAc=3:1) to give the title compound as a yellow solid (0.54 g, 89%). $^1$H NMR (400 MHz) 12.55 (s, 1H), 9.95 (s, 1H), 8.97 (s, 1H), 8.09 (s, 1H), 6.02 (d, J=2.0 Hz, 1H), 1.93 (m, 1H), 0.97 (m, 2H), 0.71 (m, 2H). MS: Calcd.: 279; Found: [M+H]$^+$ 280.

Method 91

2,4-Dichloro-5-nitropyridine

To 4-chloro-5-nitropyridine-2-amine (Method 92, 4.40 g, 21.0 mmol) in concentrated HCl (70 ml) was added sodium nitrite (4.36 g, 63.1 mmol) potion wise at 0-5° C. After 1 hour at 0-5° C., the reaction was warmed to room temperature and stirred for 50 hours. Ice (100 g) was added and the mixture was extracted with ether (2×50 ml) and dried over sodium sulfate. The solvent was removed under reduced pressure and the resulted residue was purified by column chromatography (hexane-DCM=1:5) to give the title compound as a white solid (1.47 g, 33%). $^1$H NMR (400 MHz) 9.18 (s, 1H), 8.22 (s, 1H).

Method 92

4-Chloro-5-nitropyridine-2-amine

To 4-chloro-3-nitropyridine (10.0 g, 63.1 mmol) in 500 ml of liquid ammonium was added potassium permanganate (19.9 g, 126.1 mmol). The reaction was stirred at this temperature (−33° C.) for 5 hours then slowly warmed to room temperature. After evaporation of ammonia, water (1 L) was added. The solid formed was collected by filtration and washed with water (2 L). The solid was extracted with 1:1=DCM:EtOAc (5×500 ml). The solvent was removed and the resulting solid was recrystallized from EtOAc (400 ml) to give the title compound as a yellow solid (4.4 g, 33%). $^1$H NMR (400 MHz) 8.88 (s, 1H), 7.65 (b, 2H), 6.62 (s, 1H).

Method 93

(R)-2-(5-Amino-4-(5-cyclopropyl-1H-pyrazol-3-ylamino)pyridin-2-ylamino)-2-(4-fluorophenyl)ethanol To a suspension of (R)-2-(4-(5-cyclopropyl-1H-pyrazol-3-ylamino)-5-nitropyridin-2-ylamino)-2-(4-fluorophenyl) ethanol (Method 94, 0.14 g, 0.36 mmol) and zinc dust (0.12 g, 1.78 mmol) in MeOH-THF (1:1, 16 ml) was slowly added saturated ammonium chloride (2.0 ml). The reaction mixture was stirred at 25° C. for 1 hour, to which was then added saturated ammonium acetate solution (5 ml). The resulting mixture was stirred for another 30 minutes. The Zn dust was removed by filtration and washed with EtOAc (20 ml). The organic layer was separated, washed with brine (10 ml), dried over sodium sulfate, and concentrated. The crude product was used directly for the next step without further purification. MS: Calcd.: 368; Found: [M+H]$^+$ 369.

Method 94

(R)-2-(4-(5-Cyclopropyl-1H-pyrazol-3-ylamino)-5-nitropyridin-2-ylamino)-2-(4-fluorophenyl)ethanol A mixture of 2-chloro-N-(5-cyclopropyl-1H-pyrazol-3-yl)-5-nitropyridin-4-amine (Method 90, 0.15 g, 0.54 mmol), (R)-2-amino-2-(4-fluorophenyl)ethanol (0.10 g, 0.67 mmol), and DIEA (0.12 ml, 0.67 mmol) in n-BuOH (5 ml) was heated in a sealed tube at 195° C. for 52 hours. The solvent was removed under reduced pressure and the residue was purified by column chromatography (EtOAc) to give the title compound as a yellow solid (0.15 g, 72%). $^1$H NMR (400 MHz) 12.38 (s, 1H), 9.59 (b, 1H), 8.83 (s, 1H), 8.16 (b, 11H), 7.37 (m, 2H), 7.13 (m, 2H), 6.75 (b, 1H), 5.92 (b, 11H), 5.25 (b, 1H), 4.98 (m, 1H), 3.61 (t, J=6.4 Hz, 2H), 1.92 (m, 1H), 0.97 (m, 2H), 0.72 (m, 2H). MS: Calcd.: 398; Found: [M+H]$^+$ 399.

Method 95

6-Chloro-N-(5-isopropoxy-1H-pyrazol-3-yl)-3-nitropyridin-2-amine

To a solution of 2,6-dichloro-3-nitropyridine (1.0 g, 5.3 mmol) and DIEA (0.77 ml, 4.4 mmol) in THF (20 ml) was added 5-isopropoxy-1H-pyrazol-3-amine (0.50 g, 3.5 mmol). The reaction mixture was stirred at 25° C. for 3 days and 60° C. for 1 hour. The solvent was removed under reduced pressure and the resulted residue was purified by column chromatography (hexane-EtOAc=3:1) to give the title compound as a yellow solid (0.62 g, 59%). $^1$H NMR (400 MHz) 12.25 and 11.66 (s, 1H), 10.46 and 10.13 (s, 1H), 8.56 (m, 1H), 7.11 and 7.02 (d, J=8.4 Hz, 1H), 6.08 and 5.97 (s, 1H), 4.70 and 4.48 (m, 1H), 1.32 and 1.27 (d, J=6.0 Hz, 6H). MS: Calcd.: 297; Found: [M+H]$^+$ 298.

Method 96

(S)-2-Amino-3-(5-cyclopropyl-1H-pyrazol-3-ylamino)-5-(1-(4-fluorophenyl)ethylamino)benzonitrile To a suspension of (S)-3-(5-cyclopropyl-1H-pyrazol-3-ylamino)-5-(1-(4-fluorophenyl)ethylamino)-2-nitrobenzonitrile (Method 97, 4.20 g, 10.0 mmol) and zinc dust (3.40 g, 52 mmol) in MeOH-THF (1:1, 100 ml) was slowly added saturated ammonium chloride (40 ml). The reaction mixture was stirred at 25° C. for 1 hour, to which was then added saturated ammonium acetate solution (50 ml). The resulting mixture was stirred for another 30 minutes. Zn dust was removed by filtration and washed with EtOAc (200 ml). The organic layer was separated, washed with brine (100 ml), dried over sodium sulfate, and concentrated. The crude product was used directly for the next step without further purification. MS: Calcd: 376; Found: [M+H]$^+$ 377.

Method 97

(S)-3-(5-Cyclopropyl-1H-pyrazol-3-ylamino)-5-(1-(4-fluorophenyl)ethylamino)-2-nitrobenzonitrile A mixture of 3-(5-cyclopropyl-1H-pyrazol-3-ylamino)-5-fluoro-2-nitrobenzonitrile (Method 98, 3.50 g, 12.2 mmol), (S)-1-(4-fluoro-phenyl)ethylamine (1.87 g, 13.4 mmol), and DIEA (2.6 ml, 14.6 mmol) in n-BuOH (20 ml) was heated in a sealed tube at 230° C. for 2 hours. The solvent was removed under reduced pressure and the residue was purified by column chromatography (hexane-EtOAc=1:2) to give the title compound as a yellow solid (4.4 g, 89%). $^1$H NMR (400 MHz) 12.38 (s, 1H), 10.12 (b, 1H), 8.07 (d, J=6.4 Hz, 1H), 7.34 (m, 2H), 7.16 (m, 2H), 6.89 (b, 1H), 6.77 (s, 1H), 5.63 (m, 1H), 4.55 (m, 1H), 1.90 (m, 1H), 1.45 (d, J=6.8 Hz, 3H), 0.97 (m, 2H), 0.70 (m 2H). MS: Calcd.: 406; Found: [M+H]$^+$ 407.

Method 98

3-(5-Cyclopropyl-1H-pyrazol-3-ylamino)-5-fluoro-2-nitrobenzonitrile

To a solution of 3,5-difluoro-2-nitrobenzonitrile (Method 99, 5.8 g, 31.5 mmol) and DIEA (5.5 ml, 31.5 mmol) in THF (50 ml) was added drop wise a solution of 5-cyclopropyl-1H-pyrazol-3-amine (4.66 g, 37.8 mmol) in THF (5 ml) at 0° C. After addition, the reaction mixture was stirred at 25° C. for 20 hours. The solvent was removed under reduced pressure and the resulted residue was purified by column chromatography (DCM-EtOAc=10:1) to give the title compound as a yellow solid (5.5 g, 61%). $^1$H NMR (400 MHz) 12.43 (s, 1H), 9.70 (s, 1H), 8.22 (dd, J=11.2 and 2.0 Hz, 1H), 7.51 (d, J=5.2 Hz, 1H), 5.92 (s, 1H), 1.90 (m, 1H), 0.95 (m, 2H), 0.71 (m, 2H). MS: Calcd.: 287; Found: [M+H]$^+$ 288.

Method 99

3,5-Difluoro-2-nitrobenzonitrile

Potassium nitrate (6.56 g, 64.8 mmol) was added to concentrated $H_2SO_4$ (33.7 ml, 633 mmol) at 0° C., followed by slow addition of 3,5-difluorobenzonitrile (4.4 g, 31.6 mmol). The suspension was stirred at this temperature for an additional 3 hours and quenched with ice water (500 ml). The resulting solid was collected by filtration and dried to give the title compound (5.55 g, 95%) as a white solid. $^1$H NMR (400 MHz, CDCl$_3$) 7.43 (m, 1H), 7.35 (m, 1H).

Method 100

(S)-2-Amino-3-(5-cyclopropyl-1H-pyrazol-3-ylamino)-5-(1-(4-fluorophenyl)ethylamino)benzamide To a suspension of (S)-3-(5-cyclopropyl-1H-pyrazol-3-ylamino)-5-(1-(4-fluorophenyl)ethylamino)-2-nitrobenzonitrile (Method 97; 4.20 g, 10.0 mmol) and zinc dust (3.40 g, 52 mmol) in MeOH-THF (1:1, 100 ml) was slowly added saturated ammonium chloride (40 ml). The reaction mixture was stirred at 25° C. for 1 hour, to which was then added saturated ammonium acetate solution (50 ml). The resulting mixture was stirred for another 30 minutes. Zn dust was removed by filtration and washed with EtOAc (200 ml). The organic layer was separated, washed with brine (100 ml), dried over sodium sulfate, and concentrated. The crude product was used directly for the next step without further purification. MS: Calcd: 394; Found: [M+H]$^+$ 395.

Method 101

(S)-N$^3$-(5-Cyclopropyl-1H-pyrazol-3-yl)-2,6-difluoro-N$^1$-(1-(4-fluorophenyl)ethyl)benzene-1,3,4-triamine A solution of saturated ammonium chloride (4 ml) was added slowly to a suspension of (S)-N$^1$-(5-cyclopropyl-1H-pyrazol-3-yl)-2,4-difluoro-N$^3$-(1-(4-fluorophenyl)ethyl)-6-nitrobenzene-1,3-diamine (Method 102, 0.30 g, 0.719 mmol) and zinc dust (0.235 g, 3.59 mmol) in MeOH/THF (10 ml, 1:1). The mixture was stirred at 25° C. for 2 hours. Saturated ammonium acetate solution (5 ml) was added and the mixture was stirred for another 30 minutes. Zn dust was removed by filtration and the cake was washed with EtOAc (15 ml). The organic layer was separated and dried over sodium sulfate. After removal of solvent, the product was used directly for the next step without further purification.

Method 102

(S)-N$^1$-(5-Cyclopropyl-1H-pyrazol-3-yl)-2,4-difluoro-N$^3$-(1-(4-fluorophenyl)ethyl)-6-nitrobenzene-1,3-diamine A mixture of 5-cyclopropyl-N-(2,3,4-trifluoro-6-nitrophenyl)-1H-pyrazol-3-amine (Method 103, 0.300 g, 1.01 mmol), (S)-1-(4-fluorophenyl)ethylamine (0.154 g, 1.11 mmol) and DIEA (0.263 ml, 1.51 mmol) in n-BuOH (2 ml) was heated in a sealed tube placed in an oil bath set at 135° C. for 8 hours. The solvent was removed under reduced pressure and the residue was purified by chromatography (hexane-EtOAc=3:1) to give the title compound as an orange solid (0.30 g, 71%). $^1$H NMR (400 MHz) 11.89 (s, 1H), 8.57 (s, 1H), 7.69 (d, 1H, J=13.6 Hz), 7.35 (m, 2H), 7.14 (t, J=8.8 Hz, 2H), 6.81 (d, 1H, 7.6 Hz), 5.39 (s, 1H), 5.00 (m, 1H), 1.80 (m, 1H), 1.49 (d, J=6.8 Hz, 3H), 0.90 (m, 2H), 0.62 (m, 2H). MS: Calcd.: 417; Found: [M+H]$^+$ 418.

Method 103

5-Cyclopropyl-N-(2,3,4-trifluoro-6-nitrophenyl)-1H-pyrazol-3-amine

To 1,2,3,4-tetrafluoro-5-nitrobenzene (3.0 g, 15.4 mmol) and DIEA (3.7 ml, 21.0 mmol) in dry THF (20 ml) was added 5-cyclopropyl-1H-pyrazol-3-amine (1.7 g, 14.0 mmol) in THF (5 ml) drop wise at 0° C. After addition, the reaction mixture was stirred at 25° C. for 16 hours. The solvent was removed under reduced pressure and the resulted residue was purified by column chromatography (hexane-EtOAc=4:1). This was recrystallized from Et$_2$O (20 ml) and hexanes (~150 ml) to give the title compound as red crystals (0.650 g, 16%). $^1$H NMR (400 MHz) 11.84 (s, 1H), 8.67 (s, 1H), 8.06 (m, 1H), 5.57 (s, 1H), 1.82 (m, 1H), 0.89 (m, 2H), 0.65 (m, 2H). MS: Calcd.: 298; Found: [M+H]$^+$ 299.

Method 104

(R)-2-(4-Amino-3-(5-cyclopropyl-1H-pyrazol-3-ylamino)-2,6-difluorophenylamino)-2-(4-fluorophenyl)ethanol A solution of saturated ammonium chloride (4 ml) was added slowly to a suspension (R)-2-(3-(5-cyclopropyl-1H-pyrazol-3-ylamino)-2,6-difluoro-4-nitrophenylamino)-2-(4-fluorophenyl)ethanol (Method 105, 0.250 g, 0.577 mmol) and zinc dust (0.189 g, 2.88 mmol) in MeOH/THF (10 ml, 1:1). The mixture was stirred at 25° C. for 5 minutes. Saturated ammonium acetate solution (5 ml) was added and the mixture was stirred for another 30 minutes. Zn dust was removed by filtration and the cake was washed with EtOAc (15 ml). The organic layer was separated and dried over sodium sulfate. After removal of solvent, the product was used directly for the next step without further purification.

Method 105

(R)-2-(3-(5-Cyclopropyl-1H-pyrazol-3-ylamino)-2,6-difluoro-4-nitrophenylamino)-2-(4-fluorophenyl)ethanol A mixture of 5-cyclopropyl-N-(2,3,4-trifluoro-6-nitrophenyl)-1H-pyrazol-3-amine (Method 103, 0.300 g, 1.01 mmol), (R)-2-amino-2-(4-fluorophenyl)ethanol (0.172 g, 1.11 mmol) and DIEA (0.263 ml, 1.51 mmol) in n-BuOH (2 ml) was heated in a sealed tube placed in an oil bath set at 135° C. for 8 hours. The solvent was removed under reduced pressure and the residue was purified by chromatography (hexane-EtOAc=1:1) to give the title compound as an orange solid (0.25 g, 57%). $^1$H NMR (400 MHz) 11.88 (s, 1H), 8.57 (s, 1H), 7.70 (d, J=13.2 Hz, 1H), 7.34 (m, 2H), 7.15 (t, J=8.8 Hz, 2H), 6.61 (b, 1H), 5.38 (s, 1H), 5.07 (t, J=5.6 Hz, 1H), 4.88 (m, 1H), 3.62-3.71 (m, 2H), 1.80 (m, 1H), 0.90 (m, 2H), 0.61 (m, 2H). MS: Calcd.: 433; Found: [M+H]$^+$ 434.

Utility

The compounds of the present invention have utility for the treatment of cancer by inhibiting the tyrosine kinases, particularly the Trks and more particularly Trk A and B. Methods of treatment target tyrosine kinase activity, particularly the Trk activity and more particularly Trk A and B activity, which is involved in a variety of cancer related processes. Thus, inhibitors of tyrosine kinase, particularly the Trks and more particularly Trk A and B, are expected to be active against neoplastic disease such as carcinoma of the breast, ovary, lung, colon, prostate or other tissues, as well as leukemias and lymphomas, tumours of the central and peripheral nervous system, and other tumour types such as melanoma, fibrosarcoma and osteosarcoma. Tyrosine kinase inhibitors, particularly the Trk inhibitors and more particularly Trk A and B inhibitors are also expected to be useful for the treatment other proliferative diseases including but not limited to autoimmune, inflammatory, neurological, and cardiovascular diseases.

In addition, the compounds of the invention are expected to be of value in the treatment or prophylaxis of cancers selected with up regulated of constitutively activated Trk kinases, including but not limited to, oncogenic rearrangements leading to ETV6-TrkC fusions, TRP-TrkA fusions proteins, AML-ETO (t8;21), autocrine or paracrine signalling leading to elevated serum levels of NGF, BDNF, neurotropins or tumours with constitutively active Trk associated with disease aggressiveness, tumour growth and proliferation or survival signalling.

Compounds of the present invention have been shown to inhibit tyrosine kinases, particularly the Trks and more particularly Trk A and B, as determined by the Trk A Assay described herein.

Compounds provided by this invention should also be useful as standards and reagents in determining the ability of a potential pharmaceutical to inhibit tyrosine kinases, particularly the Trks and more particularly Trk A and B. These would be provided in commercial kits comprising a compound of this invention Trk A Assay Format Trk A kinase activity was measured for its ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure Trk A kinase activity, the intracellular domain of a HIS-tagged human Trk A kinase (amino acids 442-796 of Trk A, Swiss-Prot Primary Accession Number P04629) was expressed in SF9 cells and purified using standard nickel column chromatography. After incubation of the kinase with a biotinylated substrate and adenosine triphosphate (ATP) for 20 minutes at room temperature, the kinase reaction was stopped by the addition of 30 mM ethylenediaminetetraacetic acid (EDTA). The reaction was performed in 384 well microtitre plates and the reaction products were detected with the addition of strepavidin coated Donor Beads and phosphotyrosine-specific antibodies coated Acceptor Beads using the EnVision Multilabel Plate Reader after an overnight incubation at room temperature.

| | |
|---|---|
| Peptide substrate | PolyEY-biotin (PGT-bio.) |
| ATP Km | 70 µM |
| Assay conditions | 0.838 ng/ml Trk A, 9 mM HEPES, 45 µg/ml BSA, 10 mM MnCl$_2$, 5 nM PGT-bio, 0.01% Triton ® X-100, 70 µM ATP |
| Incubation | 20 minutes, room temperature |
| Termination/Detection conditions | 6.3 mM HEPES, 30 mM EDTA, 525 µg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nM Emission = 570 nM Excitation Time = 180 ms Total Measurement Time = 550 ms |

Although the pharmacological properties of the compounds of the formula (I) vary with structural change, in general activity possessed by compounds of the formula (I) may be demonstrated at $IC_{50}$ concentrations (concentrations to achieve 50% inhibition) or doses in the range of (0.01 μM to 10 μM).

When tested in the above in-vitro assay the Trk inhibitory activity of the following examples was measured at the following $IC_{50}$s.

| Ex | $IC_{50}$ (μM) |
|---|---|
| Example 4 | 0.020 |
| Example 14 | 0.022 |
| Example 29 | 0.015 |

The invention claimed is:
1. A compound of formula (I):

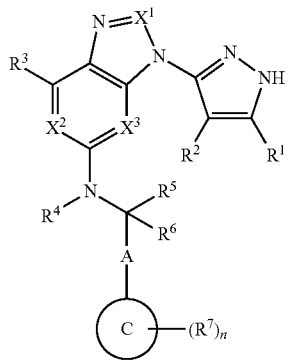

(I)

wherein:
$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^8$; and wherein if said heterocyclyl contains an —NH— moiety that nitrogen may be optionally substituted by a group selected from $R^9$;
$X^1$ is C or N;
$X^2$ is C;
$X^3$ is N,
$R^3$ and $R^{10}$ are independently selected from hydrogen, halo, nitro, cyano, hydroxy, trifluoromethoxy, amino, carboxy, carbamoyl, mercapto, sulphamoyl, $C_{1-6}$ alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{11}$— or heterocyclyl-$R^{12}$—; wherein $R^3$ and $R^{10}$ independently of each other may be optionally substituted on carbon by one or more $R^{13}$; and wherein if said heterocyclyl contains an —NH— moiety that nitrogen may be optionally substituted by a group selected from $R^{14}$;

$R^4$ is hydrogen or optionally substituted $C_{1-6}$alkyl; wherein said optional substituents are selected from one or more $R^{15}$;
$R^5$ and $R^6$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$ alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ and $R^6$ independently of each other may be optionally substituted on carbon by one or more $R^{16}$; and wherein if said heterocyclyl contains an —NH— moiety that nitrogen may be optionally substituted by a group selected from $R^{17}$;
A is a direct bond or $C_{1-2}$alkylene; wherein said $C_{1-2}$alkylene may be optionally substituted by one or more $R^{18}$;
Ring C is carbocyclyl or heterocyclyl; wherein if said heterocyclyl contains an —NH— moiety that nitrogen may be optionally substituted by a group selected from $R^{19}$;
$R^7$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$ alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^7$ may be optionally substituted on carbon by one or more $R^{20}$; and wherein if said heterocyclyl contains an —NH— moiety that nitrogen may be optionally substituted by a group selected from $R^{21}$; n is 0, 1, 2 or 3; wherein the values of $R^7$ may be the same or different;
$R^8$, $R^{13}$, $R^{15}$, $R^{16}$, $R^{18}$ and $R^{20}$ and are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{22}$— or heterocyclyl-$R^{23}$—; wherein $R^8$, $R^{13}$, $R^{15}$, $R^{16}$, $R^{18}$ and $R^{20}$ independently of each other may be optionally substituted on carbon by one or more $R^{24}$; and wherein if said heterocyclyl contains an —NH— moiety that nitrogen may be optionally substituted by a group selected from $R^{25}$;
$R^9$, $R^{14}$, $R^{17}$, $R^{19}$, $R^{21}$, $R^{25}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^9$, $R^{14}$, $R^{17}$, $R^{19}$, $R^{21}$ and $R^{25}$ independently of each other may be optionally substituted on carbon by on or more $R^{26}$;
$R^{24}$ and $R^{26}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, carbocyclyl or heterocyclyl; wherein $R^{24}$ and $R^{26}$ independently of each other may be optionally substituted on carbon by one or more $R^{27}$; and wherein if said heterocyclyl contains an —NH— moiety that nitrogen may be optionally substituted by a group selected from $R^{28}$;

$R^{11}$, $R^{12}$, $R^{22}$ and $R^{23}$ are independently selected from a direct bond, —O—, —N($R^{29}$)—, —C(O)—, —N($R^{30}$)C(O)—, —C(O)N($R^{31}$)—, —S(O)$_S$—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$salkyl and s is 0-2;

$R^{27}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-d iethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-d imethylsulphamoyl, N,N-diethylsulphamoyl or N-methyl-N-ethylsulphamoyl; and $R^{28}$ is selected from $C_{1-6}$alkyl, $C_{1-6}$alkanoyl, $C_{1-6}$alkylsulphonyl, $C_{1-6}$alkoxycarbonyl, carbamoyl, N—$(C_{1-6}$ alkyl)carbamoyl, N,N—$(C_{1-6}$alkyl)carbamoyl, benzyl, benzyloxycarbonyl, benzoyl and phenylsulphonyl;

or a pharmaceutically acceptable salt thereof.

2. A compound of formula (I) or a pharmaceutically acceptable salt thereof, as claimed in claim 1 wherein $R^1$ is selected from $C_{1-6}$alkyl, $C_{1-6}$alkoxy and carbocyclyl.

3. A compound of formula (I) or a pharmaceutically acceptable salt thereof, as claimed in claim 1 wherein $R^2$ is hydrogen.

4. A compound of formula (I) or a pharmaceutically acceptable salt thereof, as claimed in claim 1 wherein $R^3$ is selected from hydrogen, cyano, carbamoyl, $C_{1-6}$alkyl and $C_{1-6}$alkoxycarbonyl; wherein $R^3$ may be optionally substituted on carbon by one or more $R^{13}$; and $R^{13}$ is hydroxy.

5. A compound of formula (I) or a pharmaceutically acceptable salt thereof, as claimed in claim 1 wherein $R^4$ is hydrogen.

6. A compound of formula (I) or a pharmaceutically acceptable salt thereof, as claimed in claim 1 wherein $R^5$ and $R^6$ are independently selected from hydrogen or $C_{1-6}$alkyl; wherein $R^5$ and $R^6$ independently of each other may be optionally substituted on carbon by one or more $R^{16}$; wherein $R^{16}$ is hydroxy.

7. A compound of formula (I) or a pharmaceutically acceptable salt thereof, as claimed in claim 1 wherein A is a direct bond or $C_{1-2}$alkylene; wherein said $C_{1-2}$alkylene may be optionally substituted by one or more $R^{18}$; wherein $R^{18}$ is hydroxy.

8. A compound of formula (I) or a pharmaceutically acceptable salt thereof, as claimed in claim 1 wherein Ring C is phenyl, pyridyl, 1,3-benzodioxolyl or 1 H-indolyl.

9. A compound of formula (I) or a pharmaceutically acceptable salt thereof, as claimed in claim 1 wherein $R^7$ is selected from halo and $C_{1-6}$alkyl; wherein $R^7$ may be optionally substituted on carbon by one or more $R^{20}$; wherein $R°$ is halo.

10. A compound of formula (I) or a pharmaceutically acceptable salt thereof, as claimed in claim 1 wherein n is 0, 1 or 2; wherein the values of $R^7$ may be the same or different.

11. A compound of formula (I):

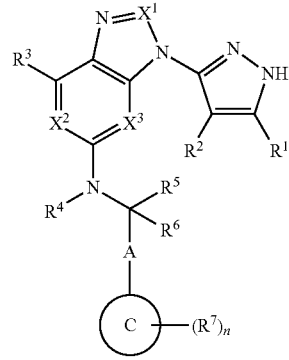

wherein:
$R^1$ is selected from methyl, isopropoxy and cyclopropyl;
$R^2$ is hydrogen;
$X^1$ is C or N;
$X^2$ is C;
$X^3$ is N; $R^3$ is selected from hydrogen, cyano, carbamoyl, methyl, hydroxymethyl and methoxycarbonyl;
$R^{10}$ is selected from hydrogen, fluoro, chloro, cyano, carbamoyl, methyl, aminomethyl and acetylaminomethyl;
$R^4$ is hydrogen;
$R^5$ is selected from hydrogen, methyl, ethyl or hydroxymethyl;
$R^6$ is selected from hydrogen or hydroxymethyl;
A is a direct bond, methylene or hydroxymethylene;
Ring C is phenyl, pyrid-2-yl, 1,3-benzodioxo-5-yl or 1H-indol3-yl;
$R^7$ is trifluoromethyl and fluoro; and
n is 0, 1 or 2; wherein the values of $R^7$ may be the same or different;
or a pharmaceutically acceptable salt thereof.

12. A compound, selected from:
3-(5-cyclopropyl-1H-pyrazol-3-yl)-N-[(S)-1-(4-fluorophenypethyl]-3H-imidazo[4, 5-b]pyridin-5-amine;
3-(5-isopropoxy-1H-pyrazol-3-yl)-N-((S)-1-(pyridin-2-yl)ethyl)-3H-imidazo[4, 5-b]pyridin-5-amine;
N-((S)-1-(4-fluorophenypethyl)-3-(5-isopropoxy-1H-pyrazol-3-yl)-3H-imidazo[4, 5-b]pyridin-5-amine;
(2R)-2-(4-fluorophenyl)-2-(3-(5-isopropoxy-1H-pyrazol-3-yl)-3H-imidazo[4, 5-b]pyridin-5-ylamino)ethanol;
6-chloro-N-((S)-1-(4-fluorophenypethyl)-3-(5-isopropoxy-1H-pyrazol-3-yl)-3H-imidazo[4,5-b]pyridin-5-amine;
or a pharmaceutically acceptable salt thereof.

13. A process for preparing a compound of formula (I) or a pharmaceutically acceptable salt thereof which process, wherein variable groups are, unless otherwise specified, as defined in claim 1, wherein said process is selected from:
Process a) reaction of a compound of formula (II):

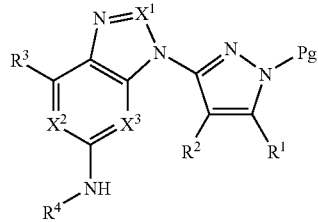

wherein Pg is a nitrogen protecting group; with a compound of formula (III):

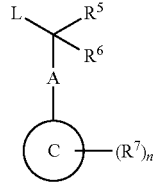

(III)

wherein L is a displaceable group;

Process b) for compounds of formula (I) wherein $R^5$ is hydroxymethyl and $R^6$ is hydrogen; reaction of a compound of formula (II) with an epoxide of formula (IV):

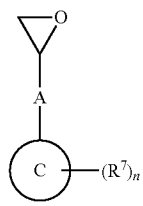

(IV)

Process c) for compounds of formula (I) wherein $X^1$ is =$CR^{10}$—; reacting a compound of formula (V):

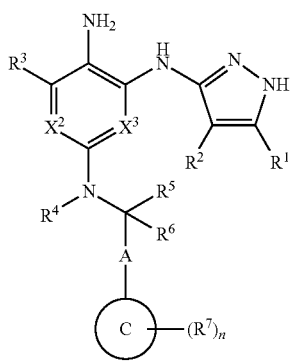

(V)

with a compound of formula (VI):

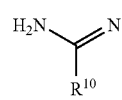

(VII)

Process d) for compounds of formula (I) wherein $X^1$ is =N—; reacting a compound of formula (V) with aqueous $NaNO_2$ solution;

Process e) reacting a compound of formula (VII):

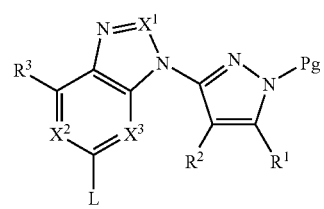

(VII)

wherein L is a displaceable group and Pg is a nitrogen protecting group; with an amine of formula (VIII):

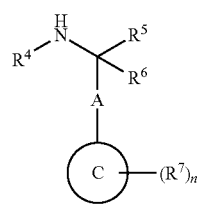

(VIII)

and thereafter if necessary:
  i) converting a compound of the formula (I) into another compound of the formula (I);
  ii) removing any protecting groups;
  iii) forming a pharmaceutically acceptable salt.

14. A pharmaceutical composition comprising a compound of formula (I), or a pharmaceutically acceptable salt thereof, as claimed in claim 1, together with at least one pharmaceutically acceptable carrier, diluent or excipient.

* * * * *